United States Patent [19]

Schubert et al.

[11] Patent Number: 4,966,902

[45] Date of Patent: Oct. 30, 1990

[54] HETEROCYCLIC NEOPHANE ANALOGS, PROCESSES FOR THEIR PREPARATION AND THEIR USE AS PEST-COMBATING AGENTS

[75] Inventors: Hans H. Schubert, Frankfurt am Main; Gerhard Salbeck; Hans-Peter Krause, both of Hofheim am Taunus; Walter Lüders, Heusenstamm; Werner Knauf, Eppstein/Taunus; Anna Waltersdorfer, Frankfurt am Main; Manfred Kern, Lörzweiler, all of Fed. Rep. of Germany

[73] Assignee: Hoechst Aktiengesellschaft, Frankfurt am Main, Fed. Rep. of Germany

[21] Appl. No.: 181,705

[22] Filed: Apr. 13, 1988

[30] Foreign Application Priority Data

Apr. 15, 1987 [DE] Fed. Rep. of Germany ....... 3712752

[51] Int. Cl.$^5$ .................. A01N 43/40; C07D 213/62
[52] U.S. Cl. .................. 514/277; 514/332; 514/335; 514/345; 514/348; 514/350; 514/354; 514/355; 546/261; 546/262; 546/266; 546/288; 546/298; 546/339
[58] Field of Search ............... 514/345, 332, 335, 354, 514/355, 277, 345, 348, 350; 546/288, 290, 301, 302, 339, 261, 262, 266, 296, 298

[56] References Cited

U.S. PATENT DOCUMENTS

| | | | |
|---|---|---|---|
| 3,188,315 | 6/1965 | Villani | 546/348 X |
| 4,562,213 | 12/1985 | Nishida et al. | 514/721 |
| 4,570,005 | 2/1986 | Nakatani et al. | 549/435 |
| 4,661,501 | 4/1987 | Nakatani et al. | 514/345 |
| 4,664,698 | 5/1987 | Tsushima et al. | 546/302 |

FOREIGN PATENT DOCUMENTS

| | | | |
|---|---|---|---|
| 2716125 | 4/1976 | Fed. Rep. of Germany | 546/301 |
| 3117510 | 1/1983 | Fed. Rep. of Germany | . |
| 3317908 | 12/1983 | Fed. Rep. of Germany | . |
| 0116243 | 12/1982 | Japan | 546/302 |
| 2130208A | 5/1984 | United Kingdom | . |
| 2140010A | 11/1984 | United Kingdom | . |

*Primary Examiner*—John M. Ford
*Assistant Examiner*—Catherine Scalzo
*Attorney, Agent, or Firm*—Curtis, Morris & Safford

[57] ABSTRACT

Compounds of the formula (I) and their stereoisomers

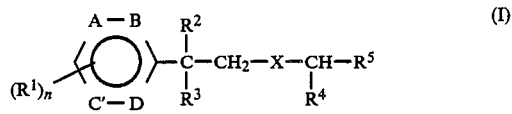

wherein
A, B, C' and D independently of one another denote CH or N, in which at least one of the symbols A, B, C' or D must correspond to a nitrogen atom,
X denotes $CH_2$ or oxygen,
$R^1$ denotes a radical bonded to a carbon atom from the series comprising H, trialkylsilyl, halogen, nitro, cyano, alkenyl, alkynyl, amino, cycloalkyl, phenyl, phenxy, alkoxy, alkenyloxy, alkynyloxy, hydroxycarbonyl, alkylthio, cycloalkyloxy, alkylcarbonyl, alkoxycarbonyl, alkenyloxycarbonyl, alkynyloxycarbonyl, halogenoalkyl, alkoxyalkyl, halogenoalkoxy, halogenoalkylthio, halogenoalkoxyalkyl, alkylthioalkyl, alkoxyalkoxy, halogenoalkoxyalkoxy, alkenyloxyalkoxy, halogenoalkenyloxy, alkoxyalkylthio, alkylthioalkoxy, alkylthioalkylthio, halogenoalkoxycarbonyl, halogenoalkenyloxycarbonyl or dialkylamino or two radicals $R^1$ when they are positioned ortho to one another together denote a methylenedioxy, ethylenedioxy or alkylene radical,
$R^2$ and $R^3$ independently of one another denote alkyl, alkenyl or phenyl, or $R^2$ and $R^3$ denote an alkylene chain which—together with the quaternary carbon atom-forms an unsubstituted or fluorinesubstituted ring having three to six ring members,
$R^4$ denotes —H, F, —CN, —$CCl_3$, —C≡CH, ($C_1$-$C_4$)alkyl, —C—$NH_2$, S
$R^5$ denotes pyridyl, furyl or thienyl which can all be substituted, phthalimidyl, dialkylmaleimidyl, thiophthalimidyl, dihydrophthalimidyl, tetrahydrophthalimidyl or substituted phenyl, or $R^4$ and $R^5$—together with the carbon atom bridging them—denote an optionally substituted indanyl, cyclopentenoyl or cyclopentenyl radical and n denotes 0, 1 or 2, possess advantageous properties for combating pests, in particular insects and acarids. Furthermore, processes for the preparation of compounds of the formula I are described.

6 Claims, No Drawings

HETEROCYCLIC NEOPHANE ANALOGS, PROCESSES FOR THEIR PREPARATION AND THEIR USE AS PEST-COMBATING AGENTS

The insecticidal action of certain benzyl neophyl ether compounds and their hydrocarbon analogs has been disclosed in DE-A-No. 3,117,510 and DE-A-No. 3,317,908.

New heterocyclic neophane compounds having outstanding insecticidal, acaricidal and nematocidal properties have been found, which are clearly superior in their use properties to various conventional preparations.

The present invention therefore relates to the compounds of the formula (I) and their stereoisomers

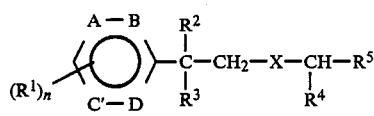   (I)

wherein

A, B, C' or D independently of one another denote CH or N, in which at least one of the symbols A, B, C' or D must correspond to a nitrogen atom, X denotes $CH_2$ or oxygen, $R^1$ denotes a radical bonded to a carbon atom from the series comprising H, $(C_1-C_4)$-alkyl, tri$(C_1-C_4)$-alkylsilyl, halogen, nitro, cyano, $(C_2-C_6)$alkenyl, $(C_2-C_6)$-alkynyl, amino, $(C_3-C_7)$cycloalkyl, phenyl, phenoxy, $(C_1-C_5)$alkoxy, $(C_2-C_4)$alkenyloxy, $(C_2-C_4)$alkynyloxy, hydroxycarbonyl, $(C_1-C_4)$-alkylthio, $(C_3-C_7)$cycloalkyloxy, $(C_1-C_6)$alkylcarbonyl, $(C_1-C_4)$alkoxycarbonyl, $(C_2-C_4)$alkenyloxycarbonyl, $(C_3-C_5)$alkynyloxycarbonyl, $(C_1-C_4)$-halogenoalkyl, $(C_1-C_4)$-alkoxy$(C_1-C_4)$alkyl, $(C_1-C_3)$-halogenoalkoxy, $(C_1-C_3)$halogenoalkylthio, halogeno-$(C_1-C_4)$alkoxy$(C_1-C_4)$alkyl, $(C_1-C_4)$-alkylthio-$(C_1-C_4)$alkyl, $(C_1-C_4)$alkoxy$(C_1-C_4)$alkoxy, alogeno$(C_1-C_4)$alkoxy$(C_1-C_4)$alkoxy, $(C_2-C_4)$alkenyloxy-$(C_1-C_4)$alkoxy, halogeno$(C_2-C_4)$alkenyloxy, $(C_1-C_4)$-alkoxy$(C_1-C_4)$alkylthio, $(C_1-C_4)$alkylthio$(C_1-C_4)$alkoxy, $(C_1-C_4)$alkylthio$(C_1-C_4)$alkylthio, halogeno$(C_1-C_4)$-alkoxycarbonyl, halogeno$(C_2-C_4)$alkenyloxycarbonyl or di$(C_1-C_6$-alkyl)-amino or two radicals $R^1$ when they are positioned ortho to one another together denote a methylenedioxy, ethylenedioxy or $(C_3-C_5)$alkylene radical, $R^2$ and $R^3$ independently of one another denote $(C_1-C_3)$-alkyl, $(C_2-C_8)$alkenyl or phenyl, or $R^2$ and $R^3$ denote an alkylene chain which—together with the quaternary carbon atom—forms an unsubstituted or fluorine-substituted ring having three to six ring members, $R^4$ denotes —H, F, —CN, —$CCl_3$, —C≡CH, $(C_1-C_4)$alkyl,

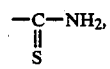

$R^5$ denotes pyridyl, furyl or thienyl which can all be substituted, phthalimidyl, di$(C_1-C_4)$-alkylmaleimidyl, thiophthalimidyl, dihydrophthalimidyl, tetrahydrophthalimidyl or substituted phenyl, or $R^4$ and $R^5$—together with the carbon atom bridging them—denote an optionally substituted indanyl, cyclopentenoyl or cyclopentenyl radical and n denotes 0, 1 or 2.

$R^1$ preferably denotes hydrogen, halogen, $(C_1-C_4)$alkyl, $(C_2-C_6)$-alkenyl, $(C_3-C_7)$cycloalkyl, $(C_1-C_5)$alkoxy, $(C_2-C_4)$alkenyloxy, $(C_1-C_4)$alkylthio, $(C_1-C_4)$halogenoalkyl, $(C_1-C_3)$halogenoalkoxy or—2 $R^1$ radicals together—denote methylenedioxy, in which $R^1$ is positioned in particular in the 3- or 4-position of the heterocyclic radical.

$R^2$ and $R^3$ preferably stand for a $(C_1-C_3)$alkyl radical such as methyl, ethyl, i-propyl and n-propyl or preferably denote, together with the carbon atom bridging them, an unsubstituted or mono- or difluorinated cyclopropyl ring.

$R^4$ preferably stands for hydrogen, fluorine, cyano or $(C_1-C_4)$-alkyl, particularly preferably for hydrogen.

Substituted phenyl $R^5$ preferably stands for a phenyl radical of the formula (A)

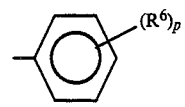   (A)

wherein $R^6$ independently of one another denote H, halogen, $(C_1-C_4)$alkyl, $(C_1-C_4)$alkoxy, $(C_1-C_4)$halogenoalkyl, phenyl or N-pyrrolyl or a radical of the formula (B)

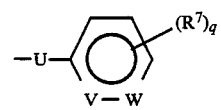   (B)

wherein $R^7$ independently of one another denote H, halogen, $(C_1-C_4)$alkyl, $(C_1-C_4)$alkoxy or $(C_1-C_4)$halogenoalkyl; U denotes =$CH_2$—,

—O— or —S—, preferably —O—; V or W denotes CH or N, in which W must denote CH where V denotes N and vice versa, p denotes an integer from 1 to 5, in particular 1 or 2 or in the case where $R^6$=fluorine denotes to 5 and in the case where $R^6$ corresponds to the group (B), in particular denotes 1 or 2 and q denotes 1 or 2.

Of these radicals, radicals of the formula (A) are of particular significance for $R^5$, wherein $R^6$ denotes H or 4-fluorine and additionally a radical of the formula (B) which is positioned in the 3-position of the phenyl radical of (A).

Optionally substituted pyridyl $R^5$ is, in particular, a mono- or disubstituted pyridyl group of the general formula (C)

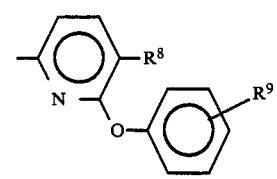   (C)

wherein R⁸ denotes halogen, in particular fluorine, or H and R⁹ denotes hydrogen or halogen with the exception of iodine, (C₁–C₄)alkyl, (C₁–C₄)alkoxy or (C₁–C₄)halogenoalkyl.

Optionally substituted thienyl R⁵ or furyl R⁵ is, in particular, a heterocyclic ring of the general formula (D)

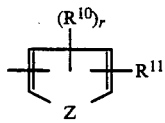

wherein Z denotes O or S,

R¹⁰ denotes H, halogen, (C₁–C₄)alkyl, (C₁–C₄)alkoxy, (C₁–C₄)halogenoalkyl, CN or NO₂, R¹¹ denotes optionally substituted benzyl, propargyl, allyl or phenoxy and r denotes 1 or 2.

Substituted phenyl radicals for R⁵ are of particular importance for the invention.

The following radicals are given as typical examples of the group R⁵:

pentafluorophenyl, 5-benzyl-3-furyl, 4-phenoxyphenyl, 3-phenoxyphenyl, 3-(4-fluorophenoxy)phenyl, 3-(4-chlorophenoxy)phenyl, 3-(4-bromophenoxy)phenyl, 3-(3-fluorophenoxy)phenyl, 3-(3-chlorophenoxy)phenyl, 3-(3-bromophenoxy)phenyl, 3-(2-fluorophenoxy)phenyl, 3-(2-chlorophenoxy)phenyl, 3-(2-bromophenoxy)phenyl, 3-(4-methylphenoxy)phenyl, 3-(3-methylphenoxy)phenyl, 3-(2-methylphenoxy)phenyl, 3-(4-methoxyphenoxy)phenyl, 3-(3-methoxyphenoxy)phenyl, 3-(2-methoxyphenoxy)phenyl, 3-(4-ethoxyphenoxy)phenyl, 3-(phenylthio)phenyl, 3-(4-fluorophenylthio)phenyl, 3-(3-fluorophenylthio)phenyl, 3-benzoylphenyl, 3-benzylphenyl, 3-(4-fluorobenzyl)phenyl, 3-(4chlorobenzyl)phenyl, 3-(3,5-dichlorophenoxy)phenyl, 3-(3,4-dichlorophenoxy)phenyl, 3-(4-chloro-2-methylphenoxy)phenyl, 3-(2-chloro-5-methylphenoxy)phenyl, 3-(4-chloro-5-methylphenoxy)phenyl, 3-(4-ethylphenoxy)phenyl, 3-(3-chloro-5-methoxyphenoxy)phenyl, 3-(2,5dichlorophenoxy)phenyl, 3-(3,5-dichlorobenzoyl)phenyl, 3-(3,4-dichlorobenzoyl)phenyl, 3-(4-methylbenzyl)phenyl, 3-(4-isopropoxyphenoxy)phenyl, 4-fluoro-3-phenoxyphenyl, 4-chloro-3-phenoxyphenyl, 4-bromo-3-phenoxyphenyl, 4-fluoro-3-(4-fluorophenoxy)phenyl, 4-fluoro-3-(4-chlorophenoxy)phenyl, 4-fluoro-3-(4-bromophenoxy)-phenyl, 4-fluoro-3-(4-methylphenoxy)phenyl, 4-fluoro-3-(4-methoxyphenoxy)phenyl, 4-fluoro-3-(3-fluorophenoxy)phenyl, 4-fluoro-3-(3-chlorophenoxy)phenyl, 4-fluoro-3-(3-bromophenoxy)phenyl, 4-fluoro-3-(3-methoxyphenoxy)phenyl, 4-fluoro-3-(4-ethoxyphenoxy)phenyl, 4-fluoro-3-(2-fluorophenoxy)phenyl, 3-methoxy-5-phenoxyphenyl, 2-fluoro-3phenoxyphenyl, 2-fluoro-3-(4-fluorophenoxy)phenyl, 2-fluoro-3-(3-fluorophenoxy)phenyl, 2-fluoro-3-(2-fluorophenoxy)phenyl, 3-fluoro-5-(4-fluorophenoxy)phenyl, 3-fluoro-5-(3-fluorophenoxy)phenyl, 3-fluoro-5-(2-fluorophenoxy)phenyl, 4-methyl-3-phenoxyphenyl, 3-fluoro-5-(4methylphenoxy)phenyl, 3-fluoro-5-(3-methoxyphenoxy)phenyl, 2-fluoro-5-(4-fluorophenoxy)phenyl, 2-fluoro-5(3-fluorophenoxy)phenyl, 2-fluoro-5-(2-fluorophenoxy)phenyl, 2-chloro-3-phenoxyphenyl, 3-fluoro-5-phenoxyphenyl, 2-fluoro-5-phenoxyphenyl, 2-chloro-5-phenoxyphenyl, 2-bromo-5-phenoxyphenyl, 4-chloro-3-(3-methylphenoxy)phenyl, 4-chloro-3-(4-fluorophenoxy)phenyl, 3-chloro-5-phenoxyphenyl, 3-bromo-5-phenoxyphenyl, 4-bromo-3-phenoxyphenyl, 4-trifluoromethyl-3-phenoxyphenyl, 4-fluoro-3-phenylthiophenyl, 4-fluoro-3-benzylphenyl, 3(2-pyridyloxy)phenyl, 3-(3-pyridyloxy)phenyl, 4-fluoro-3-(2-pyridyloxy)phenyl, 4-chloro-3-(2-pyridyloxy)phenyl, 4-bromo-3-(2-pyridyloxy)phenyl, 4-methyl-3-(2-pyridyloxy)phenyl, 4-fluoro-3-(3-pyridyloxy)phenyl, 4-chloro-3-(3pyridyloxy)phenyl, 4-bromo-3-(3-pyridyloxy)phenyl, 4-methyl-3-(3-pyridyloxyphenyl), 2-methyl-3-phenylphenyl, 2-methyl-3-(N-pyrrolyl)phenyl, 6-phenoxy-2-pyridyl, 6(4-fluorophenoxy)-2-pyridyl, 6-(4-chlorophenoxy)-2-pyridyl, 6-(4-bromophenoxy)-2-pyridyl, 6-(4-methylphenoxy)-2 -pyridyl, 6-(4-methoxyphenoxy)-2-pyridyl, 6-(4-ethoxyphenoxy)-2-pyridyl, 6-(3-bromophenoxy)-2-pyridyl, 6-(3-methoxyphenoxy)-2-pyridyl, 6-(2-fluorophenoxy)-2-pyridyl, 6-(2-chlorophenoxy)-2-pyridyl, 6-(2-bromophenoxy-2-pyridyl, 5-propargyl-3-furyl, N-phthalimidyl, N-3,4,5,6-phthalimidyl, 2-methyl-5-propargyl-3-furyl, 4-t-butylphenyl, 4-methylphenyl, 4-isopropylphenyl, 4-(2-chloro-4-trifluoromethyl-2-pyridyloxy)phenyl, 4-cyclohexylphenyl, 4-difluoromethoxyphenyl, 4-biphenylyl, 4trimethylsilylphenyl and 4-phenoxy-2-thienyl.

Further typical examples of the group

are:

2-allyl-3-methylcyclopent-2-en-1-on-4-yl and 4-phenylindian-2-yl.

The present invention also relates to a process for the preparation of the compounds of the general formula (I), wherein (a) for compounds having X=O a compound of the formula (II) or (III)

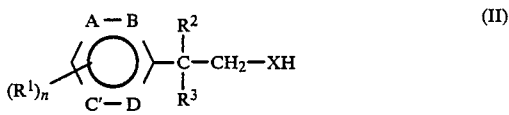

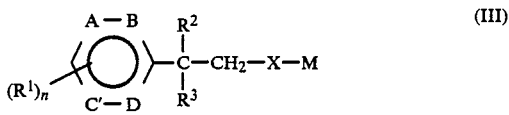

is condensed with an alkylating agent of the formula IV

wherein Y denotes a nucleofugic leaving group such as, for example, halogen or sulfonate and M corresponds to an alkali metal equivalent or an alkaline earth metal equivalent, in particular Li, Na, K or Mg, if appropriate in the presence of a base, or (b) for compounds having X=0 a compound of the formula

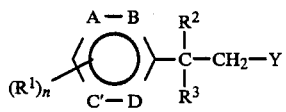 (V)

is condensed with an XH-acid compound of the type (VI)

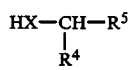 (VI)

in the presence of a base or with an organometallic compound of the type VII

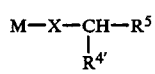 (VII)

having $R^{4'}$ = H or ($C_1$-$C_4$)alkyl or (c) for compounds having X=CH2 a compound of the general formula VIII

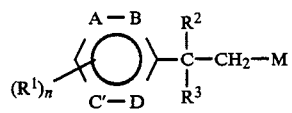 (VIII)

is condensed with a compound of the type (IX)

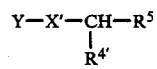 (IX)

having $X'$ = CH_2, or (d) a compound of the formula (X)

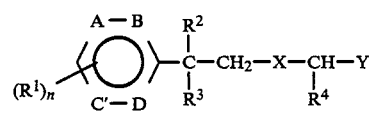 (X)

is condensed with an organometallic reagent of the type (XI)

 (XI)

(e) for compounds having $R^4$=H and X=CH_2 an aldehyde of the formula (XII)

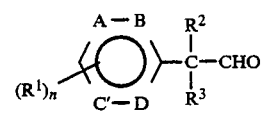 (XII)

is condensed with a ketone of the formula (XIII)

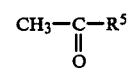 (XIII)

to form an intermediate (XIV)

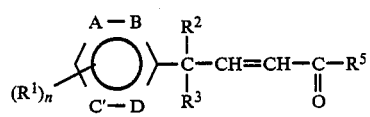 (XIV)

and this is subsequently reduced in a customary manner, or (f) for compounds having X=CH_2 an aldehyde of the formula (XV)

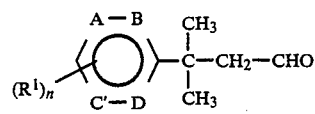 (XV)

is condensed with an ylide of the formula (XVI) or a phosphonate of the formula (XVII)

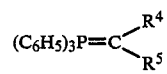 (XVI)

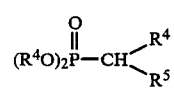 (XVII)

to form an intermediate (XVIII)

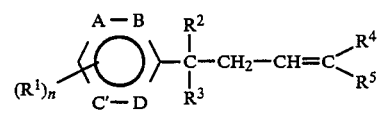 (XVIII)

and this is subsequently reacted with a reductant to form the final product (I) having X=CH_2.

The substances (II) or (III) to be used as starting compounds in preparation process (a) can be obtained, for example, by a multi-step synthesis from the heterocyclic rings (XIX)

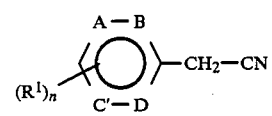 (XIX)

by first introducing the two radicals $R^2$ and $R^3$ stepwise with the aid of strong bases such as, for example, sodium hydride and alkylating agents such as alkyl iodide or dialkyl sulfate, by means of which the intermediate (XX) is obtained

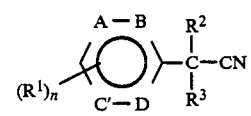 (XX)

this is then first hydrolyzed to form the corresponding carboxylic acid and finally reduced using strong reductants such as, for example, LiAlH4 to form the desired alcohol (II).

The heterocyclic rings of the type V to be used as starting compounds in preparation process (b) can be obtained by halogenation of the alcohols (II) (X=O)

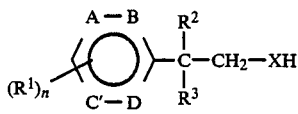

which is carried out by standard methods.

The aldehydes of the general formula (XII) required as starting compounds in preparation process (e) can be obtained in a simple manner by oxidation of the corresponding alcohols (II) (X=O), (preparation described further above)

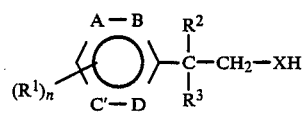

using the oxidant pyridine x $SO_3$.

The aldehydes of the general formula (XV) required as starting compounds in preparation process (f) are obtained inter alia by carbonylation of the metal compounds (VIII)

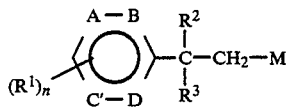

which are obtainable from the corresponding halides (V) with, for example, N,N-dimethylformamide.

The precursors and intermediates which are not described in greater detail can be prepared by customary standard methods. Thus all mentioned organometallic intermediates can be obtained by customary metallization reaction such as hydrogen/metal exchange or—preferably—halogen/metal exchange in all its variations.

The mentioned process variations (c) and (d) are preferably carried out in a diluent whose nature depends upon the type of organometallic compound employed. Those diluents which are suitable in particular are aliphatic and aromatic hydrocarbons such as, for example, pentane, hexane, heptane, cyclohexane, petroleum ether, benzine, ligroin, benzene, toluene and xylene, ethers such as, for example, diethyl ether and dibutyl ether, glycol dimethyl ether, diglycol dimethyl ether, tetrahydrofuran and dioxane, and finally all possible mixtures of the previously mentioned solvents.

The reaction temperature in the abovementioned process variations is between −75° C. and +150° C., preferably between −75° C. and +105° C. The starting materials are customarily employed in equimolar amounts. An excess of one or the other reaction component is possible, however.

For process variations (a), (b), (e) and (f) mentioned further above, essentially the same applies as for variations (c) and (d). By employing the educts of the type (II) and (VI) and also the carbonyl compounds (XII) and (XIII), it is still possible to employ additional diluents, however. Thus, suitable diluents in these cases are also ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulfoxide, tetramethylenesulfone and hexamethylphosphoric triamide. Bases used are inorganic bases such as, for example, hydroxides, hydrides, carbonates or hydrogen carbonates of alkali metals or alkaline earth metals, and also organic bases such as, for example, pyridine, triethylamine, N,N-diisopropylethylamine or diazabicyclooctane.

The isolation and, where appropriate, purification of the compounds of the formula (I) takes place according to generally customary methods, for example by evaporating the solvent (if appropriate under reduced pressure) and subsequent distillation or chromatography or by dividing the crude product between two phases and subsequent customary workup from there on.

The compounds of the general formula (I) are readily soluble in most organic solvents.

The active compounds are suitable for combating animal pests, in particular insects, arachnida and nematodes, encountered in agriculture, in forestry, in the protection of stored products and of materials, and in the hygiene field, and well tolerated by plants and have favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera spec.* From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blatella germanica, Acheta domesticus, Gryllotalpa spp., Locusta migratoria migratorioides, Melanoplus differentialis* and *Schistocerca gregaria.* From the order of the Dermaptera, for example, *Forficula auricularia.* From the order of the Isoptera, for example, *Reticulitermes spp..* From the order of the Anoplura, for example, *Phylloera vastatrix, Pemphigus spp., Pediculus humanus corporis, Haematopinus spp.* and *Linognathus spp..* From the order of the Mallophaga, for example, *Trichodectes spp.* and *Damalinea spp..* From the order of the Thysanoptera, for example, *Hercinothrips femoralis* and *Thrips tabaci.* From the order of the Heteroptera, for example, *Eurygaster spp., Dysdercus intermedius, Piesma quadrata, Cimexlectularius, Rhodnius prolixus* and *Triatoma spp..* From the order of the Homoptera, for example, *Aleurodes brassicae, Bemisia tabaci, Trialeurodes vaporariorum, Aphis gossypii, Bravicornyne brassicae, Cryptomyzus ribis, Doralis fabea, Doralis pomi, Eriosoma lanigerum, Hyalopterus arundinis, Macrosiphium avenae, Myzus spp., Phorodon humuli, Rhopalosiphum padi, Empoasca spp., Euscelus bilobatus, Nephotettix cincticeps, Lecanium corni, Saissetia oleae, Laodelphax striatellus, Nilaparvata lugens, Aonidiella auroantii, Aspidiotus hederae, Pseudococcus spp.* and *Psylla spp..* From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Buceulatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana. From the order of the Coleoptera, for example, Anobium punctatum, Rhizopertha dominica, Bruchidius obtectus, Acanthoscelides obtectus, Hylotrupes bajulus, Agelastica alni, Leptinotarsa decemlineata, Phaedon cochlearieae, Diabrotica spp., Psylliodes chrysocephala, Epilachna varivestis, Atomaria spp., Oryzaephilus surinamensis, Anthonomus spp, Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus-spp., Melolontha melolontha, Amphimallon solstitialis and Costelytra zealandica. From the order of the Hymenoptera, for example, Diprion spp., Hoplocampa spp, Lasius spp., Monomorium pharaonis and Vespa spp.. From the order of the Diptera, for example, Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp, Oestrus spp, Hypoderma spp., Tabanus spp., Tannia spp., Bibio hortulanus, Oscinella frit, Phorbia spp., Pegomyia hyoscyami, Ceratitis capitata, Dacus oleae and Tipula paludosa. From the order of the Siphonaptera, for example, Xenopsylla cheopis and Ceratophyllus spp. From the order of the Arachnida, for example, Scorpio maurus and Latrodectus mactans.

From the order of the Acarina, for example, Acarus siro, Argas spp, Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp..

Furthermore, the compounds have an excellent action against nematodes which are harmful to plants, for example those of the Meloidogyne, Heterodera, Ditylenchus, Aphelenchoides, Radopholus, Globodera, Pratylenchus, Longidorus and Xiphinema genera. The invention also relates to agents which contain the compounds of the formula I in addition to suitable formulation auxiliaries.

The agents according to the invention contain the active compounds of the formula I, in general from 1–95% by weight. They can be used in the customary preparations as wettable powders, emulsifiable concentrates, sprayable solutions, dusting agents or granules.

Wettable powders are preparations which are uniformly dispersible in water, which, besides the active compound, in addition to a diluent or inert substance contain wetting agents, for example polyoxyethylated alkyl phenols, polyoxyethylated fatty alcohols, alkyl sulfonates or alkyl phenol sulfonates and dispersing agents, for example sodium ligninsulfonate, sodium 2,2'-dinaphthylmethane-6,6'-disulfonate, sodium dibutylnaphthalenesulfonate and also sodium oleylmethyltaurate.

Emulsifiable concentrates are prepared by dissolving the active compound in an organic solvent, for example butanol, cyclohexanone, dimethylformamide, xylene and also higher-boiling aromatics or hydrocarbons with the addition of one or more emulsifiers. Examples of emulsifiers which can be used are: calcium alkylarylsulfonates, such as calcium dodecylbenzenesulfonate or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc, natural clays such as kaolin, bentonite, poryphillite or diatomaceous earth. Granules can be prepared either by spraying the active compound onto adsorptive, granulated inert material or by applying concentrates of active compound by means of adhesives, for example polyvinyl alcohol, sodium polyacrylates and also mineral oils, to the surface of supports such as sand, kaolinites, or granulated inert material. Suitable active compounds can also be prepared in the customary manner for the preparation of fertilizer granules—if desired mixed with fertilizers.

The active compounds according to the invention can be present in their commerically available formulations and in the use forms, prepared from these formulations, as a mixture with other active compounds, such as insecticides, baits, sterilizing agents, acaricides, nematicides, fungicides, growth-regulating substances or herbicides.

The insecticides include, for example, phosphates, carbamates, carboxylates, formamidines, tin compounds, substances produced by microorganisms and insect growth regulators, inter alia.

Preferred components for the mixture are 1. from the phosphorus compounds group azinphosethyl, azinphos-methyl, 1-(4-chlorophenyl-4-(O-ethyl,S-propyl)phosphoryloxypyrazole (TIA 230), chlorpyrifos, coumaphos, demeton, demeton-S-methyl, diazinon, etrimfos, fenitrothion, fenthion, parathionmethyl, phosalone, pirimiphos-ethyl, pirimiphos-methyl, profenofos, prothiofos, sulprofos, triazophos and trichlorphon.

2. From the carbamate group
aldicarb, bendiocarb, BPMC (2-(1-methylpropyl)-phenylmethylcarbamate), butocarboxim, butoxicarboxim, carbaryl, carbofuran, carbosulfan, cloethocarb, isoprocarb, methomyl, oxamyl, pirimicarb, promecarb, propoxur and thiodicarb.

3. From the carboxylates group
allethrin, alphametrin, bioallethrin, bioresmethrin, cycloprothrin, cyfluthrin, cyhalothrin, cypermethrin, deltamethrin, α-cyano-3-phenyl-2-methylbenzyl 2,2-dimethyl-3-(2-chloro-2-trifluoromethylvinyl)-cyclopropanecarboxylate carboxylate (FMC 54800), fenpropathrin, fenfluthrin, fenvalerate, flucythrinate, flumethrin, fluvalinate, permethrin, resmethrin and tralomethrin.

4. From the amidine group
amitraz and chlordimeform;

5. From the tin compounds group
azocyclotin, cyhexatin and fenbutatin oxide

6. From the growth regulators group
fenoxycarb, flufenoxuron, buprofezin, cyromazine, flubenzimin, diflubenzuron, triflumuron, N-(((3,5-dichloro-4-(1,1,2,2-tetrafluoroethoxy)phenyl)aminocarbonyl)-2,6-difluorobenzamide (XRD 473), tetrafluben-zuron, chlorfluazuron, flucylooxuron, hydroprene, methoprene, N-(2-fluorobenzoyl)-N'-(4-(2-chloro-4-trifluoromethyl-1-phenyl-mercapto)phenyl)urea, N-(2- chlorobenzoyl)-N'-(4-(2-chloro-4-trifluoromethyl-1-phenylmercapto)phenyl)urea, N-(2,6-difluorobenzoyl)-N'-(4-(2-chloro-4-trifluoromethyl-1-phenylmercapto)-phenyl)urea, ethyl N-(N-(2-chloro-4-trifluoromethyl-1-phenylmercapto)phenyl)carbamoyl)-2-fluorobenzocarboximidate, ethyl N-(N-(2-chloro-4-trifluoromethyl-1-phenylmercapto)phenyl)carbamoyl)-2chlorobenzocarboximidate and ethyl N-(N-(2-chloro-4-trifluoromethyl-1-phenylmercapto)phenyl)carbamoyl)-2,6difluorobenzocarboximidate.

7. Miscellaneous

α- and β-acermectins, Bacillus thuringiensis, bensultap, binapacryl, bisclofentezin, buprofezin, cartap, cyromacin, dicofol, endosulfan, ethoproxyfen, fenoxycarb, hexythiazox, 3- 2-(4-ethoxyphenyl)-2-methyl-propoxymethyl-1,3-diphenyl ether (MTI-500), 5- 4-(4-ethoxyphenyl-4-methylpentyl -2-fluoro-1,3-diphenyl ether (MTI-800), 3-(2-chlorophenyl)-3-hydroxy-2-(2-phenyl-4-thiazolyl)-propenenitrile (SN 72129), thiocyclam, core polyhedral viruses and granulosis viruses.

The active compound content of the use forms prepared from the commercially available formulations can vary within wide ranges. The active compound concentration of the use forms can be from 0.0000001 up to 100% by weight of active compound, preferably between 0.00001 and 1% by weight.

Use takes place in a customary manner appropriate for the use forms.

The active compounds according to the invention are also suitable for combating ectoparasites and endoparasites, preferably ectoparasitic insects, from the veterinary medicinal sector or the animal husbandry sector.

The use of the active compounds according to the invention occurs in a known manner here, such as by dermal use in the form of, for example, dipping, spraying, pouring on and spotting on and powdering.

A. FORMULATION EXAMPLES (a) A dusting agent is obtained by mixing 10 parts by weight of active compound and 90 parts by weight of talc as the inert substance and pulverizing in a hammer mill.

(b) An easily water-dispersible, wettable powder is obtained by mixing 25 parts by weight of active compound, 65 parts by weight of kaolin-containing quartz as the inert substance, 10 parts by weight of potassium ligninsulfonate and 1 part by weight of sodium oleoylmethyltaurate as the wetting and dispersing agent and grinding the mixture in a pinned disk mill.

(c) A dispersion concentrate which is easily dispersible in water is prepared by mixing 20 parts by weight of active compound with 6 parts by weight of alkylphenol polyglycol ether (Triton X 207), 3 parts by weight of isotridecanol polyglycol ether (8 EO) and 71 parts by weight of paraffinic mineral oil (boiling range, for example, about 255° to above 377° C.) and grinding the mixture in a ball mill to a fineness of under 5 microns.

(d) An emulsifiable concentrate can be prepared from 15 parts by weight of active compound, 75 parts by weight of cyclohexanone as the solvent and 10 parts by weight of oxyethylated nonylphenol (10 EO) as the emulsifier.

(e) Granules can be prepared from 2 to 15 parts by weight of active compound and an inert granule support material such as attapulgite, pumice granules and/or quartz sand.

B. CHEMICAL EXAMPLES

EXAMPLE 1

2-Methyl-2-(6-chloro-pyrid-3-yl)-propyl 3-phenoxy-benzyl ether (compound No. 18 Table 1)

(1.1) 6-Chloropyridine-3-methanol 69.5 g (0.5 mol) of 6-hydroxynicotinic acid are introduced into a mixture of 200 g (1 mol) of phosphorus pentachloride and 233 g (1.5 mol) of phosphorus oxychloride at room temperature, the mixture is stirred at 95° C. for 5 hours and excess phosphorus chlorides are then removed in vacuo. The crystalline residue is introduced into a solution of 75 g (1.98 mol) of sodium borohydride in 1,000 ml of water, the temperature being maintained at 30° C. at most. The mixture is then stirred at room temperature until the completion of gas evolution and is filtered with suction from solid material, and the filtrate is extracted using ether.

After removing the solvent from the organic phase, 44.5 g (62% of theory) of oily crude product are obtained. The residue is distilled at 0.4 mbar (b.p. 110°–115° C.) to give 36.6 g (51% of theory).

(1.2) 2-Chloro-5-chloromethyl-pyridine 85 ml of thionyl chloride are added cautiously to 14.4 g (0.1 mol) of 6-chloro-pyridine-3-methanol. 8.1 g (0.1 mol) of pyridine are then added dropwise and the mixture is heated under reflux until gas evolution is complete. Excess thionyl chloride is removed in vacuo and the residue is poured onto ice. The precipitate is filtered off with suction and dried. Yield 10.6 g (65.5% of theory), m.p.: 38°–40° C. The crude product can be used further without purification.

(1.3) 6-Chloro-pyridine-3-acetonitrile 25.6 g of sodium cyanide (0.522 mol) are dissolved in 123 g of dimethyl sulfoxide, the mixture is heated to 90° C. and 68.9 g (0.43 mol) of 2-chloro-5-chloromethyl-pyridine are introduced in portions. During this, the temperature rises to 130° C. The mixture is allowed to cool to room temperature, poured into water and extracted using ether. The solvent is removed and the crude product is distilled at 1.0 mbar (130°–135° C.). M.p.: 80° C. Yield: 41.1 g (63% of theory).

(1.4) 2-(6-Chloro-pyrid-3-yl)-2-methyl-propanenitrile 24 g (0.8 mol) of 80% strength sodium hydride (in white oil) are suspended in 640 ml of tetrahydrofuran and 56 g (0.37 mol) of 6-chloro-pyridine-3-acetonitrile, dissolved in 160 ml of tetrahydrofuran, are added dropwise. After completion of gas evolution, 105.3 g (0.74 mol) of methyl iodide, dissolved in 160 ml of tetrahydrofuran, are added dropwise at 0°–20° C. The mixture is stirred at room temperature for a further 3 hours and then poured into 860 ml of water. The crude product is extracted using ether and, after removing the solvent, is distilled at 0.3 mbar (b.p. 110°–120° C.). 49.1 g (73.5% of theory) of a yellowish oil are thus obtained, which crystallizes on standing. M.p.: 63°–65° C.

(1.5) 2-(6-Chloro-pyrid-3-yl)-2-methyl-propanol 3.6 g (20 mmol) of 2-(6-chloro-pyrid-3-yl)-2-methyl-propionitrile are introduced into 50 ml of toluene, and 25 ml of a diisobutylaluminum hydride solution (1M in toluene) is added dropwise without cooling, by means of which the internal temperature rises to 45° C. The mixture is stirred for 2 hours at room temperature. 10 ml of methanol, 50 ml of water and 90 ml of 2N sulfuric acid are then cautiously added successively, and the mixture is stirred for 2 hours at room temperature and finally for 2 hours at 50° C. The toluene phase is separated off and the solvent is removed. The residue is dissolved in 10 ml of methanol and a solution of 0.1 g of sodium and 0.4 g (10.6 mmol) of sodium borohydride in 10 ml of methanol are added. The mixture is stirred for 1 hour at room temperature and acidified with 0.7 g of acetic acid, and the solvent is removed. The residue is boiled with ethyl acetate, the ester phase is boiled off and the solvent is removed in vacuo. The oily crude product is distilled in a bulb tube; 0.15 mbar, apparatus temperature 170° C. Yield 2.5 g (67% of theory) of a colorless oil.

(1.6) 2-(6–Chloro-pyrid-3-yl)-2-methyl-propyl 3-phenoxy-benzyl ether 1.9 g (10.2 mmol) of 2-(6-chloro-pyrid-3-yl)-2-methylpropanol are dissolved in 15 ml of toluene, 2.7 g (10.3 mmol) of 3-phenoxy-benzyl bromide are added and a solution of 0.6 g (1.8 mmol) of tetra-n-butylammonium hydrogen sulfate in 5 g of 50% strength sodium hydroxide solution is added. The mixture is stirred at 70°-80° C. for 2 hours, mixed with a mixture of 2 ml of methanol and 2 ml of concentrated ammonia water and finally all distributed between water and toluene. The organic phase is washed with ammonium chloride solution, the solvent is removed and the crude product is purified through a silica gel column. 2.4 g (62.9% of theory) of a weakly yellowish oil are thus obtained. The oil is distilled in the bulb tube at 0.03 mbar and 230°-240° C. apparatus temperature.

EXAMPLE 2

1-(6–Chloro-pyrid-3-yl)-cyclopropyl)-methyl 3-phenoxybenzyl ether (compound No. 513 in Table 2)

(2.1)
1-(6–Chloro-pyrid-3-yl)-cyclopropane-1-carbonitrile (corresponds to Process 1.4 in Example 1).

6.5 g (0.217 mol) of 80% strength sodium hydride in white oil are suspended in 170 ml of tetrahydrofuran and a solution of 15.3 g (0.1 mol) of 6-chloro-pyridine-3-acetonitrile in 60 ml of tetrahydrofuran is added dropwise. The mixture is stirred until completion of gas evolution, cooled and a solution of 14.3 g (0.1 mol) of 1-bromo-2-chloro-ethane in 15 ml of tetrahydrofuran are added dropwise at 5°-20° C. The mixture is stirred for 2 hours at room temperature, poured into concentrated sodium chloride solution and extracted using ether. The crude product, freed from solvent, is taken up in ethyl acetate and filtered through a bed of 200 g of silica gel. 14.3 g of a brownish, semi-crystalline material are thus obtained, which is purified by bulb tube distillation. 5.8 g (32.5% of theory) of an oil, which solidifies on cooling, are distilled at an apparatus temperature of 130°-140° C. and 0.08 mbar.

This substance can be converted into compound No. 513 (Table 2) in analogy to Processes 1.5 and 1.6 mentioned in Example 1.

EXAMPLE 3

(2-(6-Ethoxy-pyridazin-3-yl)-2-methyl-propyl) 3-phenoxy-benzyl ether (compound No. 343 in Table 1)

(3.1) 2-(6-Hydroxy-pyridazin-3-yl)-propanenitrile 60.4 g (2.02 mol) of 80% strength sodium hydride in white oil are suspended in 2 liters of tetrahydrofuran and 311.8 g (2.02 mol) of tert.-butyl 2-cyanopropionate are added dropwise at 20°-30° C. During the course of 45 minutes this clear solution is added dropwise to a solution of 298 g (2.0 mol) of 3,6-dichloropyridazine and the mixture is heated under reflux for 2 hours. 317 ml of acetic acid are then added and the solvent is removed in vacuo. The residue is taken up in a mixture of 6,400 ml of acetic acid, 250 ml of acetic anhydride and 32 g of p-toluenesulfonic acid monohydrate, heated under reflux for 3 hours and again brought to dryness in vacuo. The residue is suspended in a little water, adjusted to pH 5 with sodium hydroxide solution and the water removed by evaporation. The residue is extracted hot using ethyl acetate. 99.7 g (33% of theory) of crude product are thus obtained, which can be employed for the following reaction without further processing.

(3.2) 2-(6-Chloro-pyridazin-3-yl)-propanenitrile 1.5 g (10 mmol) of 2-(6-hydroxy-pyridazin-3-yl)-propanenitrile are mixed with 5 g of phosphorus oxychloride and the mixture is stirred at 80°-90° C. for 45 minutes. The mixture is poured onto 30 g of ice, adjusted to pH 6 using 2N NaOH and extracted using ether. After removal of the solvent, an oil remains which solidifies on standing. Yield: 1 g (59.7% of theory); m.p.: 65° C. from hexane.

(3.3)
2-(6–Chloro-pyridazin-3-yl)-2-methyl-propanenitrile 3.9 g (0.131 mol) of 80% strength sodium hydride in white oil are suspended in 380 ml of tetrahydrofuran and a solution of 18.9 g (0.113 mol) of 2-(6-chloropyridazin-3-yl)-propanenitrile in 80 ml of tetrahydrofuran is added at 15°-20° C. After completion of gas evolution, a solution of 16.3 g (0.115 mol) of methyl iodide in 50 ml of tetrahydrofuran is added dropwise and the mixture is stirred for 1 hour at room temperature. The mixture is poured into 1.4 liters of concentrated sodium chloride solution and extracted with ether. The crude product which remains after removing the solvent is purified by bulb tube distillation.

Apparatus temperature: 180°-190° C., 0.1 mbar.
Yield 8.4 g (41% of theory) oil which solidifies on standing.
M.p.: 107°-111° C.

This nitrile can be converted into 2-(6-chloro-pyridazin-3-yl)-2-methyl-propanol in analogy to Process 1.5 mentioned in Example 1.

(3.4) 2-(6-Ethoxy-pyridazin-3-yl)-2-methyl-propanol 1.6 g (0.053 mol) of 80% strength sodium hydride in white oil are suspended in 50 ml of dimethyl sulfoxide and 2.5 g (0.055 mol) of ethanol are added dropwise at 15°-20° C. After completion of gas evolution, a solution of 1.0 g (0.005 mol) of 2-(6-chloro-pyridazin-3-yl)-2-methylpropanol in 20 ml of dimethyl sulfoxide is allowed to run in and the mixure is warmed to 90°-100° C. for 1.5 hours. After cooling, the mixture is poured into concentrated sodium chloride solution and extracted with ether. After removing the solvent, a yellow oil remains as the crude product. Yield: 0.6 g (61% of theory).

This crude product can be converted into compound No. 343 of Table 1 directly and in analogy to Process 1.6 mentioned in Example 1. The preparation of the following compounds of the formula

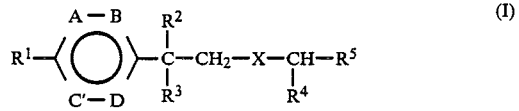

(Tables 1 and 2) having X=0 takes place analogously to the abovementioned examples. Compounds having X=$CH_2$ are preferably obtained by Processes (e) and (f).

TABLE 1

| | | | $R^2$ and $R^3$ = $CH_3$, A = N, CH or C—$R^1$ | | | | | | |
|---|---|---|---|---|---|---|---|---|---|
| Compound No. | A | $R^1$ | B | C' | D | X | $R^4$ | $R^5$ | Physical data |
| 1 | N | EtO | CH | CH | CH | $CH_2$ | H | 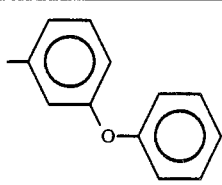 | b.p$_{0.01}$ = 225–230° C. |
| 2 | N | EtO | CH | CH | CH | $CH_2$ | H | 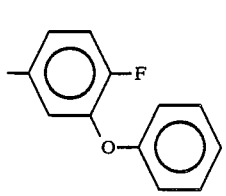 | b.p$_{0.05}$ = 240–245° C. |
| 3 | N | EtO | CH | CH | CH | $CH_2$ | H | 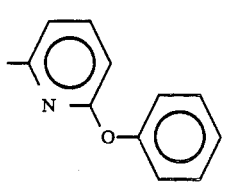 | |
| 4 | N | EtO | CH | CH | CH | $CH_2$ | H | 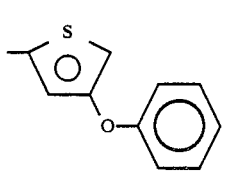 | |
| 5 | N | EtO | CH | CH | CH | $CH_2$ | H | 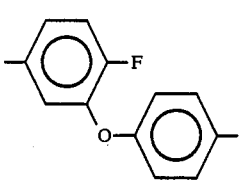 | b.p$_{0.02}$ = 230–240° C. |
| 6 | N | EtO | CH | CH | CH | $CH_2$ | CN | 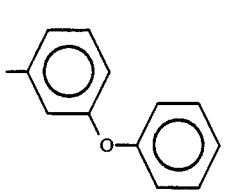 | |
| 7 | N | EtO | CH | CH | CH | $CH_2$ | CN | 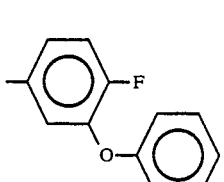 | |

TABLE 1-continued
| | | | R² and R³ = CH₃, A = N, CH or C—R¹ | | | | | | |
|---|---|---|---|---|---|---|---|---|---|
| Compound No. | A | R¹ | B | C' | D | X | R⁴ | R⁵ | Physical data |
| 8 | N | EtO | CH | CH | CH | O | H | 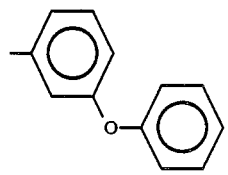 | b.p.$_{0.005}$ = 210–220° C. |
| 9 | N | EtO | CH | CH | CH | O | H | 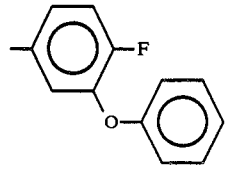 | b.p.$_{0.1}$ = 230–235° C. |
| 10 | N | EtO | CH | CH | CH | O | H | 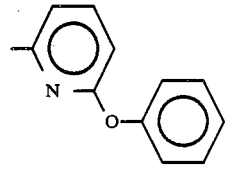 | |
| 11 | N | EtO | CH | CH | CH | O | CN | 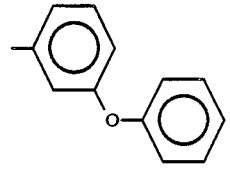 | |
| 12 | N | Cl | CH | CH | CH | CH₂ | H | 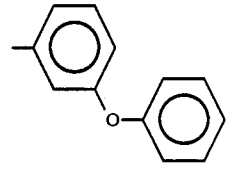 | |
| 13 | N | Cl | CH | CH | CH | CH₂ | H | 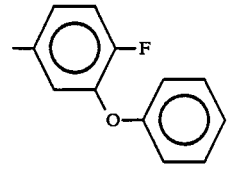 | |
| 14 | N | Cl | CH | CH | CH | CH₂ | H | 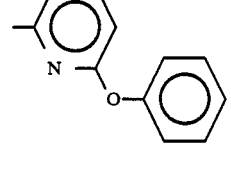 | |
| 15 | N | Cl | CH | CH | CH | CH₂ | H | 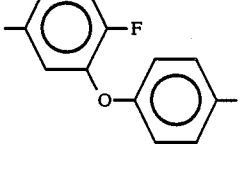 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 16 | N | Cl | CH | CH | CH | CH₂ | CN | 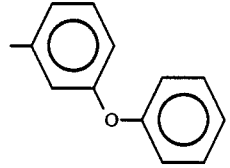 | |
| 17 | N | Cl | CH | CH | CH | CH₂ | CN | 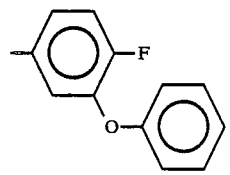 | |
| 18 | N | Cl | CH | CH | CH | O | H | 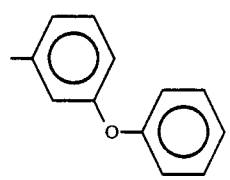 | b.p.$_{0.03}$ = 230–240° C. |
| 19 | N | Cl | CH | CH | CH | O | H | 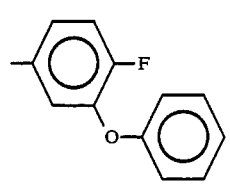 | b.p.$_{0.01}$ = 225–230° C. |
| 20 | N | Cl | CH | CH | CH | O | H | 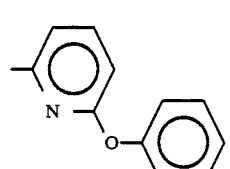 | |
| 21 | N | Cl | CH | CH | CH | O | CN | 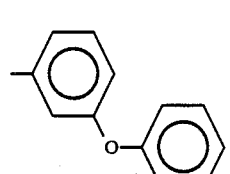 | |
| 22 | N | Cl | CH | CH | CH | O | CH₃ | 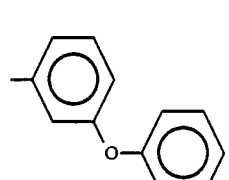 | |
| 23 | N | H₃CO | CH | CH | CH | CH₂ | H | 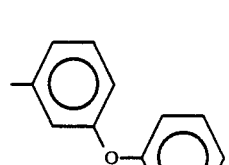 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 24 | N | H₃CO | CH | CH | CH | CH₂ | H | 2-fluorophenoxyphenyl | |
| 25 | N | H₃CO | CH | CH | CH | CH₂ | H | pyridinyloxyphenyl | |
| 26 | N | H₃CO | CH | CH | CH | CH₂ | H | 2-fluoro-4'-fluorophenoxyphenyl | |
| 27 | N | H₃CO | CH | CH | CH | CH₂ | CN | phenoxyphenyl | |
| 28 | N | H₃CO | CH | CH | CH | CH₂ | CN | 2-fluorophenoxyphenyl | |
| 29 | N | H₃CO | CH | CH | CH | O | H | phenoxyphenyl | |
| 30 | N | H₃CO | CH | CH | CH | O | H | 2-fluorophenoxyphenyl | b.p₀.₀₇ = 220–240° C. |
| 31 | N | H₃CO | CH | CH | CH | O | H | pyridinyloxyphenyl | |

TABLE 1-continued
| | | | R² and R³ = CH₃, A = N, CH or C—R¹ | | | | | | |
|---|---|---|---|---|---|---|---|---|---|
| Compound No. | A | R¹ | B | C' | D | X | R⁴ | R⁵ | Physical data |
| 32 | N | H₃CO | CH | CH | CH | O | CN | 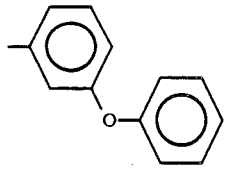 | |
| 33 | N | H₃CO | CH | CH | CH | O | CH₃ | 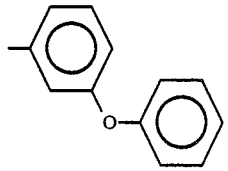 | |
| 34 | N | EtS | CH | CH | CH | CH₂ | H | 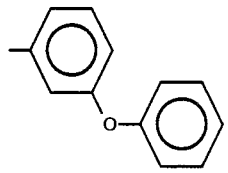 | |
| 35 | N | EtS | CH | CH | CH | CH₂ | H | 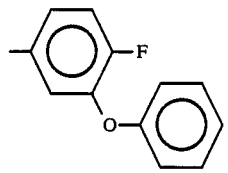 | |
| 36 | N | EtS | CH | CH | CH | CH₂ | H | 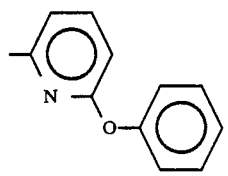 | |
| 37 | N | EtS | CH | CH | CH | CH₂ | H | 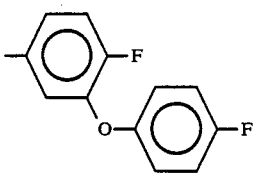 | |
| 38 | N | EtS | CH | CH | CH | CH₂ | CN | 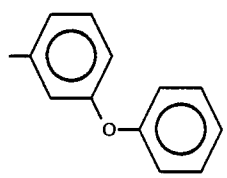 | |
| 39 | N | EtS | CH | CH | CH | CH₂ | CN | 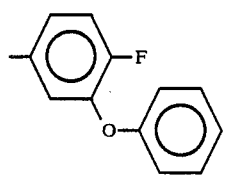 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 40 | N | EtS | CH | CH | CH | O | H | 4-phenoxyphenyl | |
| 41 | N | EtS | CH | CH | CH | O | H | 3-fluoro-4-phenoxyphenyl | b.p.$_{0.01}$ = 220–230° C. |
| 42 | N | EtS | CH | CH | CH | O | H | (6-phenoxypyridin-3-yl) | |
| 43 | N | EtS | CH | CH | CH | O | CN | 4-phenoxyphenyl | |
| 44 | N | EtS | CH | CH | CH | O | CH₃ | 4-phenoxyphenyl | |
| 45 | N | H₃CS | CH | CH | CH | CH₂ | H | 4-phenoxyphenyl | |
| 46 | N | H₃CS | CH | CH | CH | CH₂ | H | 3-fluoro-4-phenoxyphenyl | |
| 47 | N | H₃CS | CH | CH | CH | CH₂ | H | (6-phenoxypyridin-3-yl) | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 48 | N | H₃CS | CH | CH | CH | CH₂ | H | 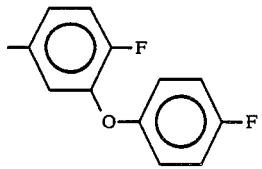 | |
| 49 | N | H₃CS | CH | CH | CH | CH₂ | CN | 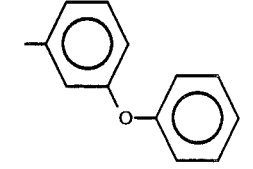 | |
| 50 | N | H₃CS | CH | CH | CH | CH₂ | CN | 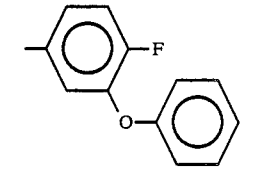 | |
| 51 | N | H₃CS | CH | CH | CH | O | H | 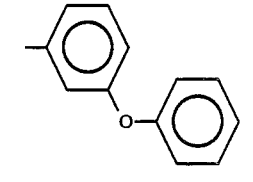 | |
| 52 | N | H₃CS | CH | CH | CH | O | H | 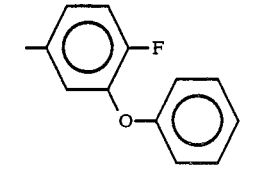 | |
| 53 | N | H₃CS | CH | CH | CH | O | H | 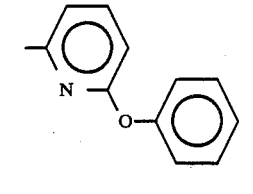 | |
| 54 | N | H₃CS | CH | CH | CH | O | CN | 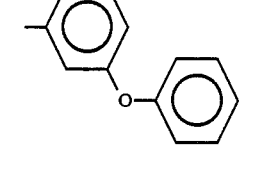 | |
| 55 | N | H₃CS | CH | CH | CH | O | CH₃ | 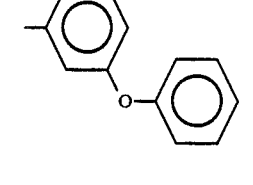 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 56 | CCl | Cl | CH | N | CH | CH₂ | H | 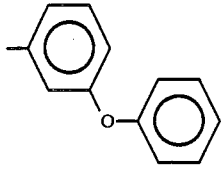 | |
| 57 | CCl | Cl | CH | N | CH | CH₂ | H | 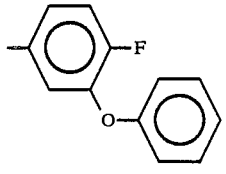 | |
| 58 | CCl | Cl | CH | N | CH | CH₂ | H | 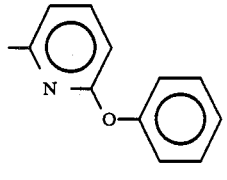 | |
| 59 | CCl | Cl | CH | N | CH | CH₂ | H | 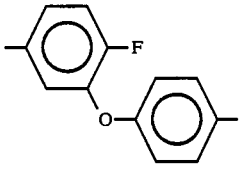 | |
| 60 | CCl | Cl | CH | N | CH | CH₂ | CN | 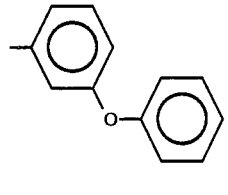 | |
| 61 | CCl | Cl | CH | N | CH | CH₂ | CN | 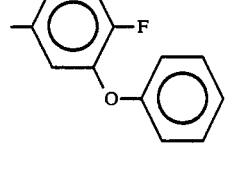 | |
| 62 | CCl | Cl | CH | N | CH | O | H | 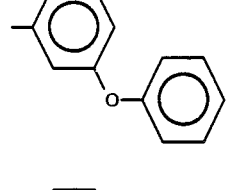 | |
| 63 | CCl | Cl | CH | N | CH | O | H | 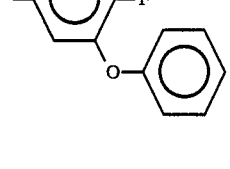 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 64 | CCl | Cl | CH | N | CH | O | H | 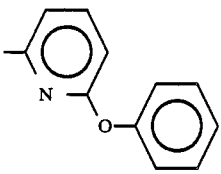 | |
| 65 | CCl | Cl | CH | N | CH | O | CN | 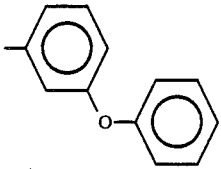 | |
| 66 | CCl | Cl | CH | N | CH | O | CH₃ | 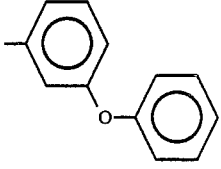 | |
| 67 | CCl | EtO | CH | N | CH | CH₂ | H | 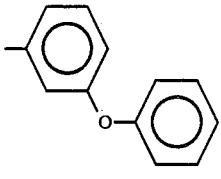 | |
| 68 | CCl | EtO | CH | N | CH | CH₂ | H | 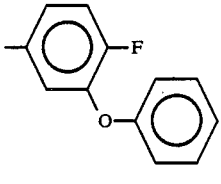 | |
| 69 | CCl | EtO | CH | N | CH | CH₂ | H | 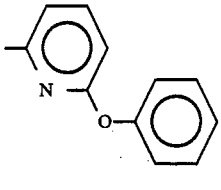 | |
| 70 | CCl | EtO | CH | N | CH | CH₂ | H | 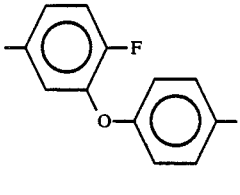 | |
| 71 | CCl | EtO | CH | N | CH | CH₂ | CN | 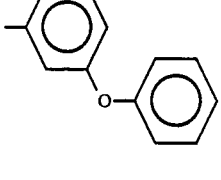 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 72 | CCl | EtO | CH | N | CH | CH₂ | CN | 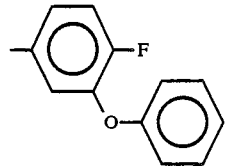 | |
| 73 | CCl | EtO | CH | N | CH | O | H | 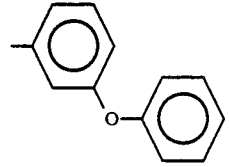 | |
| 74 | CCl | EtO | CH | N | CH | O | H | 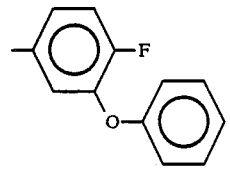 | |
| 75 | CCl | EtO | CH | N | CH | O | H | 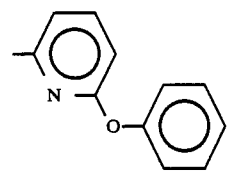 | |
| 76 | CCl | EtO | CH | N | CH | O | CN | 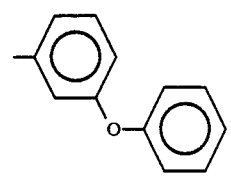 | |
| 77 | CCl | EtO | CH | N | CH | O | CH₃ | 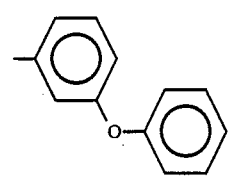 | |
| 78 | CF | EtO | CH | N | CH | CH₂ | H | 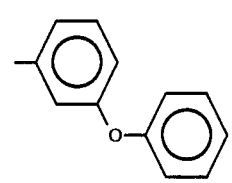 | |
| 79 | CF | EtO | CH | N | CH | CH₂ | H | 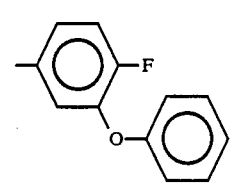 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 80 | CF | EtO | CH | N | CH | CH₂ | H | pyridin-2-yloxy-phenyl | |
| 81 | CF | EtO | CH | N | CH | CH₂ | H | (2-fluorophenoxy)-4-fluorophenyl | |
| 82 | CF | EtO | CH | N | CH | CH₂ | CN | phenoxyphenyl | |
| 83 | CF | EtO | CH | N | CH | CH₂ | CN | (2-fluoro)phenoxyphenyl | |
| 84 | CF | EtO | CH | N | CH | O | H | phenoxyphenyl | |
| 85 | CF | EtO | CH | N | CH | O | H | (2-fluoro)phenoxyphenyl | |
| 86 | CF | EtO | CH | N | CH | O | H | pyridin-2-yloxy-phenyl | |
| 87 | CF | EtO | CH | N | CH | O | CN | phenoxyphenyl | |

TABLE 1-continued $R^2$ and $R^3$ = $CH_3$, A = N, CH or C—$R^1$

| Compound No. | A | $R^1$ | B | C' | D | X | $R^4$ | $R^5$ | Physical data |
|---|---|---|---|---|---|---|---|---|---|
| 88 | CF | EtO | CH | N | CH | O | $CH_3$ | 4-phenoxyphenyl | |
| 89 | | C—O—$CH_2$—O | CH | N | CH | $CH_2$ | H | 4-phenoxyphenyl | |
| 90 | | C—O—$CH_2$—O | CH | N | CH | $CH_2$ | H | 2-fluoro-4-phenoxyphenyl | |
| 91 | | C—O—$CH_2$—O | CH | N | CH | $CH_2$ | H | 6-phenoxypyridin-3-yl | |
| 92 | | C—O—$CH_2$—O | CH | N | CH | $CH_2$ | H | 2-fluoro-4-(4-fluorophenoxy)phenyl | |
| 93 | | C—O—$CH_2$—O | CH | N | CH | $CH_2$ | CN | 4-phenoxyphenyl | |
| 94 | | C—O—$CH_2$—O | CH | N | CH | $CH_2$ | CN | 2-fluoro-4-phenoxyphenyl | |
| 95 | | C—O—$CH_2$—O | CH | N | CH | O | H | 4-phenoxyphenyl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 96 | | C—O—CH₂—O | CH | N | CH | O | H | 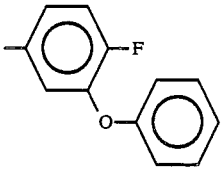 | |
| 97 | | C—O—CH₂—O | CH | N | CH | O | H | 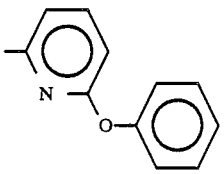 | |
| 98 | | C—O—CH₂—O | CH | N | CH | O | CN | 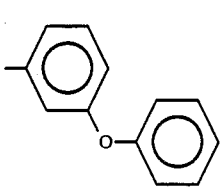 | |
| 99 | | C—O—CH₂—O | CH | N | CH | O | CH₃ | 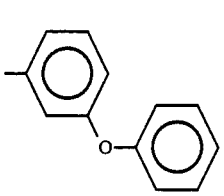 | |
| 100 | CH | EtO | N | CH | CH | CH₂ | H | 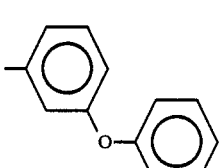 | b.p₀.₀₄ = 230–245° C. |
| 101 | CH | EtO | N | CH | CH | CH₂ | H | 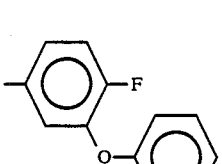 | |
| 102 | CH | EtO | N | CH | CH | CH₂ | H | 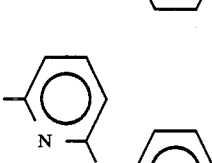 | |
| 103 | CH | EtO | N | CH | CH | CH₂ | H | 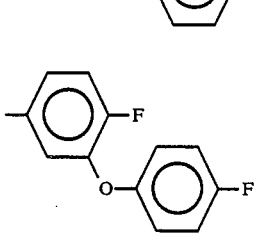 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 104 | CH | EtO | N | CH | CH | CH₂ | CN | (phenoxyphenyl) | |
| 105 | CH | EtO | N | CH | CH | CH₂ | CN | (fluorophenoxyphenyl) | |
| 106 | CH | EtO | N | CH | CH | O | H | (phenoxyphenyl) | |
| 107 | CH | EtO | N | CH | CH | O | H | (fluorophenoxyphenyl) | |
| 108 | CH | EtO | N | CH | CH | O | H | (pyridyloxyphenyl) | |
| 109 | CH | EtO | N | CH | CH | O | CN | (phenoxyphenyl) | |
| 110 | CH | EtO | N | CH | CH | O | CH₃ | (phenoxyphenyl) | |
| 111 | CH | Cl | N | CH | CH | CH₂ | H | (phenoxyphenyl) | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 112 | CH | Cl | N | CH | CH | CH₂ | H | 2-fluoro-phenoxyphenyl | |
| 113 | CH | Cl | N | CH | CH | CH₂ | H | pyridinyloxyphenyl | |
| 114 | CH | Cl | N | CH | CH | CH₂ | H | 2-fluoro-4'-fluoro-phenoxyphenyl | |
| 115 | CH | Cl | N | CH | CH | CH₂ | CN | phenoxyphenyl | |
| 116 | CH | Cl | N | CH | CH | CH₂ | CN | 2-fluoro-phenoxyphenyl | |
| 117 | CH | Cl | N | CH | CH | O | H | phenoxyphenyl | |
| 118 | CH | Cl | N | CH | CH | O | H | 2-fluoro-phenoxyphenyl | |
| 119 | CH | Cl | N | CH | CH | O | H | pyridinyloxyphenyl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 120 | CH | Cl | N | CH | CH | O | CN | 4-phenoxyphenyl | |
| 121 | CH | Cl | N | CH | CH | O | CH₃ | 4-phenoxyphenyl | |
| 122 | CH | H₃CO | N | CH | CH | CH₂ | H | 4-phenoxyphenyl | |
| 123 | CH | H₃CO | N | CH | CH | CH₂ | H | 2-fluoro-4-phenoxyphenyl | |
| 124 | CH | H₃CO | N | CH | CH | CH₂ | H | 6-methyl-2-phenoxypyridin-3-yl | |
| 125 | CH | H₃CO | N | CH | CH | CH₂ | H | 2-fluoro-4-(4-fluorophenoxy)phenyl | |
| 126 | CH | H₃CO | N | CH | CH | CH₂ | CN | 4-phenoxyphenyl | |
| 127 | CH | H₃CO | N | CH | CH | CH₂ | CN | 2-fluoro-4-phenoxyphenyl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 128 | CH | H₃CO | N | CH | CH | O | H | 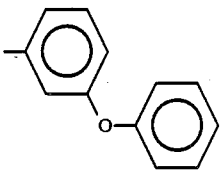 | |
| 129 | CH | H₃CO | N | CH | CH | O | H | 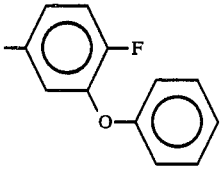 | |
| 130 | CH | H₃CO | N | CH | CH | O | H | 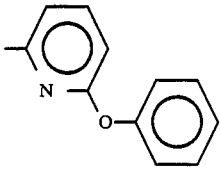 | |
| 131 | CH | H₃CO | N | CH | CH | O | CN | 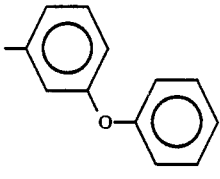 | |
| 132 | CH | H₃CO | N | CH | CH | O | CH₃ | 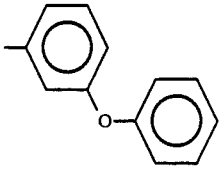 | |
| 133 | CH | EtS | N | CH | CH | CH₂ | H | 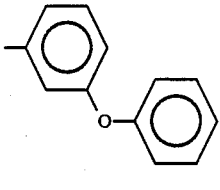 | |
| 134 | CH | EtS | N | CH | CH | CH₂ | H | 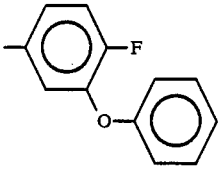 | |
| 135 | CH | EtS | N | CH | CH | CH₂ | H | 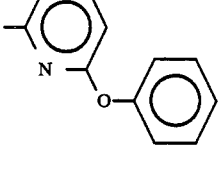 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 136 | CH | EtS | N | CH | CH | CH₂ | H | 2-F,4-(4-F-phenoxy)phenyl | |
| 137 | CH | EtS | N | CH | CH | CH₂ | CN | phenoxyphenyl | |
| 138 | CH | EtS | N | CH | CH | CH₂ | CN | 2-F-4-phenoxyphenyl | |
| 139 | CH | EtS | N | CH | CH | O | H | phenoxyphenyl | |
| 140 | CH | EtS | N | CH | CH | O | H | 2-F-4-phenoxyphenyl | |
| 141 | CH | EtS | N | CH | CH | O | H | 6-(phenoxy)pyridin-3-yl | |
| 142 | CH | EtS | N | CH | CH | O | CN | phenoxyphenyl | |
| 143 | CH | EtS | N | CH | CH | O | CH₃ | phenoxyphenyl | |

TABLE 1-continued
$R^2$ and $R^3 = CH_3$, $A = N$, $CH$ or $C-R^1$
| Compound No. | A | $R^1$ | B | C' | D | X | $R^4$ | $R^5$ | Physical data |
|---|---|---|---|---|---|---|---|---|---|
| 144 | CH | $F_2CHO$ | N | CH | CH | $CH_2$ | H | 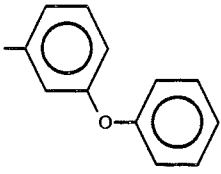 | |
| 145 | CH | $F_2CHO$ | N | CH | CH | $CH_2$ | H | 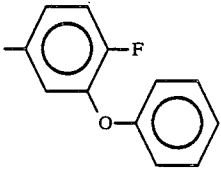 | |
| 146 | CH | $F_2CHO$ | N | CH | CH | $CH_2$ | H | 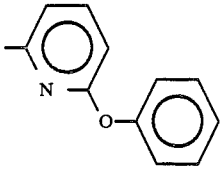 | |
| 147 | CH | $F_2CHO$ | N | CH | CH | $CH_2$ | H | 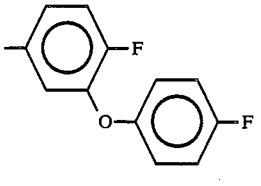 | |
| 148 | CH | $F_2CHO$ | N | CH | CH | $CH_2$ | CN | 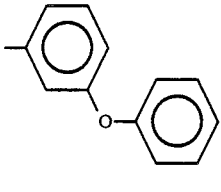 | |
| 149 | CH | $F_2CHO$ | N | CH | CH | $CH_2$ | CN | 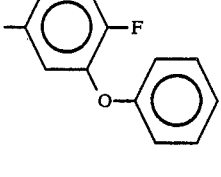 | |
| 150 | CH | $F_2CHO$ | N | CH | CH | O | H | 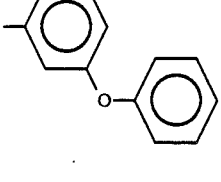 | |
| 151 | CH | $F_2CHO$ | N | CH | CH | O | H | 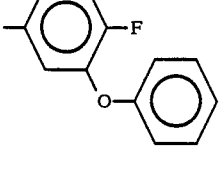 | |

TABLE 1-continued
| | R² and R³ = CH₃, A = N, CH or C—R¹ | | | | | | | | |
|---|---|---|---|---|---|---|---|---|---|
| Compound No. | A | R¹ | B | C' | D | X | R⁴ | R⁵ | Physical data |
| 152 | CH | F₂CHO | N | CH | CH | O | H | 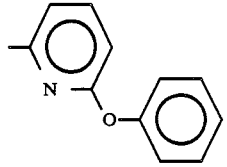 | |
| 153 | CH | F₂CHO | N | CH | CH | O | CN | 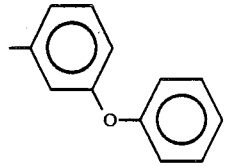 | |
| 154 | CH | F₂CHO | N | CH | CH | O | CH₃ | 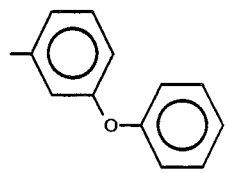 | |
| 155 | CCl | Cl | N | CH | CH | CH₂ | H | 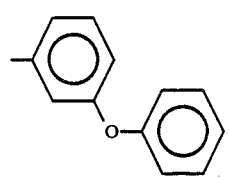 | |
| 156 | CCl | Cl | N | CH | CH | CH₂ | H | 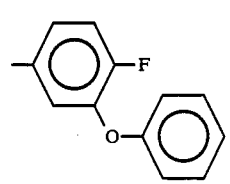 | |
| 157 | CCl | Cl | N | CH | CH | CH₂ | H | 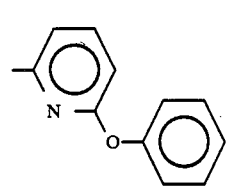 | |
| 158 | CCl | Cl | N | CH | CH | CH₂ | H | 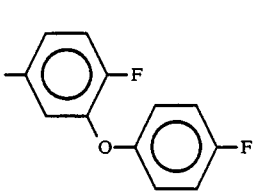 | |
| 159 | CCl | Cl | N | CH | CH | CH₂ | CN | 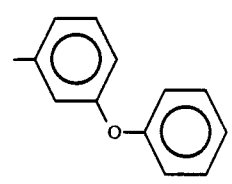 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 160 | CCl | Cl | N | CH | CH | CH₂ | CN | 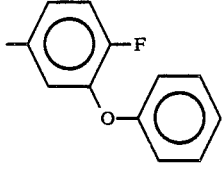 | |
| 161 | CCl | Cl | N | CH | CH | O | H | 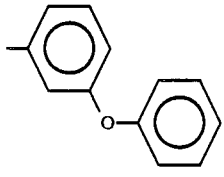 | |
| 162 | CCl | Cl | N | CH | CH | O | H | 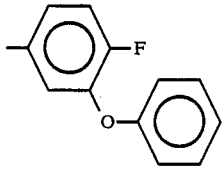 | |
| 163 | CCl | Cl | N | CH | CH | O | H | 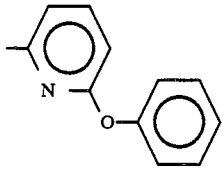 | |
| 164 | CCl | Cl | N | CH | CH | O | CN | 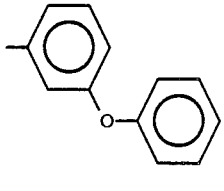 | |
| 165 | CCl | Cl | N | CH | CH | O | CH₃ | 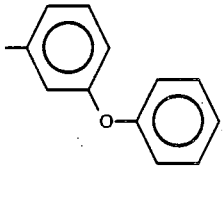 | |
| 166 | CCl | EtO | N | CH | CH | CH₂ | H | 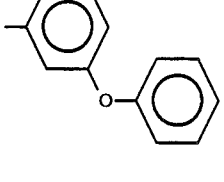 | |
| 167 | CCl | EtO | N | CH | CH | CH₂ | H | 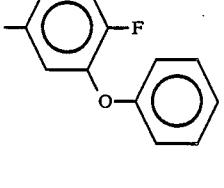 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 168 | CCl | EtO | N | CH | CH | CH₂ | H | pyridine-O-phenyl | |
| 169 | CCl | EtO | N | CH | CH | CH₂ | H | (2-F-phenyl)-O-(4-F-phenyl) | |
| 170 | CCl | EtO | N | CH | CH | CH₂ | CN | phenyl-O-phenyl | |
| 171 | CCl | EtO | N | CH | CH | CH₂ | CN | (2-F-phenyl)-O-phenyl | |
| 172 | CCl | EtO | N | CH | CH | O | H | phenyl-O-phenyl | |
| 173 | CCl | EtO | N | CH | CH | O | H | (2-F-phenyl)-O-phenyl | |
| 174 | CCl | EtO | N | CH | CH | O | H | pyridine-O-phenyl | |
| 175 | CCl | EtO | N | CH | CH | O | CN | phenyl-O-phenyl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 176 | CCl | EtO | N | CH | CH | O | CH₃ | 4-phenoxyphenyl | |
| 177 | | C—O—CH₂—O | N | CH | CH | CH₂ | H | 4-phenoxyphenyl | |
| 178 | | C—O—CH₂—O | N | CH | CH | CH₂ | H | 3-fluoro-4-phenoxyphenyl | |
| 179 | | C—O—CH₂—O | N | CH | CH | CH₂ | H | 6-phenoxypyridin-3-yl | |
| 180 | | C—O—CH₂—O | N | CH | CH | CH₂ | H | 3-fluoro-4-(4-fluorophenoxy)phenyl | |
| 181 | | C—O—CH₂—O | N | CH | CH | CH₂ | CN | 4-phenoxyphenyl | |
| 182 | | C—O—CH₂—O | N | CH | CH | CH₂ | CN | 3-fluoro-4-phenoxyphenyl | |
| 183 | | C—O—CH₂—O | N | CH | CH | O | H | 4-phenoxyphenyl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 184 | | C—O—CH₂—O | N | CH | CH | O | H | 2-fluoro-phenoxyphenyl | |
| 185 | | C—O—CH₂—O | N | CH | CH | O | H | pyridin-2-yloxyphenyl | |
| 186 | | C—O—CH₂—O | N | CH | CH | O | CN | phenoxyphenyl | |
| 187 | | C—O—CH₂—O | N | CH | CH | O | CH₃ | phenoxyphenyl | |
| 188 | | C—O—CH₂—O | CH | CH | N | CH₂ | H | phenoxyphenyl | |
| 189 | | C—O—CH₂—O | CH | CH | N | CH₂ | H | 2-fluoro-phenoxyphenyl | |
| 190 | | C—O—CH₂—O | CH | CH | N | CH₂ | H | pyridin-2-yloxyphenyl | |
| 191 | | C—O—CH₂—O | CH | CH | N | CH₂ | H | 2-fluoro-(4-fluorophenoxy)phenyl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 192 | | C—O—CH₂—O | CH | CH | N | CH₂ | CN | 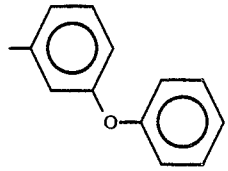 | |
| 193 | | C—O—CH₂—O | CH | CH | N | CH₂ | CN | 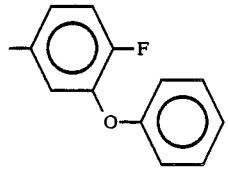 | |
| 194 | | C—O—CH₂—O | CH | CH | N | O | H | 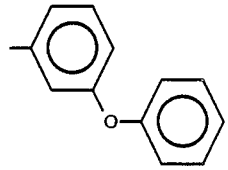 | |
| 195 | | C—O—CH₂—O | CH | CH | N | O | H | 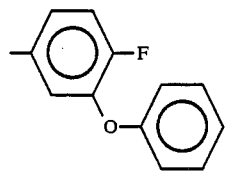 | |
| 196 | | C—O—CH₂—O | CH | CH | N | O | H | 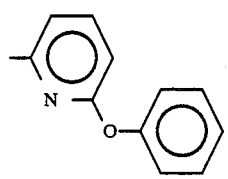 | |
| 197 | | C—O—CH₂—O | CH | CH | N | O | CN | 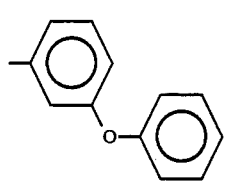 | |
| 198 | | C—O—CH₂—O | CH | CH | N | O | CH₃ | 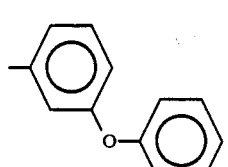 | |
| 199 | N | EtO | CH | N | CH | CH₂ | H | 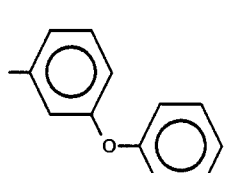 | b.p.$_{0.005}$ = 230–245° C. |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 200 | N | EtO | CH | N | CH | CH₂ | H | (2-fluoro-phenoxy-phenyl) | b.p$_{0.01}$ = 230–240° C. |
| 201 | N | EtO | CH | N | CH | CH₂ | H | (pyridinyl-oxy-phenyl) | |
| 202 | N | EtO | CH | N | CH | CH₂ | H | (2-fluoro-phenoxy-4-fluorophenyl) | |
| 203 | N | EtO | CH | N | CH | CH₂ | CN | (phenoxyphenyl) | |
| 204 | N | EtO | CH | N | CH | CH₂ | CN | (2-fluoro-phenoxy-phenyl) | |
| 205 | N | EtO | CH | N | CH | O | H | (phenoxyphenyl) | b.p$_{0.05}$ = 230–240° C. |
| 206 | N | EtO | CH | N | CH | O | H | (2-fluoro-phenoxy-phenyl) | b.p$_{0.05}$ = 230–235° C. |
| 207 | N | EtO | CH | N | CH | O | H | (pyridinyl-oxy-phenyl) | |

TABLE 1-continued
| | | | R² and R³ = CH₃, A = N, CH or C—R¹ | | | | | | |
|---|---|---|---|---|---|---|---|---|---|
| Compound No. | A | R¹ | B | C' | D | X | R⁴ | R⁵ | Physical data |
| 208 | N | EtO | CH | N | CH | O | CN | 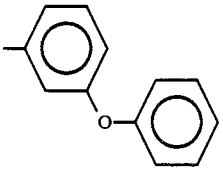 | |
| 209 | N | EtO | CH | N | CH | O | CH₃ | 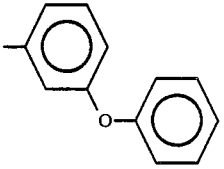 | |
| 210 | N | Cl | CH | N | CH | CH₂ | H | 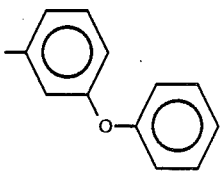 | |
| 211 | N | Cl | CH | N | CH | CH₂ | H | 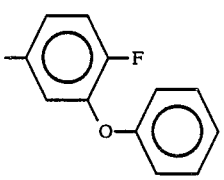 | |
| 212 | N | Cl | CH | N | CH | CH₂ | H | 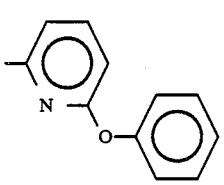 | |
| 213 | N | Cl | CH | N | CH | CH₂ | H | 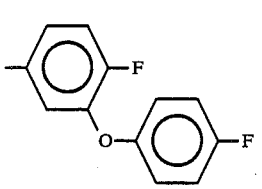 | |
| 214 | N | Cl | CH | N | CH | CH₂ | CN | 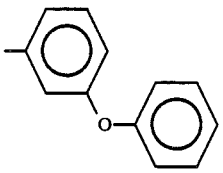 | |
| 215 | N | Cl | CH | N | CH | CH₂ | CN | 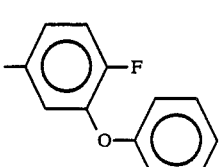 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 216 | N | Cl | CH | N | CH | O | H | 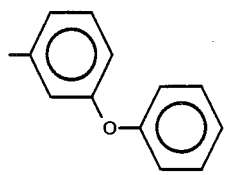 | |
| 217 | N | Cl | CH | N | CH | O | H | 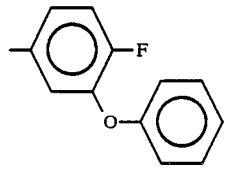 | |
| 218 | N | Cl | CH | N | CH | O | H | 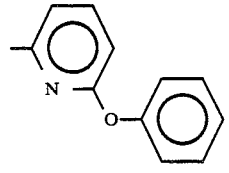 | |
| 219 | N | Cl | CH | N | CH | O | CN | 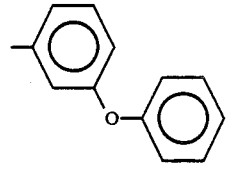 | |
| 220 | N | Cl | CH | N | CH | O | CH₃ | 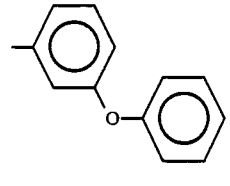 | |
| 221 | N | H₃CO | CH | N | CH | CH₂ | H | 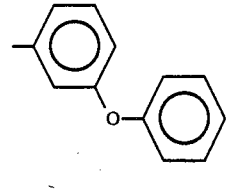 | |
| 222 | N | H₃CO | CH | N | CH | CH₃ | H | 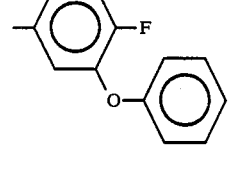 | |
| 223 | N | H₃CO | CH | N | CH | CH₂ | H | 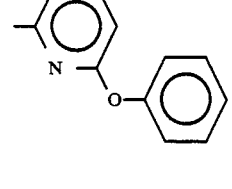 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 224 | N | H₃CO | CH | N | CH | CH₂ | H | 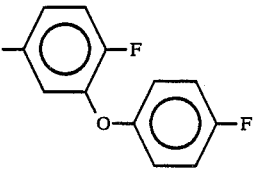 | |
| 225 | N | H₃CO | CH | N | CH | CH₂ | CN | 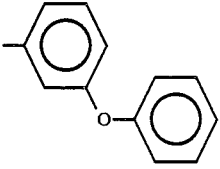 | |
| 226 | N | H₃CO | CH | N | CH | CH₂ | CN | 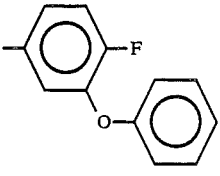 | |
| 227 | N | H₃CO | CH | N | CH | O | H | 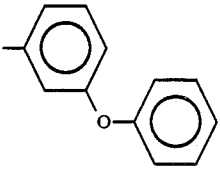 | |
| 228 | N | H₃CO | CH | N | CH | O | H | 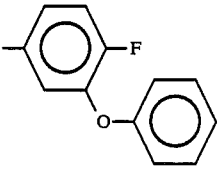 | |
| 229 | N | H₃CO | CH | N | CH | O | H | 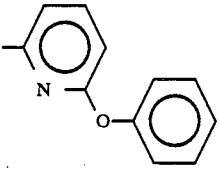 | |
| 230 | N | H₃CO | CH | N | CH | O | CN | 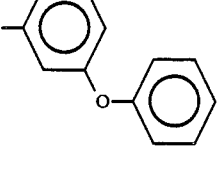 | |
| 231 | N | H₃CO | CH | N | CH | O | CH₃ | 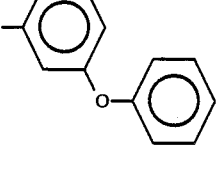 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 232 | N | EtS | CH | N | CH | CH₂ | H | 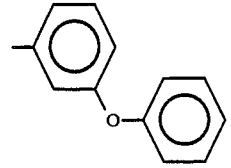 | pale yellow oil |
| 233 | N | EtS | CH | N | CH | CH₂ | H | 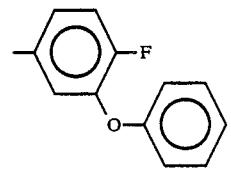 | pale yellow oil |
| 234 | N | EtS | CH | N | CH | CH₂ | H | 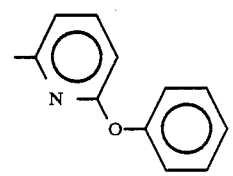 | |
| 235 | N | EtS | CH | N | CH | CH₂ | H | 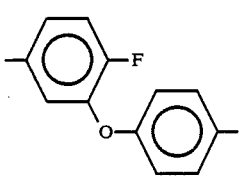 | |
| 236 | N | EtS | CH | N | CH | CH₂ | CN | 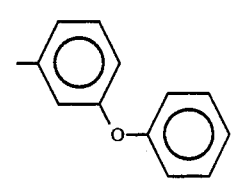 | |
| 237 | N | EtS | CH | N | CH | CH₂ | CN | 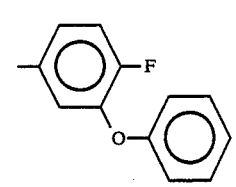 | |
| 238 | N | EtS | CH | N | CH | O | H | 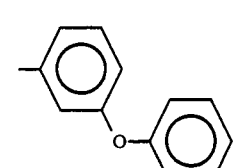 | pale yellow oil |
| 239 | N | EtS | CH | N | CH | O | H | 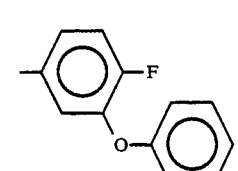 | pale yellow oil |

TABLE 1-continued
| | | | R² and R³ = CH₃, A = N, CH or C—R¹ | | | | | | |
|---|---|---|---|---|---|---|---|---|---|
| Compound No. | A | R¹ | B | C' | D | X | R⁴ | R⁵ | Physical data |
| 240 | N | EtS | CH | N | CH | O | H | 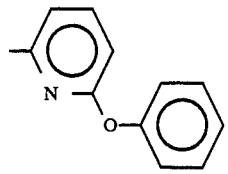 | |
| 241 | N | EtS | CH | N | CH | O | CN | 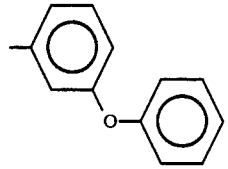 | |
| 242 | N | EtS | CH | N | CH | O | CH₃ | 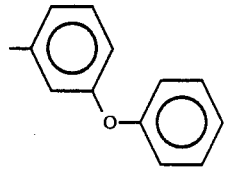 | |
| 243 | N | n-C₃H₇ | CH | N | CH | CH₂ | H | 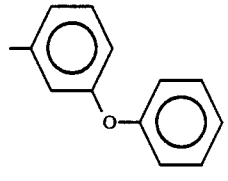 | |
| 244 | N | n-C₃H₇ | CH | N | CH | CH₂ | H | 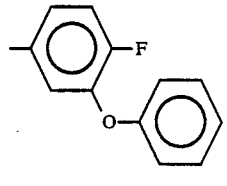 | |
| 245 | N | n-C₃H₇ | CH | N | CH | CH₂ | H | 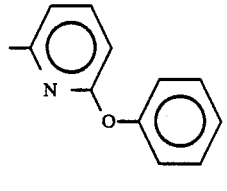 | |
| 247 | N | n-C₃H₇ | CH | N | CH | CH₂ | CN | 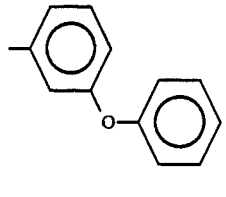 | |
| 248 | N | n-C₃H₇ | CH | N | CH | CH₂ | CN | 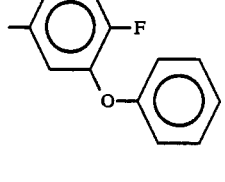 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 249 | N | n-C₃H₇ | CH | N | CH | O | H | 4-(phenoxy)phenyl | |
| 250 | N | n-C₃H₇ | CH | N | CH | O | H | 4-(2-fluorophenoxy)phenyl | |
| 251 | N | n-C₃H₇ | CH | N | CH | O | H | 6-(phenoxy)pyridin-3-yl | |
| 252 | N | n-C₃H₇ | CH | N | CH | O | CN | 4-(phenoxy)phenyl | |
| 253 | N | n-C₃H₇ | CH | N | CH | O | CH₃ | 4-(phenoxy)phenyl | |
| 254 | CH | EtO | N | CH | N | CH₂ | H | 4-(phenoxy)phenyl | b.p$_{0.05}$ = 225–245° C. |
| 255 | CH | EtO | N | CH | N | CH₂ | H | 4-(2-fluorophenoxy)phenyl | |
| 256 | CH | EtO | N | CH | N | CH₂ | H | 6-(phenoxy)pyridin-3-yl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 257 | CH | EtO | N | CH | N | CH₂ | H | 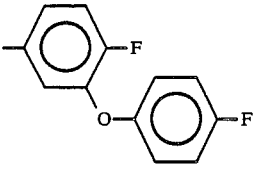 | |
| 258 | CH | EtO | N | CH | N | CH₂ | CN | 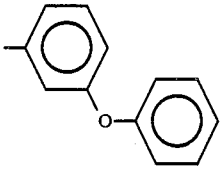 | |
| 259 | CH | EtO | N | CH | N | CH₂ | CN | 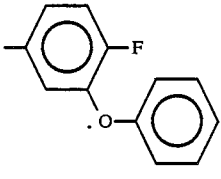 | |
| 260 | CH | EtO | N | CH | N | O | H | 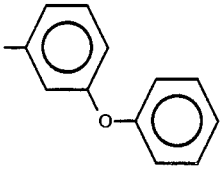 | b.p.$_{0.03}$ = 230° C. |
| 261 | CH | EtO | N | CH | N | O | H | 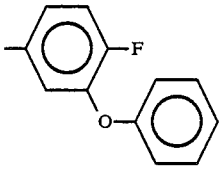 | |
| 262 | CH | EtO | N | CH | N | O | H | 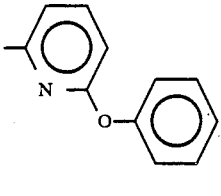 | |
| 263 | CH | EtO | N | CH | N | O | CN | 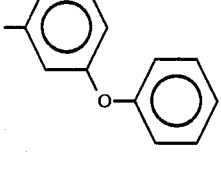 | |
| 264 | CH | EtO | N | CH | N | O | CH₃ | 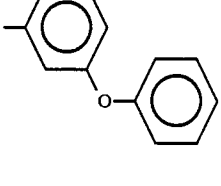 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 265 | CH | Cl | N | CH | N | CH₂ | H | 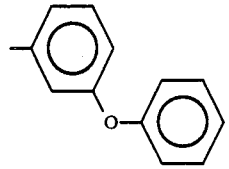 | |
| 266 | CH | Cl | N | CH | N | CH₂ | H | 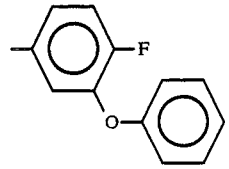 | |
| 267 | CH | Cl | N | CH | N | CH₂ | H | 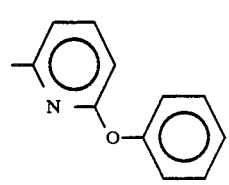 | |
| 268 | CH | Cl | N | CH | N | CH₂ | H | 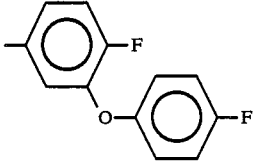 | |
| 269 | CH | Cl | N | CH | N | CH₂ | CN | 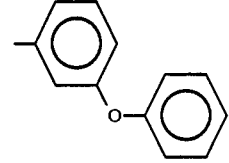 | |
| 270 | CH | Cl | N | CH | N | CH₂ | CN | 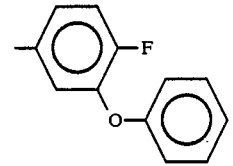 | |
| 271 | CH | Cl | N | CH | N | O | H | 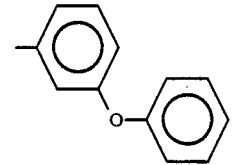 | |
| 272 | CH | Cl | N | CH | N | O | H | 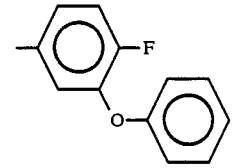 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 273 | CH | Cl | N | CH | N | O | H | 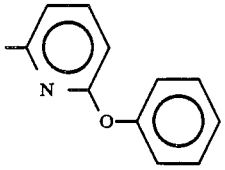 | |
| 274 | CH | Cl | N | CH | N | O | CN | 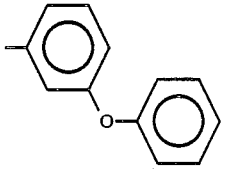 | |
| 275 | CH | Cl | N | CH | N | O | CH₃ | 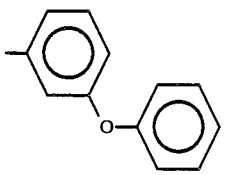 | |
| 276 | CH | H₃CO | N | CH | N | CH₂ | H | 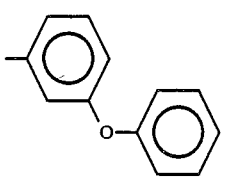 | |
| 277 | CH | H₃CO | N | CH | N | CH₂ | H | 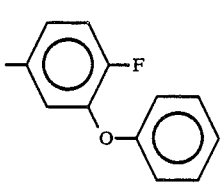 | |
| 278 | CH | H₃CO | N | CH | N | CH₂ | H | 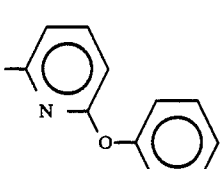 | |
| 279 | CH | H₃CO | N | CH | N | CH₂ | H | 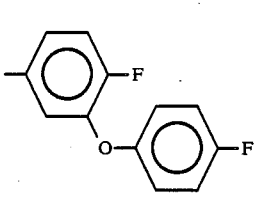 | |
| 280 | CH | H₃CO | N | CH | N | CH₂ | CN | 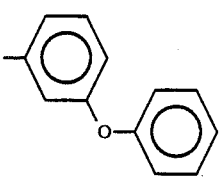 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 281 | CH | H₃CO | N | CH | N | CH₂ | CN | 2-fluoro-phenoxyphenyl | |
| 282 | CH | H₃CO | N | CH | N | O | H | phenoxyphenyl | |
| 283 | CH | H₃CO | N | CH | N | O | H | 2-fluoro-phenoxyphenyl | |
| 284 | CH | H₃CO | N | CH | N | O | H | phenoxypyridyl | |
| 285 | CH | H₃CO | N | CH | N | O | CN | phenoxyphenyl | |
| 286 | CH | H₃CO | N | CH | N | O | CH₃ | phenoxyphenyl | |
| 287 | CH | F₂CHO | N | CH | N | CH₂ | H | phenoxyphenyl | |
| 288 | CH | F₂CHO | N | CH | N | CH₂ | H | 2-fluoro-phenoxyphenyl | |

TABLE 1-continued

| | | | R² and R³ = CH₃, A = N, CH or C—R¹ | | | | | | |
|---|---|---|---|---|---|---|---|---|---|
| Compound No. | A | R¹ | B | C' | D | X | R⁴ | R⁵ | Physical data |
| 289 | CH | F₂CHO | N | CH | N | CH₂ | H | 2-pyridyl-O-phenyl | |
| 290 | CH | F₂CHO | N | CH | N | CH₂ | H | 2-fluorophenyl-O-4-fluorophenyl | |
| 291 | CH | F₂CHO | N | CH | N | CH₂ | CN | phenyl-O-phenyl | |
| 292 | CH | F₂CHO | N | CH | N | CH₂ | CN | 2-fluorophenyl-O-phenyl | |
| 293 | CH | F₂CHO | N | CH | N | O | H | phenyl-O-phenyl | |
| 294 | CH | F₂CHO | N | CH | N | O | H | 2-fluorophenyl-O-phenyl | |
| 295 | CH | F₂CHO | N | CH | N | O | H | 2-pyridyl-O-phenyl | |
| 296 | CH | F₂CHO | N | CH | N | O | CN | phenyl-O-phenyl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 297 | CH | F₂CHO | N | CH | N | O | CH₃ | 4-phenoxyphenyl | |
| 298 | CH | EtS | N | CH | N | CH₂ | H | 4-phenoxyphenyl | |
| 299 | CH | EtS | N | CH | N | CH₂ | H | 2-fluoro-4-phenoxyphenyl | |
| 300 | CH | EtS | N | CH | N | CH₂ | H | 6-phenoxypyridin-2-yl | |
| 301 | CH | EtS | N | CH | N | CH₂ | H | 2-fluoro-4-(4-fluorophenoxy)phenyl | |
| 302 | CH | EtS | N | CH | N | CH₂ | CN | 3-phenoxyphenyl | |
| 303 | CH | EtS | N | CH | N | CH₂ | CN | 2-fluoro-4-phenoxyphenyl | |
| 304 | CH | EtS | N | CH | N | O | H | 3-phenoxyphenyl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 305 | CH | EtS | N | CH | N | O | H | 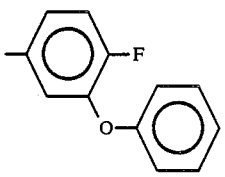 | |
| 306 | CH | EtS | N | CH | N | O | H | 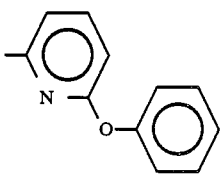 | |
TABLE 1
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 307 | CH | EtS | N | CH | N | O | CN | 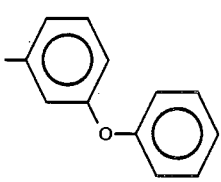 | |
| 308 | CH | EtS | N | CH | N | O | CH₃ | 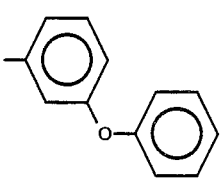 | |
| 309 | N | EtO | CH | CH | N | CH₂ | H | 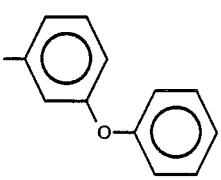 | |
| 310 | N | EtO | CH | CH | N | CH₂ | H | 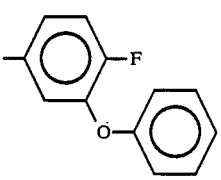 | |
| 311 | N | EtO | CH | CH | N | CH₂ | H | 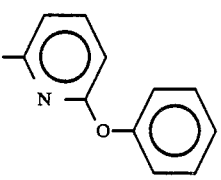 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 312 | N | EtO | CH | CH | N | O | H | 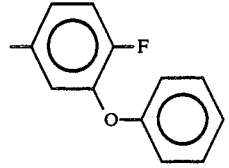 | pale yellow oil |
| 313 | N | EtO | CH | CH | N | O | H | 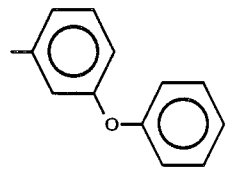 | pale yellow oil |
| 314 | N | Cl | CH | CH | N | CH₂ | H | 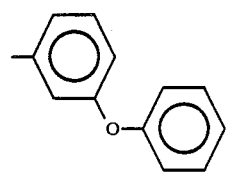 | |
| 315 | N | Cl | CH | CH | N | CH₂ | H | 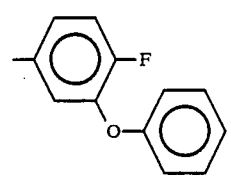 | |
| 316 | N | Cl | CH | CH | N | CH₂ | H | 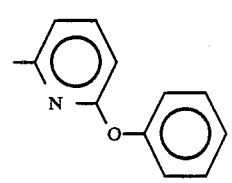 | |
| 317 | N | Cl | CH | CH | N | O | H | 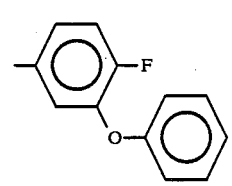 | |
| 318 | N | Cl | CH | CH | N | O | H | 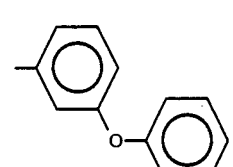 | |
| 319 | N | CH₃O | CH | CH | N | CH₂ | H | 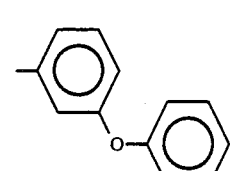 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 320 | N | CH₃O | CH | CH | N | CH₂ | H | 2-fluoro-phenoxyphenyl | |
| 321 | N | CH₃O | CH | CH | N | CH₂ | H | (pyridinyloxy)phenyl | |
| 322 | N | CH₃O | CH | CH | N | O | H | 2-fluoro-phenoxyphenyl | |
| 323 | N | CH₃O | CH | CH | N | O | H | phenoxyphenyl | |
| 324 | N | EtS | CH | CH | N | CH₂ | H | phenoxyphenyl | |
| 325 | N | EtS | CH | CH | N | CH₂ | H | 2-fluoro-phenoxyphenyl | |
| 326 | N | EtS | CH | CH | N | CH₂ | H | (pyridinyloxy)phenyl | |
| 327 | N | EtS | CH | CH | N | O | H | 2-fluoro-phenoxyphenyl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 328 | N | EtS | CH | CH | N | O | H | 4-phenoxyphenyl | |
| 329 | CCl | EtO | N | N | CH | CH₂ | H | 4-phenoxyphenyl | |
| 330 | CCl | EtO | N | N | CH | CH₂ | H | 4-(2-fluorophenoxy)phenyl | |
| 331 | CCl | EtO | N | N | CH | CH₂ | H | 6-phenoxypyridin-2-yl | |
| 332 | CCl | EtO | N | N | CH | O | H | 4-(2-fluorophenoxy)phenyl | |
| 333 | CCl | EtO | N | N | CH | O | H | 4-phenoxyphenyl | |
| 334 | CCl | Cl | N | N | CH | CH₂ | H | 4-phenoxyphenyl | |
| 335 | CCl | Cl | N | N | CH | CH₂ | H | 4-(2-fluorophenoxy)phenyl | |

TABLE 1-continued

| | R² and R³ = CH₃, A = N, CH or C—R¹ | | | | | | | | |
|---|---|---|---|---|---|---|---|---|---|
| Compound No. | A | R¹ | B | C' | D | X | R⁴ | R⁵ | Physical data |
| 336 | CCl | Cl | N | N | CH | CH₂ | H | 6-methylpyridin-2-yl phenyl ether | |
| 337 | CCl | Cl | N | N | CH | O | H | 4-methyl-2-fluorophenyl phenyl ether | |
| 338 | CCl | Cl | N | N | CH | O | H | 3-methylphenyl phenyl ether | |
| 339 | CH | EtO | CH | N | N | CH₂ | H | 3-methylphenyl phenyl ether | |
| 340 | CH | EtO | CH | N | N | CH₂ | H | 4-methyl-2-fluorophenyl phenyl ether | |
| 341 | CH | EtO | CH | N | N | CH₂ | H | 6-methylpyridin-2-yl phenyl ether | |
| 342 | CH | EtO | CH | N | N | O | H | 4-methyl-2-fluorophenyl phenyl ether | pale yellow oil |
| 343 | CH | EtO | CH | N | N | O | H | 3-methylphenyl phenyl ether | pale yellow oil |

TABLE 1-continued

| | R² and R³ = CH₃, A = N, CH or C—R¹ | | | | | | | | |
|---|---|---|---|---|---|---|---|---|---|
| Compound No. | A | R¹ | B | C' | D | X | R⁴ | R⁵ | Physical data |
| 344 | CH | CH₃O | CH | N | N | CH₂ | H | 4-phenoxyphenyl | |
| 345 | CH | CH₃O | CH | N | N | CH₂ | H | 2-fluoro-phenoxyphenyl | |
| 346 | CH | CH₃O | CH | N | N | CH₂ | H | pyridyl-phenoxy | |
| 347 | CH | CH₃O | CH | N | N | O | H | 2-fluoro-phenoxyphenyl | |
| 348 | CH | CH₃O | CH | N | N | O | H | phenoxyphenyl | |
| 349 | CH | Cl | CH | N | N | CH₂ | H | phenoxyphenyl | |
| 350 | CH | Cl | CH | N | N | CH₂ | H | 2-fluoro-phenoxyphenyl | |
| 351 | CH | Cl | CH | N | N | CH₂ | H | pyridyl-phenoxy | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 352 | CH | Cl | CH | N | N | O | H | 2-F-phenoxyphenyl | |
| 353 | CH | Cl | CH | N | N | O | H | phenoxyphenyl | |
| 354 | CH | EtS | CH | N | N | CH₂ | H | phenoxyphenyl | |
| 355 | CH | EtS | CH | N | N | CH₂ | H | 2-F-phenoxyphenyl | |
| 356 | CH | EtS | CH | N | N | CH₂ | H | pyridyloxyphenyl | |
| 357 | CH | EtS | CH | N | N | O | H | 2-F-phenoxyphenyl | pale yellow oil |
| 358 | CH | EtS | CH | N | N | O | H | phenoxyphenyl | pale yellow oil |
| 359 | CCl | Cl | CH | N | N | CH₂ | H | phenoxyphenyl | |

TABLE 1-continued $R^2$ and $R^3$ = $CH_3$, A = N, CH or C—$R^1$

| Compound No. | A | $R^1$ | B | C' | D | X | $R^4$ | $R^5$ | Physical data |
|---|---|---|---|---|---|---|---|---|---|
| 360 | CCl | Cl | CH | N | N | $CH_2$ | H | 2-fluoro-4-phenoxyphenyl | |
| 361 | CCl | Cl | CH | N | N | $CH_2$ | H | 6-phenoxypyridin-2-yl | |
| 362 | CCl | Cl | CH | N | N | O | H | 2-fluoro-4-phenoxyphenyl | |
| 363 | CCl | Cl | CH | N | N | O | H | 4-phenoxyphenyl | |
| 364 | CH | EtO | N | N | N | $CH_2$ | H | 4-phenoxyphenyl | |
| 365 | CH | EtO | N | N | N | $CH_2$ | H | 2-fluoro-4-phenoxyphenyl | |
| 366 | CH | EtO | N | N | N | $CH_2$ | H | 6-phenoxypyridin-2-yl | |
| 367 | CH | EtO | N | N | N | O | H | 2-fluoro-4-phenoxyphenyl | |

TABLE 1-continued

| Compound No. | A | R¹ | B | C' | D | X | R⁴ | R⁵ | Physical data |
|---|---|---|---|---|---|---|---|---|---|
| 368 | CH | EtO | N | N | N | O | H | 4-(phenoxy)phenyl | |
| 369 | CH | CH₃O | N | N | N | CH₂ | H | 4-(phenoxy)phenyl | |
| 370 | CH | CH₃O | N | N | N | CH₂ | H | 3-fluoro-4-phenoxyphenyl | |
| 371 | CH | CH₃O | N | N | N | CH₂ | H | 6-phenoxypyridin-3-yl | |
| 372 | CH | CH₃O | N | N | N | O | H | 3-fluoro-4-phenoxyphenyl | |
| 373 | CH | CH₃O | N | N | N | O | H | 3-phenoxyphenyl | |
| 374 | CH | Cl | N | N | N | CH₂ | H | 3-phenoxyphenyl | |
| 375 | CH | Cl | N | N | N | CH₂ | H | 3-fluoro-4-phenoxyphenyl | |

R² and R³ = CH₃, A = N, CH or C—R¹

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 376 | CH | Cl | N | N | N | CH₂ | H | 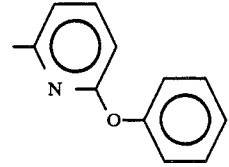 | |
| 377 | CH | Cl | N | N | N | O | H | 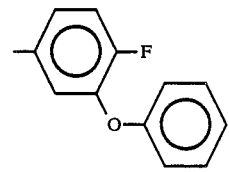 | |
| 378 | CH | Cl | N | N | N | O | H | 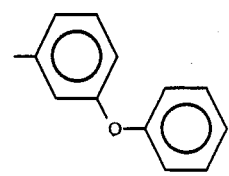 | |
| 379 | CH | EtS | N | N | N | CH₂ | H | 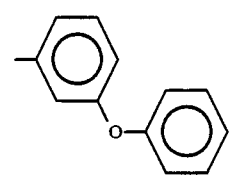 | |
| 380 | CH | EtS | N | N | N | CH₂ | H | 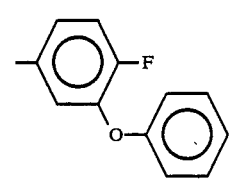 | |
| 381 | CH | EtS | N | N | N | CH₂ | H | 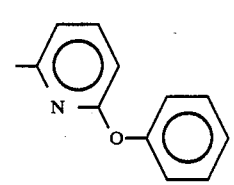 | |
| 382 | CH | EtS | N | N | N | O | H | 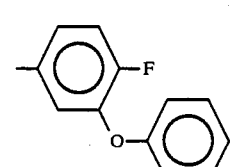 | |
| 383 | CH | EtS | N | N | N | O | H | 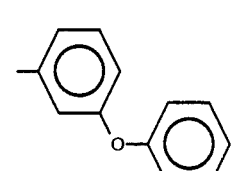 | |

TABLE 1-continued
$R^2$ and $R^3$ = $CH_3$, A = N, CH or C—$R^1$
| Compound No. | A | $R^1$ | B | C' | D | X | $R^4$ | $R^5$ | Physical data |
|---|---|---|---|---|---|---|---|---|---|
| 384 | N | EtS | N | N | N | $CH_2$ | H | 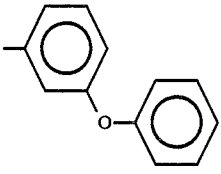 | |
| 385 | N | EtO | N | N | CH | $CH_2$ | H | 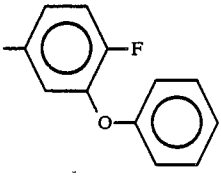 | |
| 386 | N | EtO | N | N | CH | $CH_2$ | H | 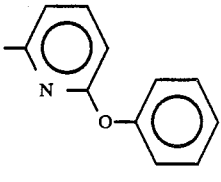 | |
| 387 | N | EtO | N | N | N | O | H | 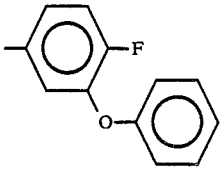 | |
| 388 | N | EtO | N | N | CH | O | H | 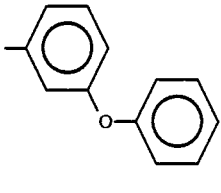 | |
| 389 | N | $CH_3O$ | N | N | CH | $CH_2$ | H | 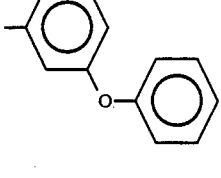 | |
| 390 | N | $CH_3O$ | N | N | CH | $CH_2$ | H | 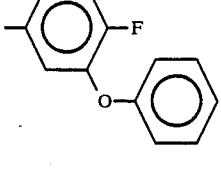 | |
| 391 | N | $CH_3O$ | N | N | CH | $CH_2$ | H | 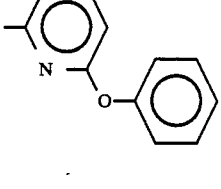 | |

TABLE 1-continued
$R^2$ and $R^3$ = $CH_3$, A = N, CH or C—$R^1$
| Compound No. | A | $R^1$ | B | C' | D | X | $R^4$ | $R^5$ | Physical data |
|---|---|---|---|---|---|---|---|---|---|
| 392 | N | CH$_3$O | N | N | CH | O | H | 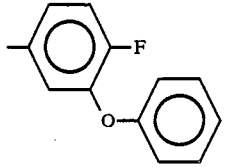 | |
| 393 | N | CH$_3$O | N | N | CH | O | H | 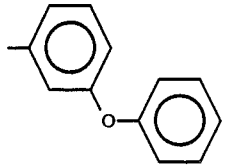 | |
| 394 | N | Cl | N | N | CH | CH$_2$ | H | 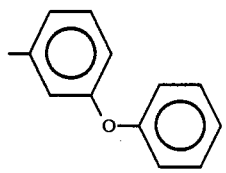 | |
| 395 | N | Cl | N | N | CH⁻ | CH$_2$ | H | 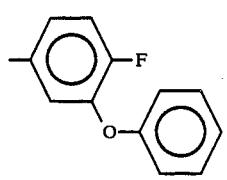 | |
| 396 | N | Cl | N | N | CH | CH$_2$ | H | 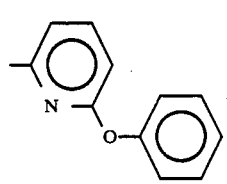 | |
| 397 | N | Cl | N | N | CH | O | H | 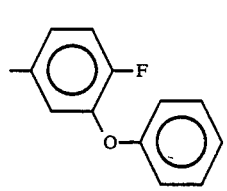 | |
| 398 | N | Cl | N | N | CH | O | H | 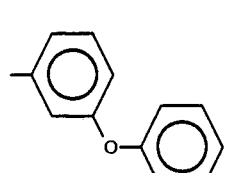 | |
| 399 | N | EtS | N | N | CH | CH$_2$ | H | 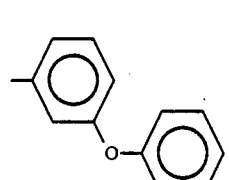 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 400 | N | EtS | N | N | CH | CH₂ | H | 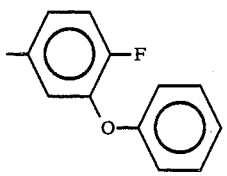 | |
| 401 | N | EtS | N | N | CH | CH₂ | H | 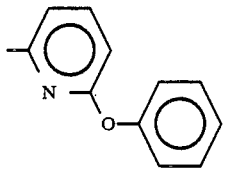 | |
| 402 | N | EtS | N | N | CH | O | H | 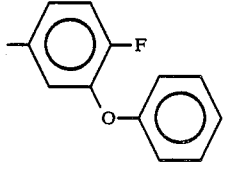 | |
| 403 | N | EtS | N | N | CH | O | H | 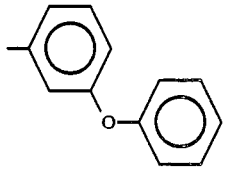 | |
| 404 | N | EtO | N | N | N | CH₂ | H | 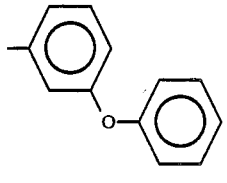 | |
| 405 | N | EtO | N | N | N | CH₂ | H | 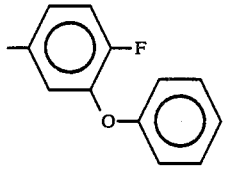 | |
| 406 | N | EtO | N | N | N | CH₂ | H | 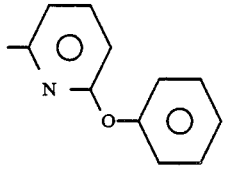 | |
| 407 | N | EtO | N | N | N | O | H | 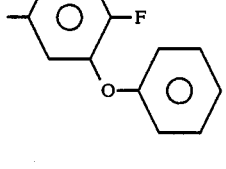 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 408 | N | EtO | N | N | N | O | H | phenoxyphenyl | |
| 409 | N | CH₃O | N | N | N | CH₂ | H | phenoxyphenyl | |
| 410 | N | CH₃O | N | N | N | CH₂ | H | fluoro-phenoxyphenyl | |
| 411 | N | CH₃O | N | N | N | CH₂ | H | pyridyloxyphenyl | |
| 412 | N | CH₃O | N | N | N | O | H | fluoro-phenoxyphenyl | |
| 413 | N | CH₃O | N | N | N | O | H | phenoxyphenyl | |
| 414 | N | Cl | N | N | N | CH₂ | H | phenoxyphenyl | |
| 415 | N | Cl | N | N | N | CH₂ | H | fluoro-phenoxyphenyl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 416 | N | Cl | N | N | N | CH₂ | H | (pyridinyl-O-phenyl) | |
| 417 | N | Cl | N | N | N | O | H | (fluorophenyl-O-phenyl) | |
| 418 | N | Cl | N | N | N | O | H | (phenyl-O-phenyl) | |
| 419 | N | EtS | N | N | N | CH₂ | H | (phenyl-O-phenyl) | |
| 420 | N | EtS | N | N | N | CH₂ | H | (fluorophenyl-O-phenyl) | |
| 421 | N | EtS | N | N | N | CH₂ | H | (pyridinyl-O-phenyl) | |
| 422 | N | EtS | N | N | N | O | H | (fluorophenyl-O-phenyl) | |
| 423 | N | EtS | N | N | N | O | H | (phenyl-O-phenyl) | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 424 | N | F₃C—CH₂—O— | CH | CH | CH | CH₂ | H | (2-phenoxyphenyl, methyl-substituted) | b.p 0.01 = 225–235° C. |
| 425 | N | F₃C—CH₂—O— | CH | CH | CH | CH₂ | H | (fluoro-phenoxyphenyl, methyl-substituted) | b.p 0.01 = 230–235° C. |
| 426 | N | F₃C—CH₂—O— | CH | CH | CH | CH₂ | H | (phenoxy-pyridyl, methyl-substituted) | |
| 427 | N | F₃C—CH₂—O— | CH | CH | CH | CH₂ | H | (phenoxy-thienyl, methyl-substituted) | |
| 428 | N | F₃C—CH₂—O— | CH | CH | CH | CH₂ | H | (fluoro-phenoxy-fluorophenyl, methyl-substituted) | |
| 429 | N | F₃C—CH₂—O— | CH | CH | CH | O | H | (phenoxyphenyl, methyl-substituted) | b.p 0.02 = 230–240° C. |
| 430 | N | F₃C—CH₂—O— | CH | CH | CH | O | H | (fluoro-phenoxyphenyl, methyl-substituted) | b.p 0.04 = 230–240° C. |
| 431 | N | F₃C—CH₂—O— | CH | CH | CH | O | H | (phenoxy-pyridyl, methyl-substituted) | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 432 | CH | F₃C—CH₂—O— | N | CH | CH | CH₂ | H | phenoxyphenyl (2-methyl) | |
| 433 | CH | F₃C—CH₂—O— | N | CH | CH | CH₂ | H | 2-fluoro-phenoxy-methylphenyl | |
| 434 | CH | F₃C—CH₂—O— | N | CH | CH | CH₂ | H | pyridinyl-oxy-phenyl | |
| 435 | CH | F₃C—CH₂—O— | N | CH | CH | CH₂ | H | thienyl-oxy-phenyl | |
| 436 | CH | F₃C—CH₂—O— | N | CH | CH | CH₂ | H | 2-fluoro-(4-fluorophenoxy)-methylphenyl | |
| 437 | CH | F₃C—CH₂—O— | N | CH | CH | O | H | phenoxyphenyl | |
| 438 | CH | F₃C—CH₂—O— | N | CH | CH | O | H | 2-fluoro-phenoxy-methylphenyl | |
| 439 | CH | F₃C—CH₂—O— | N | CH | CH | O | H | pyridinyl-oxy-phenyl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 440 | N | F₃C—CH₂—O— | CH | N | CH | CH₂ | H | 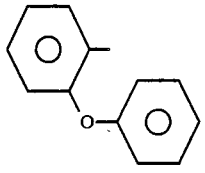 | b.p 0.01 = 240–245° C. |
| 441 | N | F₃C—CH₂—O— | CH | N | CH | CH₂ | H | 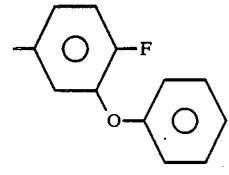 | b.p 0.01 = 240–245° C. |
| 442 | N | F₃C—CH₂—O— | CH | N | CH | CH₂ | H | 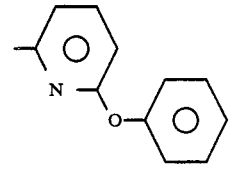 | |
| 443 | N | F₃C—CH₂—O— | CH | N | CH | CH₂ | H | 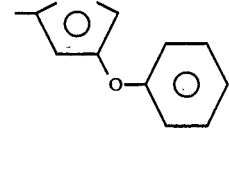 | |
| 444 | N | F₃C—CH₂—O— | CH | N | CH | CH₂ | H | 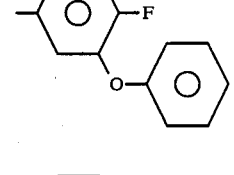 | |
| 445 | N | F₃C—CH₂—O— | CH | N | CH | O | H | 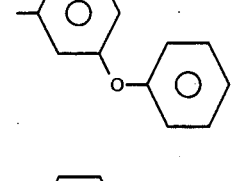 | pale yellow oil |
| 446 | N | F₃C—CH₂—O— | CH | N | CH | O | H | 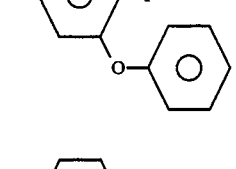 | pale yellow oil |
| 447 | N | F₃C—CH₂—O— | CH | N | CH | O | H | 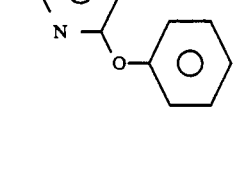 | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 448 | CH | F₃C—CH₂—O— | N | CH | N | CH₂ | H | 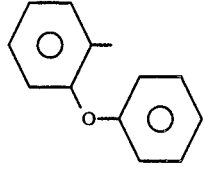 | |
| 449 | CH | F₃C—CH₂—O— | N | CH | N | CH₂ | H | 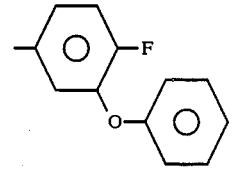 | |
| 450 | CH | F₃C—CH₂—O— | N | CH | N | CH₂ | H | 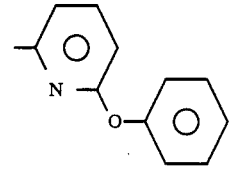 | |
| 451 | CH | F₃C—CH₂—O— | N | CH | N | CH₂ | H | 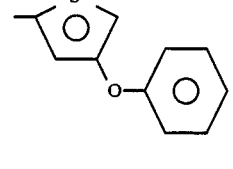 | |
| 452 | CH | F₃C—CH₂—O— | N | CH | N | CH₂ | H | 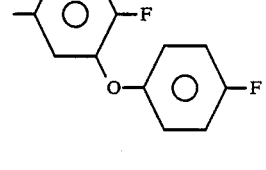 | |
| 453 | CH | F₃C—CH₂—O— | N | CH | N | O | H | 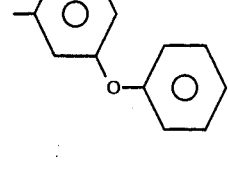 | |
| 454 | CH | F₃C—CH₂—O— | N | CH | N | O | H | 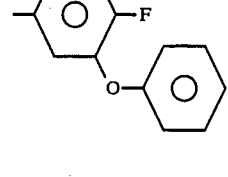 | |
| 455 | CH | F₃C—CH₂—O— | N | CH | N | O | H | 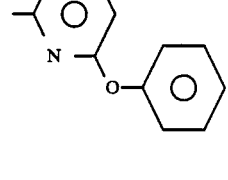 | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 456 | N | F₃C—CH₂—O— | N | CH | CH | CH₂ | H | 2-phenoxyphenyl (methyl-substituted) | pale yellow oil |
| 457 | N | F₃C—CH₂—O— | N | CH | CH | CH₂ | H | 2-phenoxy-3-fluorophenyl (methyl-substituted) | pale yellow oil |
| 458 | N | F₃C—CH₂—O— | N | CH | CH | CH₂ | H | 6-methyl-2-phenoxypyridin-3-yl | |
| 459 | N | F₃C—CH₂—O— | N | CH | CH | CH₂ | H | 3-phenoxythien-2-yl | |
| 460 | N | F₃C—CH₂—O— | N | CH | CH | CH₂ | H | 2-(4-fluorophenoxy)-3-fluorophenyl (methyl-substituted) | |
| 461 | N | F₃C—CH₂—O— | N | CH | CH | O | H | 3-phenoxyphenyl (methyl-substituted) | pale yellow oil |
| 462 | N | F₃C—CH₂—O— | N | CH | CH | O | H | 2-phenoxy-3-fluorophenyl (methyl-substituted) | pale yellow oil |
| 463 | N | F₃C—CH₂—O— | N | CH | CH | O | H | 6-methyl-2-phenoxypyridin-3-yl | |

TABLE 1-continued

R² and R³ = CH₃, A = N, CH or C—R¹

| Compound No. | A | R¹ | B | C' | D | X | R⁴ | R⁵ | Physical data |
|---|---|---|---|---|---|---|---|---|---|
| 464 | N | F₃C—CH₂—O— | CH | CH | N | CH₂ | H | phenoxyphenyl | pale yellow oil |
| 465 | N | F₃C—CH₂—O— | CH | CH | N | CH₂ | H | (2-fluoro)phenoxyphenyl | pale yellow oil |
| 466 | N | F₃C—CH₂—O— | CH | CH | N | CH₂ | H | pyridinyl-O-phenyl | |
| 467 | N | F₃C—CH₂—O— | CH | CH | N | CH₂ | H | thienyl-O-phenyl | |
| 468 | N | F₃C—CH₂—O— | CH | CH | N | CH₂ | H | (2-fluoro)phenoxy-(4-fluoro)phenyl | |
| 469 | N | F₃C—CH₂—O— | CH | CH | N | O | H | phenoxyphenyl | pale yellow oil |
| 470 | N | F₃C—CH₂—O— | CH | CH | N | O | H | (2-fluoro)phenoxyphenyl | pale yellow oil |
| 471 | N | F₃C—CH₂—O— | CH | CH | N | O | H | pyridinyl-O-phenyl | |

TABLE 1-continued
R² and R³ = CH₃, A = N, CH or C—R¹
| Compound No. | A | R¹ | B | C' | D | X | R⁴ | R⁵ | Physical data |
|---|---|---|---|---|---|---|---|---|---|
| 472 | N | F₃C—CH₂—O— | N | N | CH | CH₂ | H | 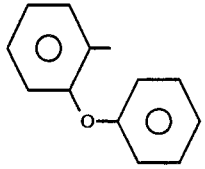 | |
| 473 | N | F₃C—CH₂—O— | N | N | CH | CH₂ | H | 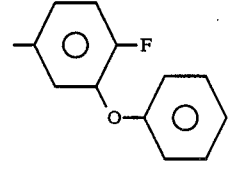 | |
| 474 | N | F₃C—CH₂—O— | N | N | CH | CH₂ | H | 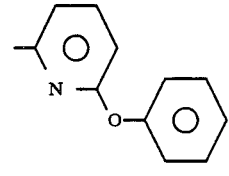 | |
| 475 | N | F₃C—CH₂—O— | N | N | CH | CH₂ | H | 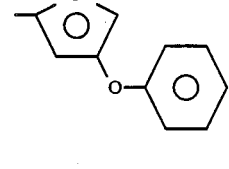 | |
| 476 | N | F₃C—CH₂—O— | N | N | CH | CH₂ | H | 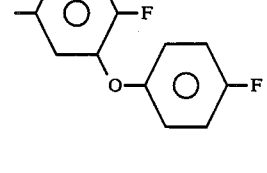 | |
| 477 | N | F₃C—CH₂—O— | N | N | CH | O | H | 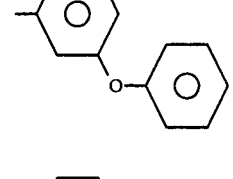 | |
| 478 | N | F₃C—CH₂—O— | N | N | CH | O | H | 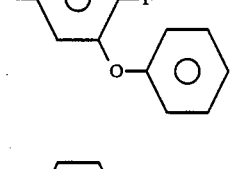 | |
| 479 | N | F₃C—CH₂—O— | N | N | CH | O | H | 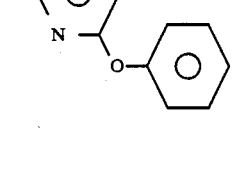 | |

TABLE 1-continued

| | | R² and R³ = CH₃, A = N, CH or C—R¹ | | | | | | | |
|---|---|---|---|---|---|---|---|---|---|
| Compound No. | A | R¹ | B | C' | D | X | R⁴ | R⁵ | Physical data |
| 480 | N | F₃C—CH₂—O— | N | CH | N | CH₂ | H | (2-phenoxyphenyl) | |
| 481 | N | F₃C—CH₂—O— | N | CH | N | CH₂ | H | (2-fluoro-phenoxyphenyl) | |
| 482 | N | F₃C—CH₂—O— | N | CH | N | CH₂ | H | (pyridinyl-oxyphenyl) | |
| 483 | N | F₃C—CH₂—O— | N | CH | N | CH₂ | H | (thienyl-oxyphenyl) | |
| 484 | N | F₃C—CH₂—O— | N | CH | N | CH₂ | H | (2-fluoro-4-fluorophenoxyphenyl) | |
| 485 | N | F₃C—CH₂—O— | N | CH | N | O | H | (phenoxyphenyl) | |
| 486 | N | F₃C—CH₂—O— | N | CH | N | O | H | (2-fluoro-phenoxyphenyl) | |
| 487 | N | F₃C—CH₂—O— | N | CH | N | O | H | (pyridinyl-oxyphenyl) | |

TABLE 1-continued
$R^2$ and $R^3$ = $CH_3$, A = N, CH or C—$R^1$
| Compound No. | A | $R^1$ | B | C' | D | X | $R^4$ | $R^5$ | Physical data |
|---|---|---|---|---|---|---|---|---|---|
| 488 | N | $F_3C$—$CH_2$—O— | N | N | N | $CH_2$ | H | 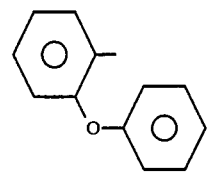 | |
| 489 | N | $F_3C$—$CH_2$—O— | N | N | N | $CH_2$ | H | 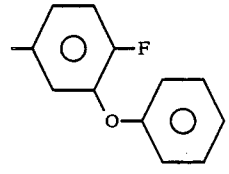 | |
| 490 | N | $F_3C$—$CH_2$—O— | N | N | N | $CH_2$ | H | 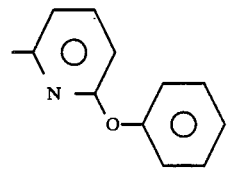 | |
| 491 | N | $F_3C$—$CH_2$—O— | N | N | N | $CH_2$ | H | 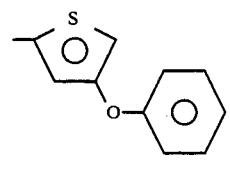 | |
| 492 | N | $F_3C$—$CH_2$—O— | N | N | N | $CH_2$ | H | 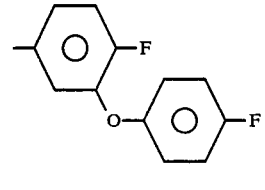 | |
| 493 | N | $F_3C$—$CH_2$—O— | N | N | N | O | H | 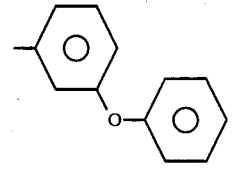 | |
| 494 | N | $F_3C$—$CH_2$—O— | N | N | N | O | H | 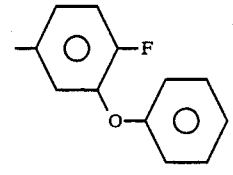 | |
| 495 | N | $F_3C$—$CH_2$—O— | N | N | N | O | H | 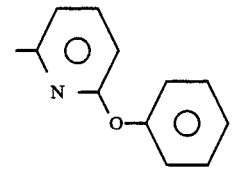 | |

TABLE 2

Compounds of the formula I having $R^2$ and $R^3 = CH_2\!-\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 496 | N | EtO | CH | CH | CH | $CH_2$ | H | (phenoxyphenyl) | |
| 497 | N | EtO | CH | CH | CH | $CH_2$ | H | (2-fluorophenoxy-phenyl) | |
| 498 | N | EtO | CH | CH | CH | $CH_2$ | H | (pyridinyloxy-phenyl) | |
| 499 | N | EtO | CH | CH | CH | $CH_2$ | H | (thienyloxy-phenyl) | |
| 500 | N | EtO | CH | CH | CH | $CH_2$ | H | (2-fluoro-4'-fluorophenoxyphenyl) | |
| 501 | N | EtO | CH | CH | CH | $CH_2$ | CN | (phenoxyphenyl) | |
| 502 | N | EtO | CH | CH | CH | $CH_2$ | CN | (2-fluorophenoxy-phenyl) | |
| 503 | N | EtO | CH | CH | CH | O | H | (phenoxyphenyl) | pale yellow oil |

TABLE 2-continued

Compounds of the formula I having $R^2$ and $R^3$ = $CH_2\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 504 | N | EtO | CH | CH | CH | O | H | | |
| 505 | N | EtO | CH | CH | CH | O | H | | |
| 506 | N | EtO | CH | CH | CH | O | CN | | |
| 507 | N | Cl | CH | CH | CH | $CH_2$ | H | | |
| 508 | N | Cl | CH | CH | CH | $CH_2$ | H | | |
| 509 | N | Cl | CH | CH | CH | $CH_2$ | H | | |
| 510 | N | Cl | CH | CH | CH | $CH_2$ | H | | |
| 511 | N | Cl | CH | CH | CH | $CH_2$ | H | | |

TABLE 2-continued

Compounds of the formula I having $R^2$ and $R^3 = \underset{\diagdown\diagup}{CH_2-CH_2}$; A = N, CH or $CR^1$

| Compound No. | A | $R^1$ | B | C' | D | X | $R^4$ | $R^5$ | Physical data |
|---|---|---|---|---|---|---|---|---|---|
| 512 | N | Cl | CH | CH | CH | $CH_2$ | H | phenoxy-fluorophenyl | |
| 513 | N | Cl | CH | CH | CH | O | H | phenoxyphenyl | pale yellow oil |
| 514 | N | Cl | CH | CH | CH | O | H | phenoxy-fluorophenyl | |
| 515 | N | Cl | CH | CH | CH | O | H | phenoxy-pyridyl | |
| 516 | N | Cl | CH | CH | CH | O | CN | phenoxyphenyl | |
| 517 | N | Cl | CH | CH | CH | O | $CH_3$ | phenoxyphenyl | |
| 518 | N | $H_3CO$ | CH | CH | CH | $CH_2$ | H | phenoxyphenyl | |
| 519 | N | $H_3CO$ | CH | CH | CH | $CH_2$ | H | phenoxy-fluorophenyl | |

TABLE 2-continued

Compounds of the formula I having $R^2$ and $R^3$ = $CH_2$—$CH_2$; A = N, CH or $CR^1$

| Compound No. | A | $R^1$ | B | C' | D | X | $R^4$ | $R^5$ | Physical data |
|---|---|---|---|---|---|---|---|---|---|
| 520 | N | $H_3CO$ | CH | CH | CH | $CH_2$ | H | | |
| 521 | N | $H_3CO$ | CH | CH | CH | $CH_2$ | H | | |
| 522 | N | $H_3CO$ | CH | CH | CH | $CH_2$ | CN | | |
| 523 | N | $H_3CO$ | CH | CH | CH | $CH_2$ | CN | | |
| 524 | N | $H_3CO$ | CH | CH | CH | O | H | | |
| 525 | N | $H_3CO$ | CH | CH | CH | O | H | | |
| 526 | N | $H_3CO$ | CH | CH | CH | O | H | | |
| 527 | N | $H_3CO$ | CH | CH | CH | O | CN | | |

TABLE 2-continued
Compounds of the formula I having $R^2$ and $R^3$ = CH$_2$—CH$_2$; A = N, CH or $CR^1$
| Compound No. | A | $R^1$ | B | C' | D | X | $R^4$ | $R^5$ | Physical data |
|---|---|---|---|---|---|---|---|---|---|
| 528 | N | H$_3$CO | CH | CH | CH | O | CH$_3$ | 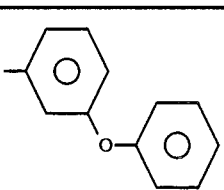 | |
| 529 | N | EtS | CH | CH | CH | CH$_2$ | H | 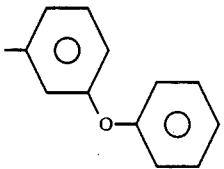 | |
| 530 | N | EtS | CH | CH | CH | CH$_2$ | H | 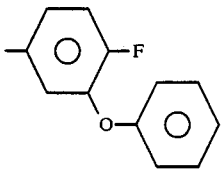 | |
| 531 | N | EtS | CH | CH | CH | CH$_2$ | H | 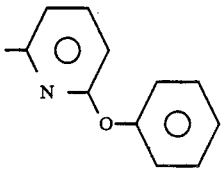 | |
| 532 | N | EtS | CH | CH | CH | CH$_2$ | H | 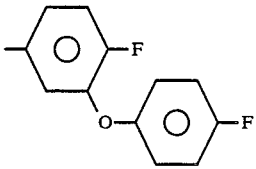 | |
| 533 | N | EtS | CH | CH | CH | CH$_2$ | CN | 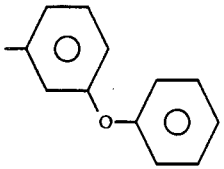 | |
| 534 | N | EtS | CH | CH | CH | CH$_2$ | CN | 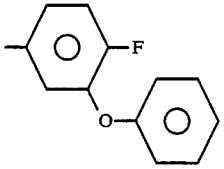 | |
| 535 | N | EtS | CH | CH | CH | O | H | 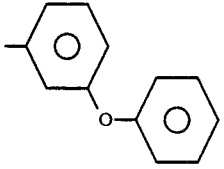 | |

TABLE 2-continued
Compounds of the formula I having $R^2$ and $R^3 = CH_2\text{—}CH_2$; A = N, CH or $CR^1$
| Compound No. | A | $R^1$ | B | C' | D | X | $R^4$ | $R^5$ | Physical data |
|---|---|---|---|---|---|---|---|---|---|
| 536 | N | EtS | CH | CH | CH | O | H | 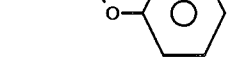 | |
| 537 | N | EtS | CH | CH | CH | O | H | 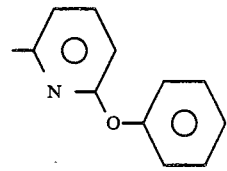 | |
| 538 | N | EtS | CH | CH | CH | O | CN | 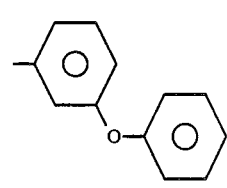 | |
| 539 | N | EtS | CH | CH | CH | O | $CH_3$ | 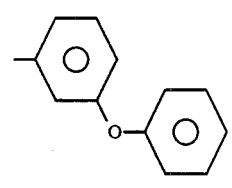 | |
| 540 | N | $H_3CS$ | CH | CH | CH | $CH_2$ | H | 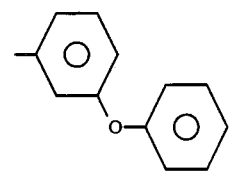 | |
| 541 | N | $H_3CS$ | CH | CH | CH | $CH_2$ | H | 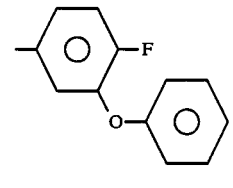 | |
| 542 | N | $H_3CS$ | CH | CH | CH | $CH_2$ | H | 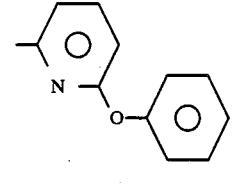 | |
| 543 | N | $H_3CS$ | CH | CH | CH | $CH_2$ | H | 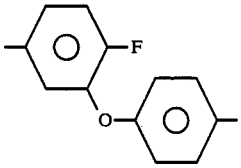 | |

TABLE 2-continued

Compounds of the formula I having $R^2$ and $R^3$ = $CH_2-CH_2$; A = N, CH or $CR^1$

| Compound No. | A | $R^1$ | B | C' | D | X | $R^4$ | $R^5$ | Physical data |
|---|---|---|---|---|---|---|---|---|---|
| 544 | N | $H_3CS$ | CH | CH | CH | $CH_2$ | CN | phenoxyphenyl | |
| 545 | N | $H_3CS$ | CH | CH | CH | $CH_2$ | CN | (2-fluorophenoxy)phenyl | |
| 546 | N | $H_3CS$ | CH | CH | CH | O | H | phenoxyphenyl | |
| 547 | N | $H_3CS$ | CH | CH | CH | O | H | (2-fluorophenoxy)phenyl | |
| 548 | N | $H_3CS$ | CH | CH | CH | O | H | phenoxypyridyl | |
| 549 | N | $H_3CS$ | CH | CH | CH | O | CN | phenoxyphenyl | |
| 550 | N | $H_3CS$ | CH | CH | CH | O | $CH_3$ | phenoxyphenyl | |
| 551 | CCl | Cl | CH | N | CH | $CH_2$ | H | phenoxyphenyl | |

TABLE 2-continued
Compounds of the formula I having $R^2$ and $R^3 = \underset{\diagdown\;\;\diagup}{CH_2-CH_2}$; A = N, CH or $CR^1$
| Compound No. | A | $R^1$ | B | C' | D | X | $R^4$ | $R^5$ | Physical data |
|---|---|---|---|---|---|---|---|---|---|
| 552 | CCl | Cl | CH | N | CH | $CH_2$ | H | 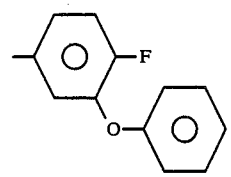 | |
| 553 | CCl | Cl | CH | N | CH | $CH_2$ | H | 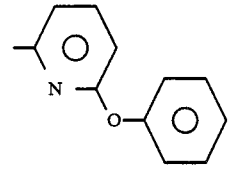 | |
| 554 | CCl | Cl | CH | N | CH | $CH_2$ | H | 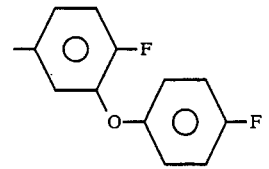 | |
| 555 | CCl | Cl | CH | N | CH | $CH_2$ | CN | 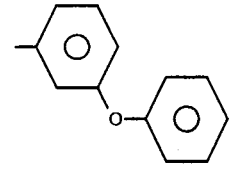 | |
| 556 | CCl | Cl | CH | N | CH | $CH_2$ | CN | 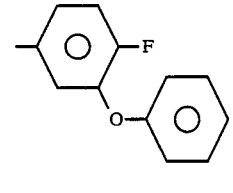 | |
| 557 | CCl | Cl | CH | N | CH | O | H | 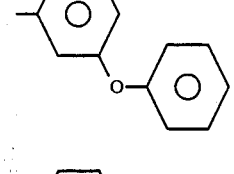 | |
| 558 | CCl | Cl | CH | N | CH | O | H | 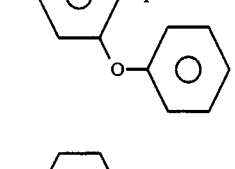 | |
| 559 | CCl | Cl | CH | N | CH | O | H | 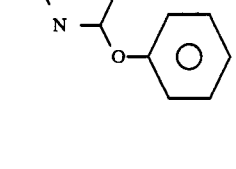 | |

TABLE 2-continued
Compounds of the formula I having $R^2$ and $R^3$ = $CH_2\!\!-\!\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 560 | CCl | Cl | CH | N | CH | O | CN | 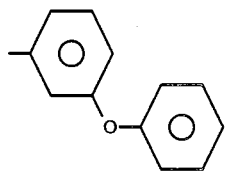 | |
| 561 | CCl | Cl | CH | N | CH | O | $CH_3$ | 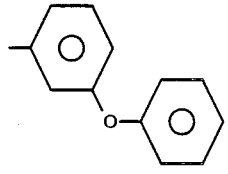 | |
| 562 | CCl | EtO | CH | N | CH | $CH_2$ | H | 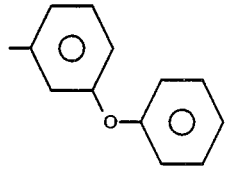 | |
| 563 | CCl | EtO | CH | N | CH | $CH_2$ | H | 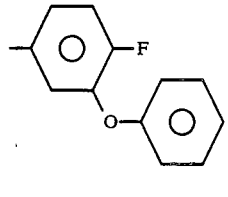 | |
| 564 | CCl | EtO | CH | N | CH | $CH_2$ | H | 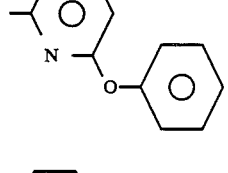 | |
| 565 | CCl | EtO | CH | N | CH | $CH_2$ | H | 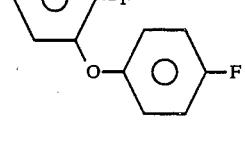 | |
| 566 | CCl | EtO | CH | N | CH | $CH_2$ | CN | 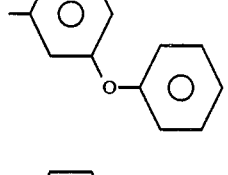 | |
| 567 | CCl | EtO | CH | N | CH | $CH_2$ | CN | 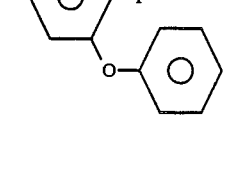 | |

TABLE 2-continued
Compounds of the formula I having $R^2$ and $R^3$ = CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 568 | CCl | EtO | CH | N | CH | O | H | 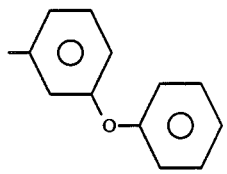 | |
| 569 | CCl | EtO | CH | N | CH | O | H | 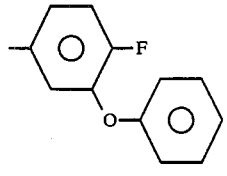 | |
| 570 | CCl | EtO | CH | N | CH | O | H | 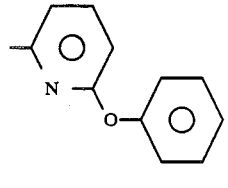 | |
| 571 | CCl | EtO | CH | N | CH | O | CN | 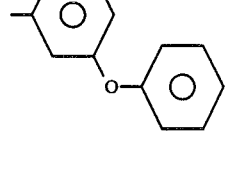 | |
| 572 | CCl | EtO | CH | N | CH | O | CH$_3$ | 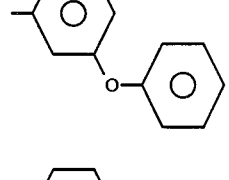 | |
| 573 | CF | EtO | CH | H | CH | CH$_2$ | H | 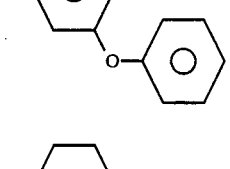 | |
| 574 | CF | EtO | CH | N | CH | CH$_2$ | H | 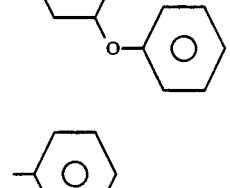 | |
| 575 | CF | EtO | CH | H | CH | CH$_2$ | H | 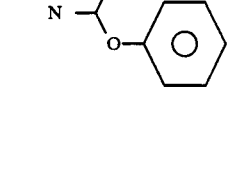 | |

TABLE 2-continued
Compounds of the formula I having $R^2$ and $R^3 = CH_2\!-\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 576 | CF | EtO | CH | N | CH | $CH_2$ | H | 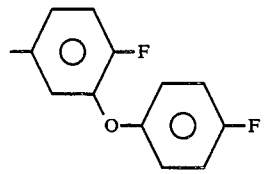 | |
| 577 | CF | EtO | CH | N | CH | $CH_2$ | CN | 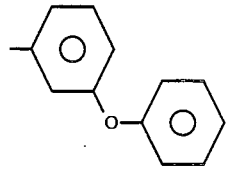 | |
| 578 | CF | EtO | CH | N | CH | $CH_2$ | CN | 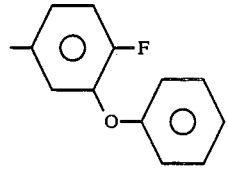 | |
| 579 | CF | EtO | CH | N | CH | O | H | 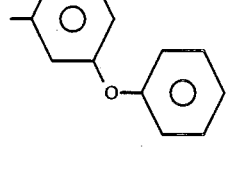 | |
| 580 | CF | EtO | CH | N | CH | O | H | 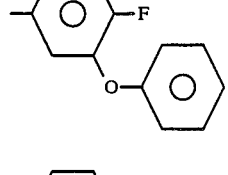 | |
| 581 | CF | EtO | CH | N | CH | O | H | 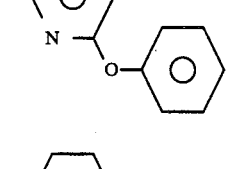 | |
| 582 | CF | EtO | CH | N | CH | O | CN | 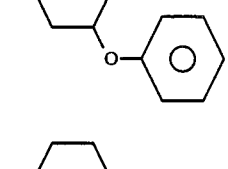 | |
| 583 | CF | EtO | CH | N | CH | O | $CH_3$ | 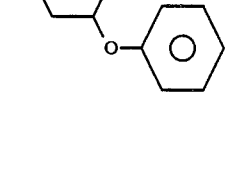 | |

TABLE 2-continued

Compounds of the formula I having $R^2$ and $R^3$ = $CH_2$—$CH_2$; A = N, CH or $CR^1$

| Compound No. | A | $R^1$ | B | C' | D | X | $R^4$ | $R^5$ | Physical data |
|---|---|---|---|---|---|---|---|---|---|
| 584 | | C—O—$CH_2$—O | CH | N | CH | $CH_2$ | H | | |
| 585 | | C—O—$CH_2$—O | CH | N | CH | $CH_2$ | H | | |
| 586 | | C—O—$CH_2$—O | CH | N | CH | $CH_2$ | H | | |
| 587 | | C—O—$CH_2$—O | CH | N | CH | $CH_2$ | H | | |
| 588 | | C—O—$CH_2$—O | CH | N | CH | $CH_2$ | CN | | |
| 589 | | C—O—$CH_2$—O | CH | N | CH | $CH_2$ | CN | | |
| 590 | | C—O—$CH_2$—O | CH | N | CH | O | H | | |
| 591 | | C—O—$CH_2$—O | CH | N | CH | O | H | | |

TABLE 2-continued

Compounds of the formula I having $R^2$ and $R^3$ = $CH_2\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 592 | | C—O—$CH_2$—O | CH | N | CH | O | H | (6-methylpyridin-2-yl)oxyphenyl | |
| 593 | | C—O—$CH_2$—O | CH | N | CH | O | CN | phenoxyphenyl | |
| 594 | | C—O—$CH_2$—O | CH | N | CH | O | $CH_3$ | phenoxyphenyl | |
| 595 | CH | EtO | | N | CH | CH | $CH_2$ | H | phenoxyphenyl | |
| 596 | CH | EtO | | N | CH | CH | $CH_2$ | H | (2-fluorophenoxy)phenyl | |
| 597 | CH | EtO | | N | CH | CH | $CH_2$ | H | (pyridin-2-yloxy)phenyl | |
| 598 | CH | EtO | | N | CH | CH | $CH_2$ | H | (4-fluorophenoxy)-2-fluorophenyl | |
| 599 | CH | EtO | | N | CH | CH | $CH_2$ | CN | phenoxyphenyl | |

TABLE 2-continued
Compounds of the formula I having $R^2$ and $R^3$ = CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 600 | CH | EtO | N | CH | CH | CH$_2$ | CN | 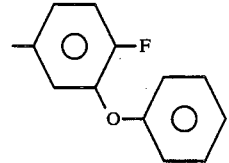 | |
| 601 | CH | EtO | N | CH | CH | O | H | 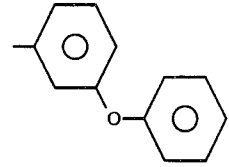 | |
| 602 | CH | EtO | N | CH | CH | O | H | 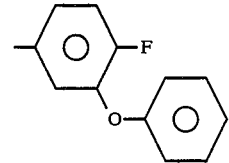 | |
| 603 | CH | EtO | N | CH | CH | O | H | 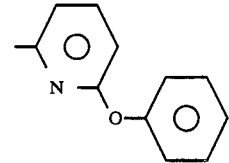 | |
| 604 | CH | EtO | N | CH | CH | O | CN | 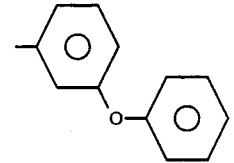 | |
| 605 | CH | EtO | N | CH | CH | O | CH$_3$ | 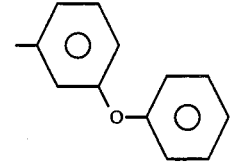 | |
| 606 | CH | Cl | N | CH | CH | CH$_2$ | H | 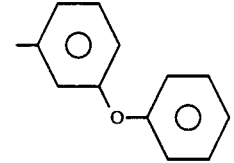 | |
| 607 | CH | Cl | N | CH | CH | CH$_2$ | H | 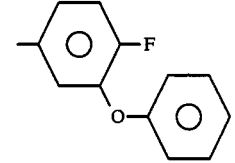 | |

TABLE 2-continued
Compounds of the formula I having $R^2$ and $R^3$ = $CH_2\!\!-\!\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 608 | CH | Cl | N | CH | CH | $CH_2$ | H | 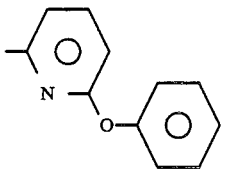 | |
| 609 | CH | Cl | N | CH | CH | $CH_2$ | H | 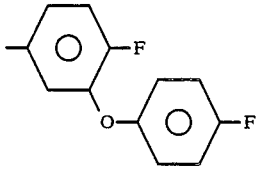 | |
| 610 | CH | Cl | N | CH | CH | $CH_2$ | CN | 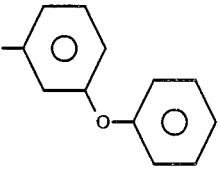 | |
| 611 | CH | Cl | N | CH | CH | $CH_2$ | CN | 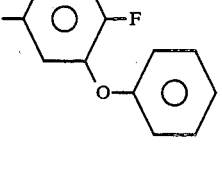 | |
| 612 | CH | Cl | N | CH | CH | O | H | 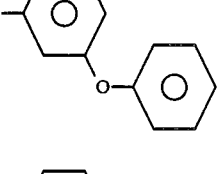 | |
| 613 | CH | Cl | N | CH | CH | O | H | 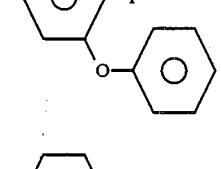 | |
| 614 | CH | Cl | N | CH | CH | O | H | 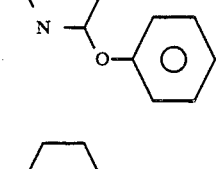 | |
| 615 | CH | Cl | N | CH | CH | O | CN | 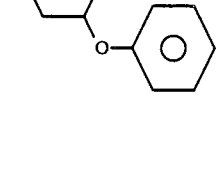 | |

TABLE 2-continued
Compounds of the formula I having $R^2$ and $R^3 = CH_2\text{---}CH_2$; A = N, CH or $CR^1$
| Compound No. | A | $R^1$ | B | C' | D | X | $R^4$ | $R^5$ | Physical data |
|---|---|---|---|---|---|---|---|---|---|
| 616 | CH | Cl | N | CH | CH | O | $CH_3$ | 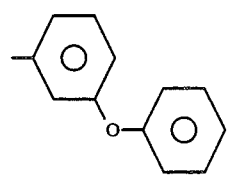 | |
| 617 | CH | $H_3CO$ | N | CH | CH | $CH_2$ | H | 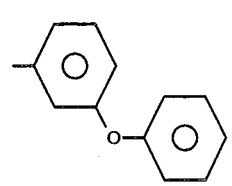 | |
| 618 | CH | $H_3CO$ | N | CH | CH | $CH_2$ | H | 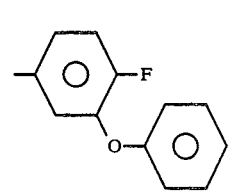 | |
| 619 | CH | $H_3CO$ | N | CH | CH | $CH_2$ | H | 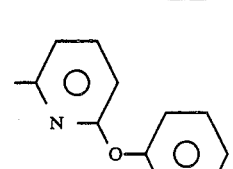 | |
| 620 | CH | $H_3CO$ | N | CH | CH | $CH_2$ | H | 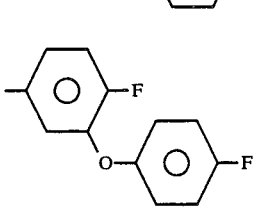 | |
| 621 | CH | $H_3CO$ | N | CH | CH | $CH_2$ | CN | 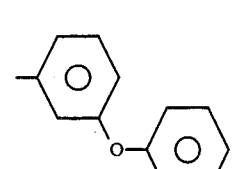 | |
| 622 | CH | $H_3CO$ | N | CH | CH | $CH_2$ | CN | 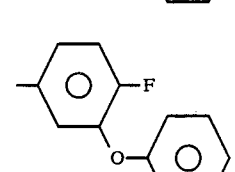 | |
| 623 | CH | $H_3CO$ | N | CH | CH | O | H | 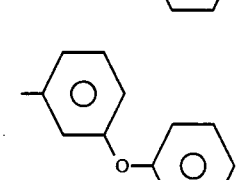 | |

TABLE 2-continued

Compounds of the formula I having $R^2$ and $R^3$ = CH$_2$—CH$_2$; A = N, CH or CR$^1$

| Compound No. | A | $R^1$ | B | C' | D | X | $R^4$ | $R^5$ | Physical data |
|---|---|---|---|---|---|---|---|---|---|
| 624 | CH | H$_3$CO | N | CH | CH | O | H | phenoxy-fluorophenyl | |
| 625 | CH | H$_3$CO | N | CH | CH | O | H | pyridinyl-O-phenyl | |
| 626 | CH | H$_3$CO | N | CH | CH | O | CN | phenoxy-phenyl | |
| 627 | CH | H$_3$CO | N | CH | CH | O | CH$_3$ | phenoxy-phenyl | |
| 628 | CH | EtS | N | CH | CH | CH$_2$ | H | phenoxy-phenyl | |
| 629 | CH | EtS | N | CH | CH | CH$_2$ | H | phenoxy-fluorophenyl | |
| 630 | CH | EtS | N | CH | CH | CH$_2$ | H | pyridinyl-O-phenyl | |
| 631 | CH | EtS | N | CH | CH | CH$_2$ | H | fluorophenoxy-fluorophenyl | |

TABLE 2-continued

Compounds of the formula I having $R^2$ and $R^3$ = CH$_2$—CH$_2$; A = N, CH or CR$^1$

| Compound No. | A | R$^1$ | B | C' | D | X | R$^4$ | R$^5$ | Physical data |
|---|---|---|---|---|---|---|---|---|---|
| 632 | CH | EtS | N | CH | CH | CH$_2$ | CN | 4-(phenoxy)phenyl | |
| 633 | CH | EtS | N | CH | CH | CH$_2$ | CN | 4-(2-fluorophenoxy)phenyl | |
| 634 | CH | EtS | N | CH | CH | O | H | 4-(phenoxy)phenyl | |
| 635 | CH | EtS | N | CH | CH | O | H | 4-(2-fluorophenoxy)phenyl | |
| 636 | CH | EtS | N | CH | CH | O | H | 6-(phenoxy)pyridin-2-yl | |
| 637 | CH | EtS | N | CH | CH | O | CN | 4-(phenoxy)phenyl | |
| 638 | CH | EtS | N | CH | CH | O | CH$_3$ | 4-(phenoxy)phenyl | |
| 639 | CH | F$_2$CHO | N | CH | CH | CH$_2$ | H | 4-(phenoxy)phenyl | |

TABLE 2-continued
Compounds of the formula I having $R^2$ and $R^3 = CH_2-CH_2$; $A = N$, CH or $CR^1$
| Compound No. | A | $R^1$ | B | C' | D | X | $R^4$ | $R^5$ | Physical data |
|---|---|---|---|---|---|---|---|---|---|
| 640 | CH | $F_2$CHO | N | CH | CH | $CH_2$ | H | 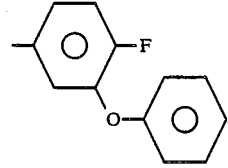 | |
| 641 | CH | $F_2$CHO | N | CH | CH | $CH_2$ | H | 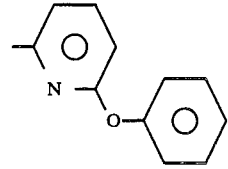 | |
| 642 | CH | $F_2$CHO | N | CH | CH | $CH_2$ | H | 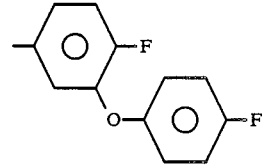 | |
| 643 | CH | $F_2$CHO | N | CH | CH | $CH_2$ | CN | 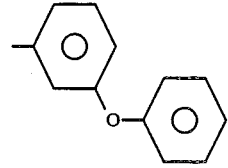 | |
| 644 | CH | $F_2$CHO | N | CH | CH | $CH_2$ | CN | 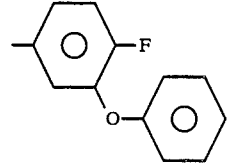 | |
| 645 | CH | $F_2$CHO | N | CH | CH | O | H | 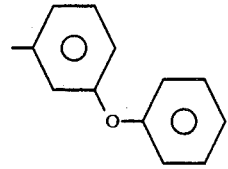 | |
| 646 | CH | $F_2$CHO | N | CH | CH | O | H | 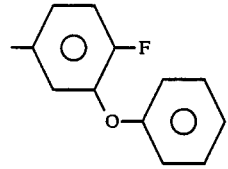 | |
| 647 | CH | $F_2$CHO | N | CH | CH | O | H | 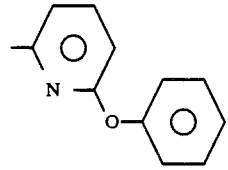 | |

TABLE 2-continued

Compounds of the formula I having $R^2$ and $R^3 = CH_2\!-\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 648 | CH | $F_2CHO$ | N | CH | CH | O | CN | (phenyl-O-phenyl) | |
| 649 | CH | $F_2CHO$ | N | CH | CH | O | $CH_3$ | (phenyl-O-phenyl) | |
| 650 | CCl | Cl | N | CH | CH | $CH_2$ | H | (phenyl-O-phenyl) | |
| 651 | CCl | Cl | N | CH | CH | $CH_2$ | H | (phenyl(F)-O-phenyl) | |
| 652 | CCl | Cl | N | CH | CH | $CH_2$ | H | (pyridyl-O-phenyl) | |
| 653 | CCl | Cl | N | CH | CH | $CH_2$ | H | (phenyl(F)-O-phenyl(F)) | |
| 654 | CCl | Cl | N | CH | CH | $CH_2$ | CN | (phenyl-O-phenyl) | |
| 655 | CCl | Cl | N | CH | CH | $CH_2$ | CN | (phenyl(F)-O-phenyl) | |

TABLE 2-continued

Compounds of the formula I having $R^2$ and $R^3 = CH_2\!\!-\!\!CH_2$ ; A = N, CH or $CR^1$

| Compound No. | A | $R^1$ | B | C' | D | X | $R^4$ | $R^5$ | Physical data |
|---|---|---|---|---|---|---|---|---|---|
| 656 | CCl | Cl | N | CH | CH | O | H | phenyl-O-phenyl | |
| 657 | CCl | Cl | N | CH | CH | O | H | (fluoro)phenyl-O-phenyl | |
| 658 | CCl | Cl | N | CH | CH | O | H | pyridyl-O-phenyl | |
| 659 | CCl | Cl | N | CH | CH | O | CN | phenyl-O-phenyl | |
| 660 | CCl | Cl | N | CH | CH | O | $CH_3$ | phenyl-O-phenyl | |
| 661 | CCl | EtO | N | CH | CH | $CH_2$ | H | phenyl-O-phenyl | |
| 662 | CCl | EtO | N | CH | CH | $CH_2$ | H | (fluoro)phenyl-O-phenyl | |
| 663 | CCl | EtO | N | CH | CH | $CH_2$ | H | pyridyl-O-phenyl | |

TABLE 2-continued

Compounds of the formula I having $R^2$ and $R^3 = CH_2-CH_2$; A = N, CH or $CR^1$

| Compound No. | A | $R^1$ | B | C' | D | X | $R^4$ | $R^5$ | Physical data |
|---|---|---|---|---|---|---|---|---|---|
| 664 | CCl | EtO | N | CH | CH | $CH_2$ | H | 4-(2-fluoro-4-fluorophenoxy)phenyl | |
| 665 | CCl | EtO | N | CH | CH | $CH_2$ | CN | 3-phenoxyphenyl | |
| 666 | CCl | EtO | N | CH | CH | $CH_2$ | CN | 4-(2-fluoro-phenoxy)phenyl | |
| 667 | CCl | EtO | N | CH | CH | O | H | 3-phenoxyphenyl | |
| 668 | CCl | EtO | N | CH | CH | O | H | 4-(2-fluoro-phenoxy)phenyl | |
| 669 | CCl | EtO | N | CH | CH | O | H | 6-phenoxypyridin-2-yl | |
| 670 | CCl | EtO | N | CH | CH | $CH_2$ | CN | 3-phenoxyphenyl | |
| 671 | CCl | EtO | N | CH | CH | O | $CH_3$ | 3-phenoxyphenyl | |

TABLE 2-continued
Compounds of the formula I having $R^2$ and $R^3 = CH_2\text{—}CH_2$; A = N, CH or $CR^1$
| Compound No. | A | $R^1$ | B | C' | D | X | $R^4$ | $R^5$ | Physical data |
|---|---|---|---|---|---|---|---|---|---|
| 672 | | C—O—$CH_2$—O | N | CH | CH | $CH_2$ | H | 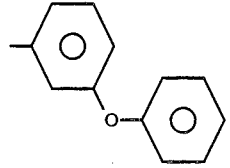 | |
| 673 | | C—O—$CH_2$—O | N | CH | CH | $CH_2$ | H | 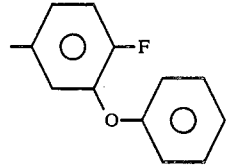 | |
| 674 | | C—O—$CH_2$—O | N | CH | CH | $CH_2$ | H | 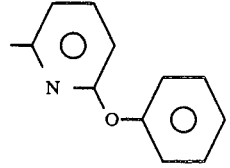 | |
| 675 | | C—O—$CH_2$—O | N | CH | CH | $CH_2$ | H | 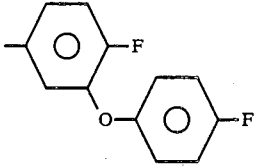 | |
| 676 | | C—O—$CH_2$—O | N | CH | CH | $CH_2$ | CN | 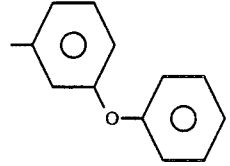 | |
| 677 | | C—O—$CH_2$—O | N | CH | CH | $CH_2$ | CN | 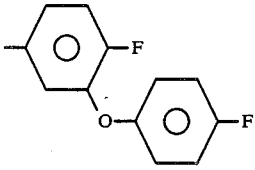 | |
| 678 | | C—O—$CH_2$—O | N | CH | CH | O | H | 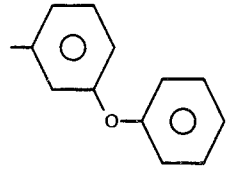 | |
| 679 | | C—O—$CH_2$—O | N | CH | CH | O | H | 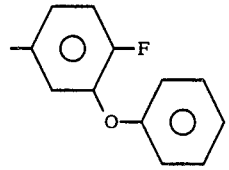 | |

TABLE 2-continued

Compounds of the formula I having $R^2$ and $R^3 = CH_2\!-\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 680 | | C—O—CH$_2$—O | N | CH | CH | O | H | pyridinyl-O-phenyl | |
| 681 | | C—O—CH$_2$—O | N | CH | CH | O | CN | phenyl-O-phenyl | |
| 682 | | C—O—CH$_2$—O | N | CH | CH | O | CH$_3$ | phenyl-O-phenyl | |
| 683 | | C—O—CH$_2$—O | CH | CH | N | CH$_2$ | H | phenyl-O-phenyl | |
| 684 | | C—O—CH$_2$—O | CH | CH | N | CH$_2$ | H | (F-phenyl)-O-phenyl | |
| 685 | | C—O—CH$_2$—O | CH | CH | N | CH$_2$ | H | pyridinyl-O-phenyl | |
| 686 | | C—O—CH$_2$—O | CH | CH | N | CH$_2$ | H | (F-phenyl)-O-(F-phenyl) | |
| 687 | | C—O—CH$_2$—O | CH | CH | N | CH$_2$ | CN | phenyl-O-phenyl | |

TABLE 2-continued
Compounds of the formula I having $R^2$ and $R^3$ = CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 688 |   | C—O—CH$_2$—O | CH | CH | N | CH$_2$ | CN | 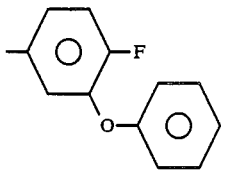 |   |
| 689 |   | C—O—CH$_2$—O | CH | CH | N | O | H | 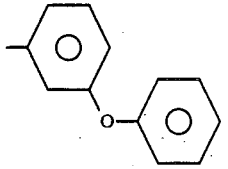 |   |
| 690 |   | C—O—CH$_2$—O | CH | CH | N | O | H | 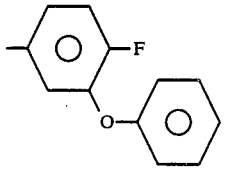 |   |
| 691 |   | C—O—CH$_2$—O | CH | CH | N | O | H | 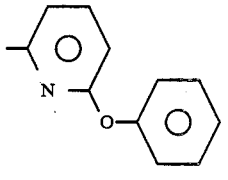 |   |
| 692 |   | C—O—CH$_2$—O | CH | CH | N | O | CN | 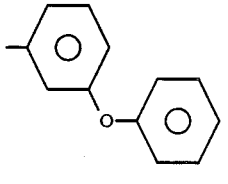 |   |
| 693 |   | C—O—CH$_2$—O | CH | CH | N | O | CH$_3$ | 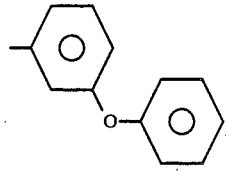 |   |
| 694 | N | EtO | CH | N | CH | CH$_2$ | H | 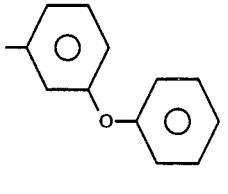 |   |
| 695 | N | EtO | CH | N | CH | CH$_2$ | H | 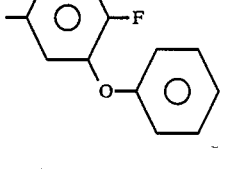 |   |

TABLE 2-continued

Compounds of the formula I having $R^2$ and $R^3$ = $CH_2\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 696 | N | EtO | CH | N | CH | $CH_2$ | H | pyridyl-O-phenyl | |
| 697 | N | EtO | CH | N | CH | $CH_2$ | H | (F-phenyl)-O-(F-phenyl) | |
| 698 | N | EtO | CH | N | CH | $CH_2$ | CN | phenyl-O-phenyl | |
| 699 | N | EtO | CH | N | CH | $CH_2$ | CN | (F-phenyl)-O-phenyl | |
| 700 | N | EtO | CH | N | CH | O | H | phenyl-O-phenyl | |
| 701 | N | EtO | CH | N | CH | O | H | (F-phenyl)-O-phenyl | |
| 702 | N | EtO | CH | N | CH | O | H | pyridyl-O-phenyl | |
| 703 | N | EtO | CH | N | CH | O | CN | phenyl-O-phenyl | |

TABLE 2-continued

Compounds of the formula I having $R^2$ and $R^3 = CH_2\text{---}CH_2$; A = N, CH or $CR^1$

| Compound No. | A | $R^1$ | B | C' | D | X | $R^4$ | $R^5$ | Physical data |
|---|---|---|---|---|---|---|---|---|---|
| 704 | N | EtO | CH | N | CH | O | $CH_3$ | diphenyl ether | |
| 705 | N | Cl | CH | N | CH | $CH_2$ | H | diphenyl ether | |
| 706 | N | Cl | CH | N | CH | $CH_2$ | H | fluorodiphenyl ether | |
| 707 | N | Cl | CH | N | CH | $CH_2$ | H | pyridyl phenyl ether | |
| 708 | N | Cl | CH | N | CH | $CH_2$ | H | difluorodiphenyl ether | |
| 709 | N | Cl | CH | N | CH | $CH_2$ | CN | diphenyl ether | |
| 710 | N | Cl | CH | N | CH | $CH_2$ | CN | fluorodiphenyl ether | |
| 711 | N | Cl | CH | N | CH | O | H | diphenyl ether | |

TABLE 2-continued
Compounds of the formula I having $R^2$ and $R^3$ = CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 712 | N | Cl | CH | N | CH | O | H | 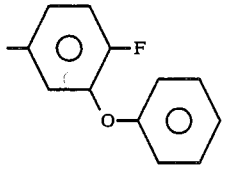 | |
| 713 | N | Cl | CH | N | CH | O | H | 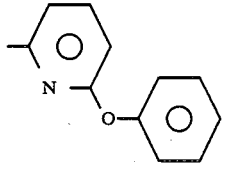 | |
| 714 | N | Cl | CH | N | CH | O | CN | 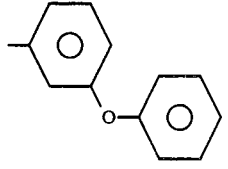 | |
| 715 | N | Cl | CH | N | CH | O | CH$_3$ | 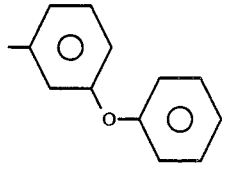 | |
| 716 | N | H$_3$CO | CH | N | CH | CH$_2$ | H | 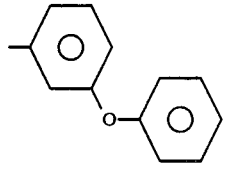 | |
| 717 | N | H$_3$CO | CH | N | CH | CH$_3$ | H | 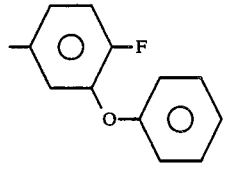 | |
| 718 | N | H$_3$CO | CH | N | CH | CH$_2$ | H | 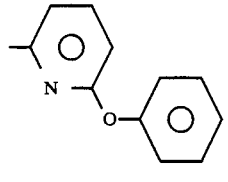 | |
| 719 | N | H$_3$CO | CH | N | CH | CH$_2$ | H | 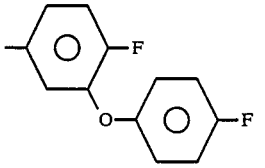 | |

TABLE 2-continued
Compounds of the formula I having $R^2$ and $R^3 = \underset{\diagdown \diagup}{CH_2 - CH_2}$; A = N, CH or $CR^1$
| Compound No. | A | $R^1$ | B | C' | D | X | $R^4$ | $R^5$ | Physical data |
|---|---|---|---|---|---|---|---|---|---|
| 720 | N | H$_3$CO | CH | N | CH | CH$_2$ | CN | 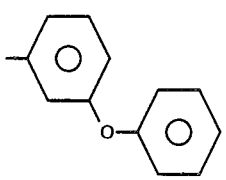 | |
| 721 | N | H$_3$CO | CH | N | CH | CH$_2$ | CN | 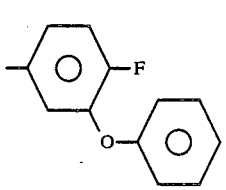 | |
| 722 | N | H$_3$CO | CH | N | CH | O | H | 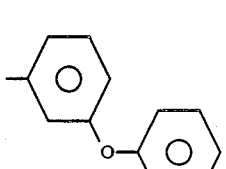 | |
| 723 | N | H$_3$CO | CH | N | CH | O | H | 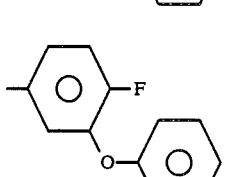 | |
| 724 | N | H$_3$CO | CH | N | CH | O | H | 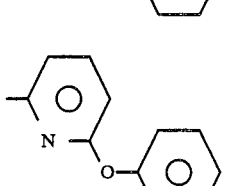 | |
| 725 | N | H$_3$CO | CH | N | CH | O | CN | 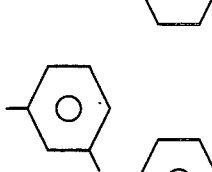 | |
| 726 | N | H$_3$CO | CH | N | CH | O | CH$_3$ | 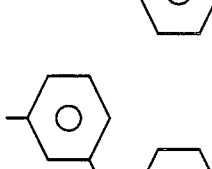 | |
| 727 | N | EtS | CH | N | CH | CH$_2$ | H | 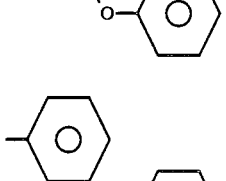 | |

TABLE 2-continued
Compounds of the formula I having $R^2$ and $R^3$ = CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 728 | N | EtS | CH | N | CH | CH$_2$ | H | 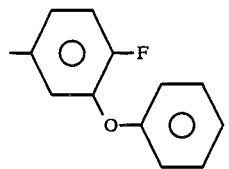 | |
| 729 | N | EtS | CH | N | CH | CH$_2$ | H | 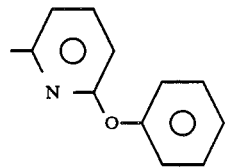 | |
| 730 | N | EtS | CH | N | CH | CH$_2$ | H | 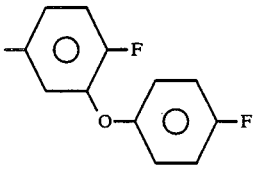 | |
| 731 | N | EtS | CH | N | CH | CH$_2$ | CN | 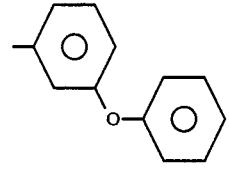 | |
| 732 | N | EtS | CH | N | CH | CH$_2$ | CN | 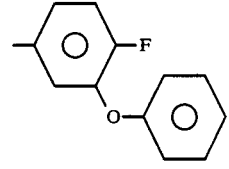 | |
| 733 | N | EtS | CH | N | CH | O | H | 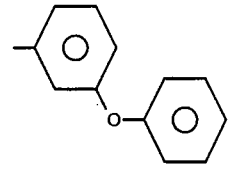 | |
| 734 | N | EtS | CH | N | CH | O | H | 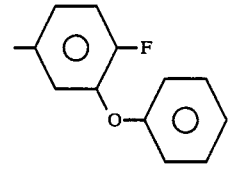 | |
| 735 | N | EtS | CH | N | CH | O | H | 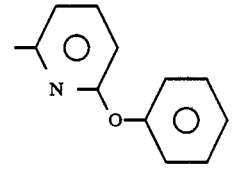 | |

TABLE 2-continued
Compounds of the formula I having $R^2$ and $R^3$ = $CH_2\!\!-\!\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 736 | N | EtS | CH | N | CH | O | CN | 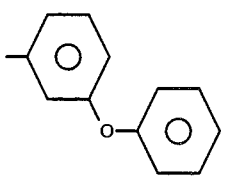 | |
| 737 | N | EtS | CH | N | CH | O | $CH_3$ | 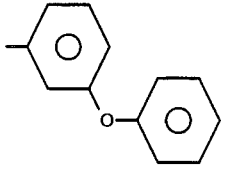 | |
| 738 | N | n-$C_3H_7$ | CH | N | CH | $CH_2$ | H | 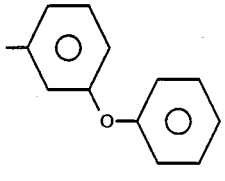 | |
| 739 | N | n-$C_3H_7$ | CH | N | CH | $CH_2$ | H | 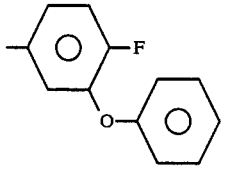 | |
| 740 | N | n-$C_3H_7$ | CH | N | CH | $CH_2$ | H | 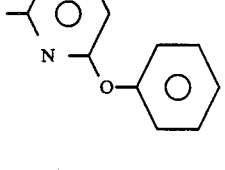 | |
| 741 | N | n-$C_3H_7$ | CH | N | CH | $CH_2$ | CN | 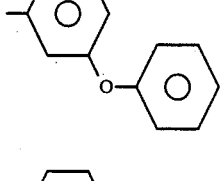 | |
| 742 | N | n-$C_3H_7$ | CH | N | CH | $CH_2$ | CH | 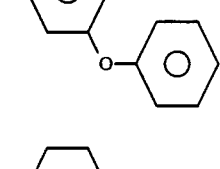 | |
| 743 | N | n-$C_3H_7$ | CH | N | CH | O | H | 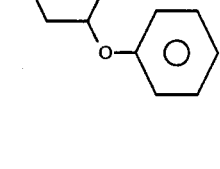 | |

TABLE 2-continued

Compounds of the formula I having $R^2$ and $R^3$ = $CH_2\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 744 | N | n-$C_3H_7$ | CH | N | CH | O | H | phenyl-2-F-phenoxyphenyl | |
| 745 | N | n-$C_3H_7$ | CH | N | CH | O | H | pyridyl-oxyphenyl | |
| 746 | N | n-$C_3H_7$ | CH | N | CH | O | CN | phenyl-oxyphenyl | |
| 747 | N | n-$C_3H_7$ | CH | N | CH | O | $CH_3$ | phenyl-oxyphenyl | |
| 748 | CH | EtO | N | CH | N | $CH_2$ | H | phenyl-oxyphenyl | |
| 749 | CH | EtO | N | CH | N | $CH_2$ | H | phenyl-2-F-phenoxyphenyl | |
| 750 | CH | EtO | N | CH | N | $CH_2$ | H | pyridyl-oxyphenyl | |
| 751 | CH | EtO | N | CH | N | $CH_2$ | H | 2-F-phenyl-oxy-4-F-phenyl | |

TABLE 2-continued

Compounds of the formula I having $R^2$ and $R^3$ = CH$_2$—CH$_2$; A = N, CH or CR$^1$

| Compound No. | A | R$^1$ | B | C' | D | X | R$^4$ | R$^5$ | Physical data |
|---|---|---|---|---|---|---|---|---|---|
| 752 | CH | EtO | N | CH | N | CH$_2$ | CN | phenoxyphenyl | |
| 753 | CH | EtO | N | CH | N | CH$_2$ | CN | (2-fluorophenoxy)phenyl | |
| 754 | CH | EtO | N | CH | N | O | H | phenoxyphenyl | |
| 755 | CH | EtO | N | CH | N | O | H | (2-fluorophenoxy)phenyl | |
| 756 | CH | EtO | N | CH | N | O | H | (phenoxy)pyridinyl | |
| 757 | CH | EtO | N | CH | N | O | CN | phenoxyphenyl | |
| 758 | CH | EtO | N | CH | N | O | CH$_3$ | phenoxyphenyl | |
| 759 | CH | Cl | N | CH | N | CH$_2$ | H | phenoxyphenyl | |

TABLE 2-continued
Compounds of the formula I having $R^2$ and $R^3 = CH_2-CH_2$; A = N, CH or $CR^1$
| Compound No. | A | $R^1$ | B | C' | D | X | $R^4$ | $R^5$ | Physical data |
|---|---|---|---|---|---|---|---|---|---|
| 760 | CH | Cl | N | CH | N | $CH_2$ | H | 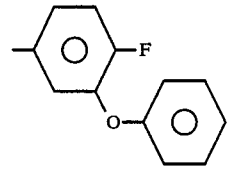 | |
| 761 | CH | Cl | N | CH | N | $CH_2$ | H | 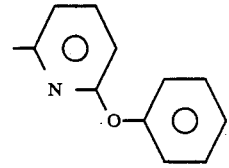 | |
| 762 | CH | Cl | N | CH | N | $CH_2$ | H | 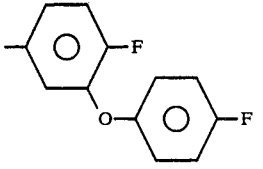 | |
| 763 | CH | Cl | N | CH | N | $CH_2$ | CN | 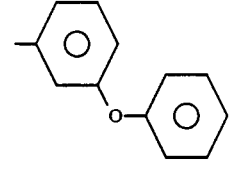 | |
| 764 | CH | Cl | N | CH | N | $CH_2$ | CN | 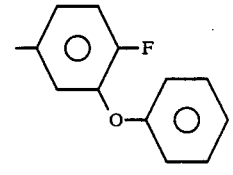 | |
| 765 | CH | Cl | N | CH | N | O | H | 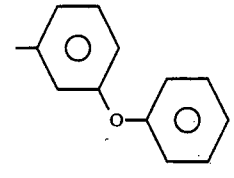 | |
| 776 | CH | Cl | N | CH | N | O | H | 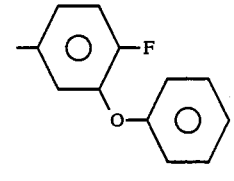 | |
| 777 | CH | Cl | N | CH | N | O | H | 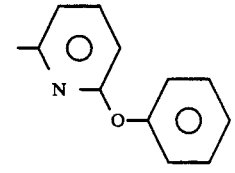 | |

TABLE 2-continued
Compounds of the formula I having $R^2$ and $R^3$ = $CH_2\!-\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 778 | CH | Cl | N | CH | N | O | CN | 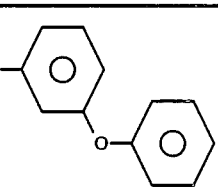 | |
| 779 | CH | Cl | N | CH | N | O | $CH_3$ | 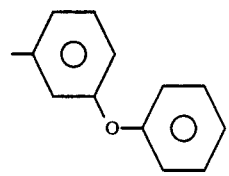 | |
| 780 | CH | $H_3CO$ | N | CH | N | $CH_2$ | H | 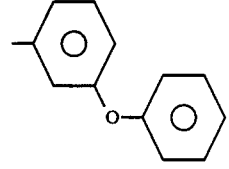 | |
| 781 | CH | $H_3CO$ | N | CH | N | $CH_2$ | H | 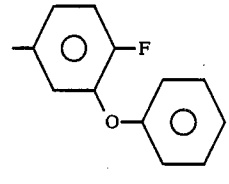 | |
| 782 | CH | $H_3CO$ | N | CH | N | $CH_2$ | H | 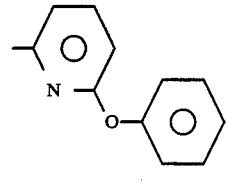 | |
| 783 | CH | $H_3CO$ | N | CH | N | $CH_2$ | H | 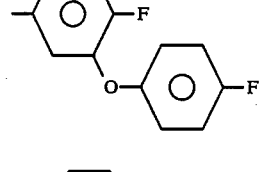 | |
| 784 | CH | $H_3CO$ | N | CH | N | $CH_2$ | CN | 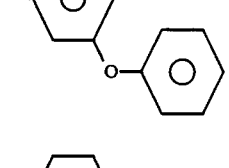 | |
| 785 | CH | $H_3CO$ | N | CH | N | $CH_2$ | CN | 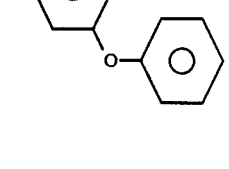 | |

TABLE 2-continued
Compounds of the formula I having $R^2$ and $R^3 = CH_2-CH_2$; A = N, CH or $CR^1$
| Compound No. | A | $R^1$ | B | C' | D | X | $R^4$ | $R^5$ | Physical data |
|---|---|---|---|---|---|---|---|---|---|
| 786 | CH | H$_3$CO | N | CH | N | O | H | 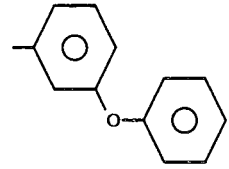 | |
| 787 | CH | H$_3$CO | N | CH | N | O | H | 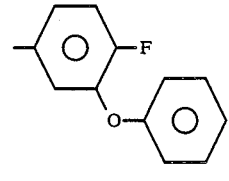 | |
| 788 | CH | H$_3$CO | N | CH | N | O | H | 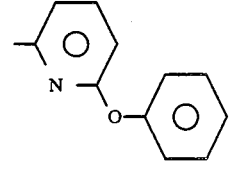 | |
| 789 | CH | H$_3$CO | N | CH | N | O | CN | 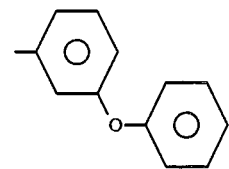 | |
| 790 | CH | H$_3$CO | N | CH | N | O | CH$_3$ | 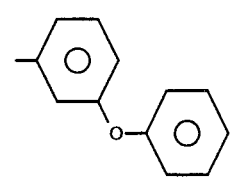 | |
| 791 | CH | F$_2$CHO | N | CH | N | CH$_2$ | H | 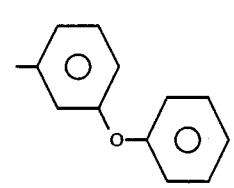 | |
| 792 | CH | F$_2$CHO | N | CH | N | CH$_2$ | H | 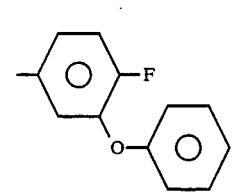 | |
| 793 | CH | F$_2$CHO | N | CH | N | CH$_2$ | H | 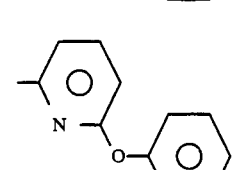 | |

TABLE 2-continued

Compounds of the formula I having $R^2$ and $R^3 = CH_2\!-\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 794 | CH | $F_2CHO$ | N | CH | N | $CH_2$ | H | phenyl-F with O-phenyl-F | |
| 795 | CH | $F_2CHO$ | N | CH | N | $CH_2$ | CN | phenyl-O-phenyl | |
| 796 | CH | $F_2CHO$ | N | CH | N | $CH_2$ | CN | phenyl-F-O-phenyl | |
| 797 | CH | $F_2CHO$ | N | CH | N | O | H | phenyl-O-phenyl | |
| 798 | CH | $F_2CHO$ | N | CH | N | O | H | phenyl-F-O-phenyl | |
| 799 | CH | $F_2CHO$ | N | CH | N | O | H | pyridyl-O-phenyl | |
| 800 | CH | $F_2CHO$ | N | CH | N | O | CN | phenyl-O-phenyl | |
| 801 | CH | $F_2CHO$ | N | CH | N | O | $CH_3$ | phenyl-O-phenyl | |

TABLE 2-continued
Compounds of the formula I having $R^2$ and $R^3 = CH_2-CH_2$; A = N, CH or $CR^1$
| Compound No. | A | $R^1$ | B | C' | D | X | $R^4$ | $R^5$ | Physical data |
|---|---|---|---|---|---|---|---|---|---|
| 802 | CH | EtS | N | CH | N | $CH_2$ | H | 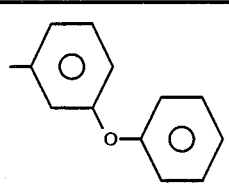 | |
| 803 | CH | EtS | N | CH | N | $CH_2$ | H | 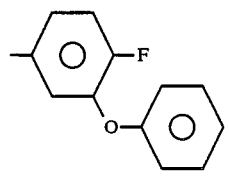 | |
| 804 | CH | EtS | N | CH | N | $CH_2$ | H | 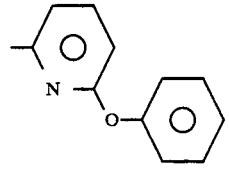 | |
| 805 | CH | EtS | N | CH | N | $CH_2$ | H | 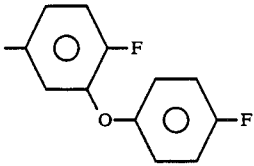 | |
| 806 | CH | EtS | N | CH | N | $CH_2$ | CN | 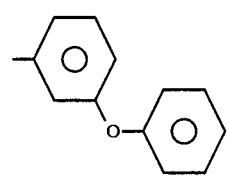 | |
| 807 | CH | EtS | N | CH | N | $CH_2$ | CN | 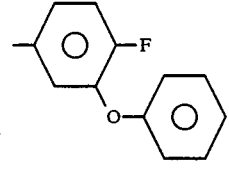 | |
| 808 | CH | EtS | N | CH | N | O | H | 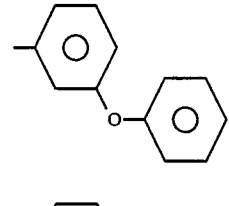 | |
| 809 | CH | EtS | N | CH | N | O | H | 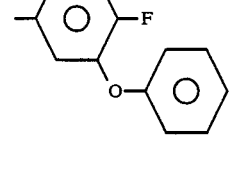 | |

TABLE 2-continued

Compounds of the formula I having $R^2$ and $R^3$ = $CH_2$—$CH_2$; A = N, CH or $CR^1$

| Compound No. | A | $R^1$ | B | C' | D | X | $R^4$ | $R^5$ | Physical data |
|---|---|---|---|---|---|---|---|---|---|
| 810 | CH | EtS | N | CH | N | O | H | 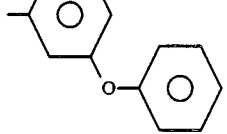 | |

TABLE 2

Compounds of the formula I having $R^2$ and $R^3$ = $CH_2$—$CH_2$; A = N, CH or $CR^1$

| Compound No. | A | $R^1$ | B | C' | D | X | $R^4$ | $R^5$ | Physical data |
|---|---|---|---|---|---|---|---|---|---|
| 811 | CH | Ets | N | CH | N | O | CN | 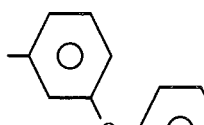 | |
| 812 | CH | Ets | N | CH | N | O | $CH_3$ | 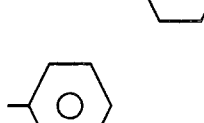 | |
| 813 | N | EtO | CH | CH | N | $CH_2$ | H | 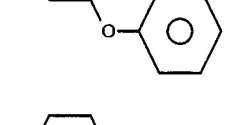 | |
| 814 | N | EtO | CH | CH | N | $CH_2$ | H | 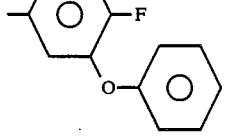 | |
| 815 | N | EtO | CH | CH | N | $CH_2$ | H | 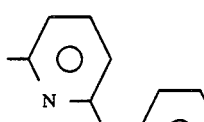 | |
| 816 | N | EtO | CH | CH | N | O | H |  | |

TABLE 2-continued
Compounds of the formula I having $R^2$ and $R^3$ = CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 817 | N | EtO | CH | CH | N | O | H | 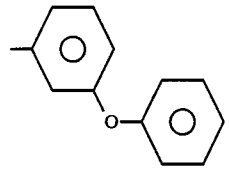 | |
| 818 | N | Cl | CH | CH | N | CH$_2$ | H | 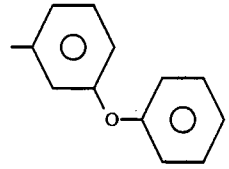 | |
| 819 | N | Cl | CH | CH | N | CH$_2$ | H | 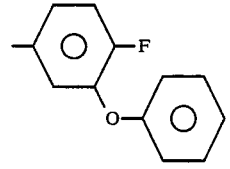 | |
| 820 | N | Cl | CH | CH | N | CH$_2$ | H | 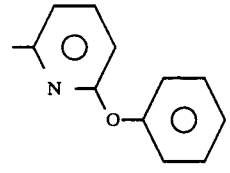 | |
| 821 | N | Cl | CH | CH | N | O | H | 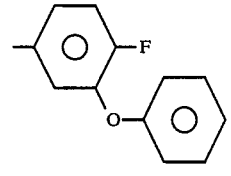 | |
| 822 | N | Cl | CH | CH | N | O | H | 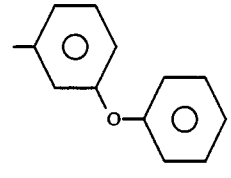 | |
| 823 | N | CH$_3$O | CH | CH | N | CH$_2$ | H | 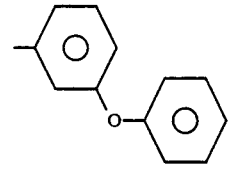 | |
| 824 | N | CH$_3$O | CH | CH | N | CH$_2$ | H | 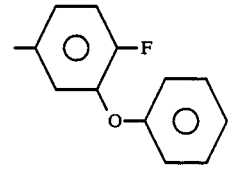 | |

TABLE 2-continued

Compounds of the formula I having $R^2$ and $R^3 =$ CH$_2$—CH$_2$; A = N, CH or CR$^1$

| Compound No. | A | R$^1$ | B | C' | D | X | R$^4$ | R$^5$ | Physical data |
|---|---|---|---|---|---|---|---|---|---|
| 825 | N | CH$_3$O | CH | CH | N | CH$_2$ | H | | |
| 826 | N | CH$_3$O | CH | CH | N | O | H | | |
| 827 | N | CH$_3$O | CH | CH | N | O | H | | |
| 828 | N | EtS | CH | CH | N | CH$_2$ | H | | |
| 829 | N | EtS | CH | CH | N | CH$_2$ | H | | |
| 830 | N | EtS | CH | CH | N | CH$_2$ | H | | |
| 831 | N | EtS | CH | CH | N | O | H | | |
| 832 | N | EtS | CH | CH | N | O | H | | |

TABLE 2-continued

Compounds of the formula I having $R^2$ and $R^3 = CH_2\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 833 | CCl | EtO | N | N | CH | $CH_2$ | H | phenoxy-phenyl | |
| 834 | CCl | EtO | N | N | CH | $CH_2$ | H | (2-F-phenoxy)-phenyl | |
| 835 | CCl | EtO | N | N | CH | $CH_2$ | H | (phenoxy)-pyridinyl | |
| 836 | CCl | EtO | N | N | CH | O | H | (2-F-phenoxy)-phenyl | |
| 837 | CCl | EtO | N | N | CH | O | H | phenoxy-phenyl | |
| 838 | CCl | Cl | N | N | CH | $CH_2$ | H | phenoxy-phenyl | |
| 839 | CCl | Cl | N | N | CH | $CH_2$ | H | (2-F-phenoxy)-phenyl | |
| 840 | CCl | Cl | N | N | CH | $CH_2$ | H | (phenoxy)-pyridinyl | |

TABLE 2-continued
Compounds of the formula I having $R^2$ and $R^3 = CH_2$—$CH_2$; A = N, CH or $CR^1$
| Compound No. | A | $R^1$ | B | C' | D | X | $R^4$ | $R^5$ | Physical data |
|---|---|---|---|---|---|---|---|---|---|
| 841 | CCl | Cl | N | N | CH | O | H | 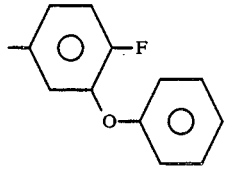 | |
| 842 | CCl | Cl | N | N | CH | O | H | 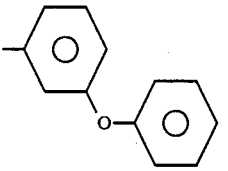 | |
| 843 | CH | EtO | CH | N | N | $CH_2$ | H | 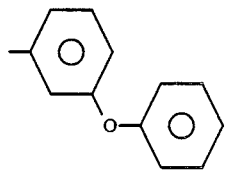 | |
| 844 | CH | EtO | CH | N | N | $CH_2$ | H | 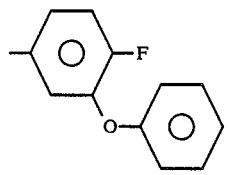 | |
| 845 | CH | EtO | CH | N | N | $CH_2$ | H | 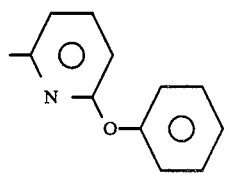 | |
| 846 | CH | EtO | CH | N | N | O | H | 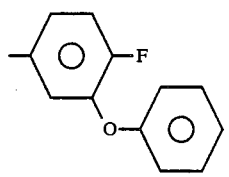 | |
| 847 | CH | EtO | CH | N | N | O | H | 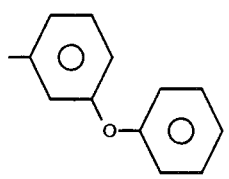 | |
| 848 | CH | $CH_3O$ | CH | N | N | $CH_2$ | H | 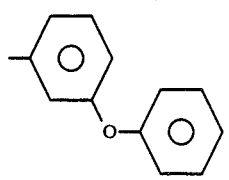 | |

TABLE 2-continued
Compounds of the formula I having $R^2$ and $R^3 = CH_2\!\!-\!\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 849 | CH | $CH_3O$ | CH | N | N | $CH_2$ | H | 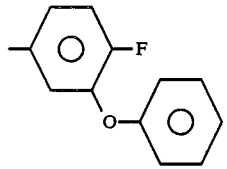 | |
| 850 | CH | $CH_3O$ | CH | N | N | $CH_2$ | H | 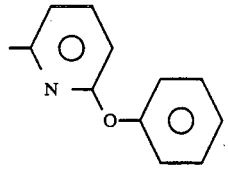 | |
| 851 | CH | $CH_3O$ | CH | N | N | O | H | 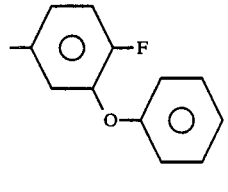 | |
| 852 | CH | $CH_3O$ | CH | N | N | O | H | 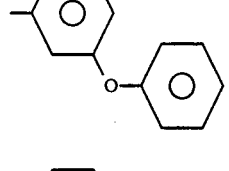 | |
| 853 | CH | Cl | CH | N | N | $CH_2$ | H | 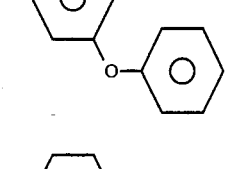 | |
| 854 | CH | Cl | CH | N | N | $CH_2$ | H | 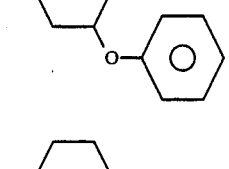 | |
| 855 | CH | Cl | CH | N | N | $CH_2$ | H | 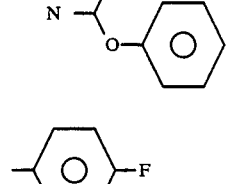 | |
| 856 | CH | Cl | CH | N | N | O | H | 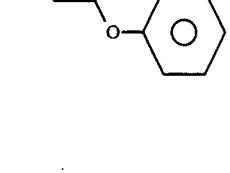 | |

TABLE 2-continued
Compounds of the formula I having $R^2$ and $R^3 = CH_2\!\!-\!\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 857 | CH | Cl | CH | N | N | O | H | 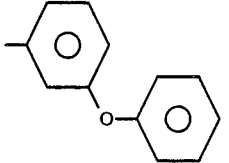 | |
| 858 | CH | EtS | CH | N | N | $CH_2$ | H | 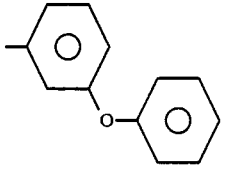 | |
| 859 | CH | EtS | CH | N | N | $CH_2$ | H | 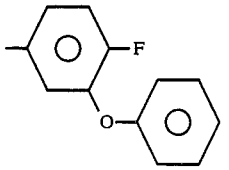 | |
| 860 | CH | EtS | CH | N | N | $CH_2$ | H | 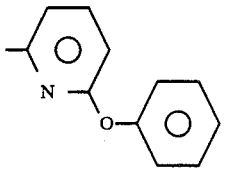 | |
| 861 | CH | EtS | CH | N | N | O | H | 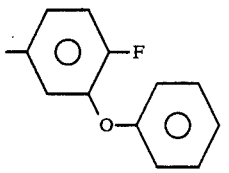 | |
| 862 | CH | EtS | CH | N | N | O | H | 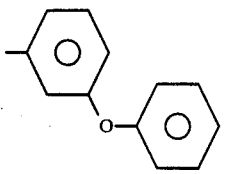 | |
| 863 | CCl | Cl | CH | N | N | $CH_2$ | H | 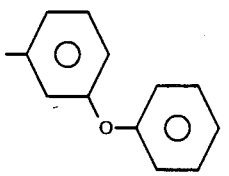 | |
| 864 | CCl | Cl | CH | N | N | $CH_2$ | H | 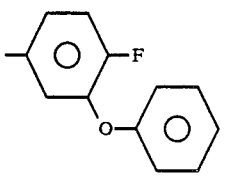 | |

TABLE 2-continued

Compounds of the formula I having $R^2$ and $R^3$ = CH$_2$—CH$_2$; A = N, CH or CR$^1$

| Compound No. | A | $R^1$ | B | C' | D | X | $R^4$ | $R^5$ | Physical data |
|---|---|---|---|---|---|---|---|---|---|
| 865 | CCl | Cl | CH | N | N | CH$_2$ | H | (pyridyl-O-phenyl) | |
| 866 | CCl | CH | N | N | O | H | | (fluorophenyl-O-phenyl) | |
| 867 | CCl | Cl | CH | N | N | O | H | (phenyl-O-phenyl) | |
| 868 | CH | EtO | N | N | N | CH$_2$ | H | (phenyl-O-phenyl) | |
| 869 | CH | EtO | N | N | N | CH$_2$ | H | (fluorophenyl-O-phenyl) | |
| 870 | CH | EtO | N | N | N | CH$_2$ | H | (pyridyl-O-phenyl) | |
| 871 | CH | EtO | N | N | N | O | H | (fluorophenyl-O-phenyl) | |
| 872 | CH | EtO | N | N | N | O | H | (phenyl-O-phenyl) | |

TABLE 2-continued

Compounds of the formula I having $R^2$ and $R^3 = \underset{\diagdown\diagup}{CH_2\text{—}CH_2}$; A = N, CH or $CR^1$

| Compound No. | A | $R^1$ | B | C' | D | X | $R^4$ | $R^5$ | Physical data |
|---|---|---|---|---|---|---|---|---|---|
| 873 | CH | $CH_3O$ | N | N | N | $CH_2$ | H | –C₆H₄–O–C₆H₅ | |
| 874 | CH | $CH_3O$ | N | N | N | $CH_2$ | H | –C₆H₄(F)–O–C₆H₅ | |
| 875 | CH | $CH_3O$ | N | N | N | $CH_2$ | H | –(pyridyl)–O–C₆H₅ | |
| 876 | CH | $CH_3O$ | N | N | N | O | H | –C₆H₄(F)–O–C₆H₅ | |
| 877 | CH | $CH_3O$ | N | N | N | O | H | –C₆H₄–O–C₆H₅ | |
| 878 | CH | Cl | N | N | N | $CH_2$H | | –C₆H₄–O–C₆H₅ | |
| 879 | CH | Cl | N | N | N | $CH_2$ | H | –C₆H₄(F)–O–C₆H₅ | |
| 880 | CH | Cl | N | N | N | $CH_2$ | H | –(pyridyl)–O–C₆H₅ | |

TABLE 2-continued

Compounds of the formula I having $R^2$ and $R^3$ = $CH_2\text{—}CH_2$; A = N, CH or $CR^1$

| Compound No. | A | $R^1$ | B | C' | D | X | $R^4$ | $R^5$ | Physical data |
|---|---|---|---|---|---|---|---|---|---|
| 881 | CH | Cl | N | N | N | O | H | (phenyl-O-phenyl, F substituted) | |
| 882 | CH | Cl | N | N | N | O | H | (phenyl-O-phenyl) | |
| 883 | CH | EtS | N | N | N | $CH_2$ | H | (phenyl-O-phenyl) | |
| 884 | CH | EtS | N | N | N | $CH_2$ | H | (phenyl-O-phenyl, F substituted) | |
| 885 | CH | EtS | N | N | N | $CH_2$ | H | (pyridyl-O-phenyl) | |
| 886 | CH | EtS | N | N | N | O | H | (phenyl-O-phenyl, F substituted) | |
| 887 | CH | EtS | N | N | N | O | H | (phenyl-O-phenyl) | |
| 888 | N | EtS | N | N | N | $CH_2$ | H | (phenyl-O-phenyl) | |

TABLE 2-continued
Compounds of the formula I having R² and R³ = CH₂—CH₂; A = N, CH or CR¹
| Compound No. | A | R¹ | B | C' | D | X | R⁴ | R⁵ | Physical data |
|---|---|---|---|---|---|---|---|---|---|
| 889 | N | EtO | N | N | CH | CH₂ | H | 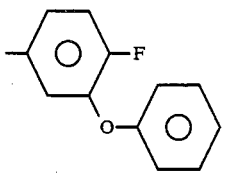 | |
| 890 | N | EtO | N | N | CH | CH₂ | H | 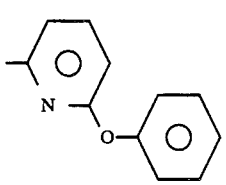 | |
| 891 | N | EtO | N | N | N | O | H | 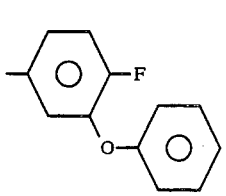 | |
| 892 | N | EtO | N | N | CH | O | H | 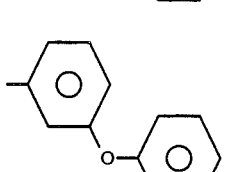 | |
| 893 | N | CH₃O | N | N | CH | CH₂ | H | 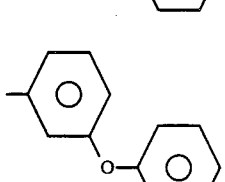 | |
| 894 | N | CH₃O | N | N | CH | CH₂ | H | 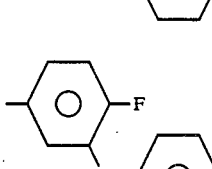 | |
| 895 | N | CH₃O | N | N | CH | CH₂ | H | 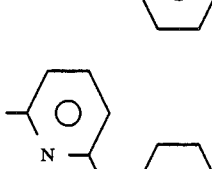 | |
| 896 | N | CH₃O | N | N | CH | O | H | 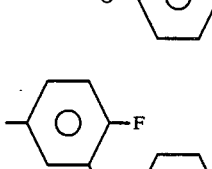 | |

TABLE 2-continued

Compounds of the formula I having $R^2$ and $R^3 = \underset{\diagdown\diagup}{CH_2-CH_2}$; A = N, CH or $CR^1$

| Compound No. | A | $R^1$ | B | C' | D | X | $R^4$ | $R^5$ | Physical data |
|---|---|---|---|---|---|---|---|---|---|
| 897 | N | CH$_3$O | N | N | CH | O | H | (4-phenoxyphenyl) | |
| 898 | N | Cl | N | N | CH | CH$_2$ | H | (4-phenoxyphenyl) | |
| 899 | N | Cl | N | N | CH | CH$_2$ | H | (2-fluoro-4-phenoxyphenyl) | |
| 900 | N | Cl | N | N | CH | CH$_2$ | H | (6-phenoxypyridin-3-yl) | |
| 901 | N | Cl | N | N | CH | O | H | (2-fluoro-4-phenoxyphenyl) | |
| 902 | N | Cl | N | N | CH | O | H | (4-phenoxyphenyl) | |
| 903 | N | EtS | N | N | CH | CH$_2$ | H | (4-phenoxyphenyl) | |
| 904 | N | EtS | N | N | CH | CH$_2$ | H | (2-fluoro-4-phenoxyphenyl) | |

TABLE 2-continued
Compounds of the formula I having $R^2$ and $R^3$ = $CH_2$—$CH_2$; A = N, CH or $CR^1$
| Compound No. | A | $R^1$ | B | C' | D | X | $R^4$ | $R^5$ | Physical data |
|---|---|---|---|---|---|---|---|---|---|
| 905 | N | EtS | N | N | CH | $CH_2$ | H | 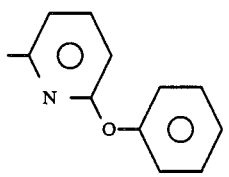 | |
| 906 | N | EtS | N | N | CH | O | H | 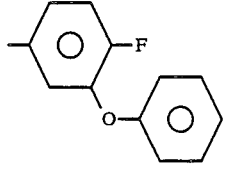 | |
| 907 | N | EtS | N | N | CH | O | H | 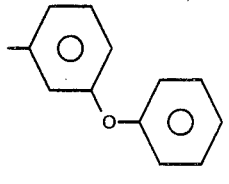 | |
| 908 | N | EtO | N | N | N | $CH_2$ | H | 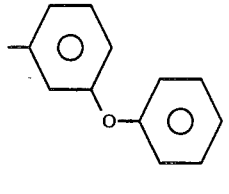 | |
| 909 | N | EtO | N | N | N | $CH_2$ | H | 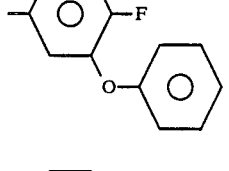 | |
| 910 | N | EtO | N | N | N | $CH_2$ | H | 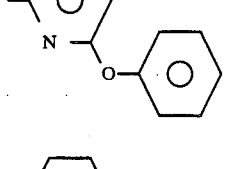 | |
| 911 | N | EtO | N | N | N | O | H | 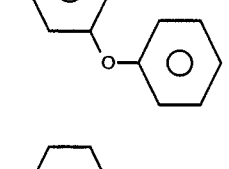 | |
| 912 | N | EtO | N | N | N | O | H | 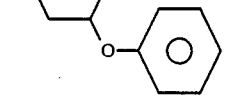 | |

TABLE 2-continued

Compounds of the formula I having $R^2$ and $R^3 = CH_2\!\!-\!\!CH_2$; A = N, CH or $CR^1$

| Compound No. | A | $R^1$ | B | C' | D | X | $R^4$ | $R^5$ | Physical data |
|---|---|---|---|---|---|---|---|---|---|
| 913 | N | $CH_3O$ | N | N | N | $CH_2$ | H | phenoxyphenyl | |
| 914 | N | $CH_3O$ | N | N | N | $CH_2$ | H | (fluorophenoxy)phenyl | |
| 915 | N | $CH_3O$ | N | N | N | $CH_2$ | H | (phenoxy)pyridyl | |
| 916 | N | $CH_3O$ | N | N | N | O | H | (fluorophenoxy)phenyl | |
| 917 | N | $CH_3O$ | N | N | N | O | H | phenoxyphenyl | |
| 918 | N | Cl | N | N | N | $CH_2$ | H | phenoxyphenyl | |
| 919 | N | Cl | N | N | N | $CH_2$ | H | (fluorophenoxy)phenyl | |
| 920 | N | Cl | N | N | N | $CH_2$ | H | (phenoxy)pyridyl | |

TABLE 2-continued
Compounds of the formula I having $R^2$ and $R^3$ = $CH_2$—$CH_2$; A = N, CH or $CR^1$
| Compound No. | A | $R^1$ | B | C' | D | X | $R^4$ | $R^5$ | Physical data |
|---|---|---|---|---|---|---|---|---|---|
| 921 | N | Cl | N | N | N | O | H | 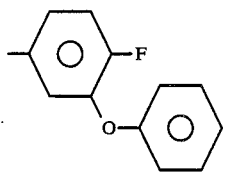 | |
| 923 | N | Cl | N | N | N | O | H | 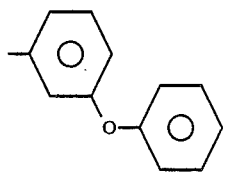 | |
| 924 | N | EtS | N | N | N | $CH_2$ | H | 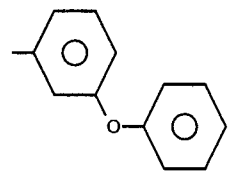 | |
| 925 | N | EtS | N | N | N | $CH_2$ | H | 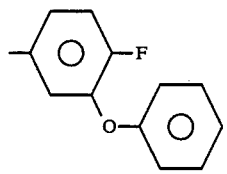 | |
| 926 | N | EtS | N | N | N | $CH_2$ | H | 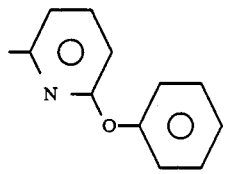 | |
| 927 | N | EtS | N | N | N | O | H | 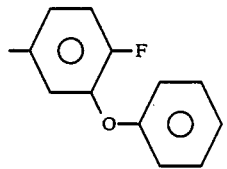 | |
| 928 | N | EtS | N | N | N | O | H | 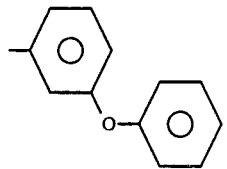 | |
| 929 | N | $F_3C$—$CH_2$—O— | CH | CH | CH | $CH_2$ | H | 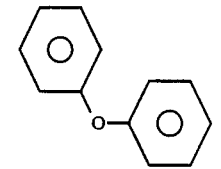 | |

TABLE 2-continued

Compounds of the formula I having $R^2$ and $R^3$ = CH$_2$—CH$_2$; A = N, CH or CR$^1$

| Compound No. | A | R$^1$ | B | C' | D | X | R$^4$ | R$^5$ | Physical data |
|---|---|---|---|---|---|---|---|---|---|
| 930 | N | F$_3$C—CH$_2$—O— | CH | CH | CH | CH$_2$ | H | 2-fluorophenoxyphenyl | |
| 931 | N | F$_3$C—CH$_2$—O— | CH | CH | CH | CH$_2$ | H | (pyridinyl)oxyphenyl | |
| 932 | N | F$_3$C—CH$_2$—O— | CH | CH | CH | CH$_2$ | H | (thienyl)oxyphenyl | |
| 933 | N | F$_3$C—CH$_2$—O— | CH | CH | CH | CH$_2$ | H | 2-fluorophenoxy-4-fluorophenyl | |
| 934 | N | F$_3$C—CH$_2$—O— | CH | CH | CH | O | H | phenoxyphenyl | |
| 935 | N | F$_3$C—CH$_2$—O— | CH | CH | CH | O | H | 2-fluorophenoxyphenyl | |
| 936 | N | F$_3$C—CH$_2$—O— | CH | CH | CH | O | H | (pyridinyl)oxyphenyl | |
| 937 | CH | F$_3$C—CH$_2$—O— | N | CH | CH | CH$_2$ | H | phenoxyphenyl | |

TABLE 2-continued
Compounds of the formula I having $R^2$ and $R^3 = $ CH$_2$—CH$_2$; A = N, CH or CR$^1$
| Compound No. | A | R$^1$ | B | C' | D | X | R$^4$ | R$^5$ | Physical data |
|---|---|---|---|---|---|---|---|---|---|
| 938 | CH | F$_3$C—CH$_2$—O— | N | CH | CH | CH$_2$ | H | 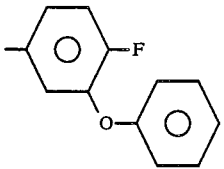 | |
| 939 | CH | F$_3$C—CH$_2$—O— | N | CH | CH | CH$_2$ | H | 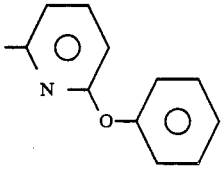 | |
| 940 | CH | F$_3$C—CH$_2$—O— | N | CH | CH | CH$_2$ | H | 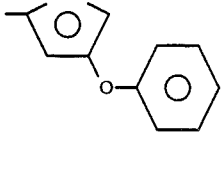 | |
| 941 | CH | F$_3$C—CH$_2$—O— | N | CH | CH | CH$_2$ | H | 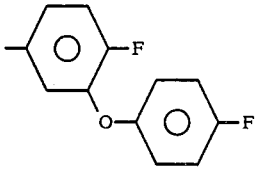 | |
| 942 | CH | F$_3$C—CH$_2$—O— | N | CH | CH | O | H | 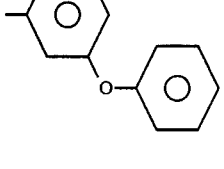 | |
| 943 | CH | F$_3$C—CH$_2$—O— | N | CH | CH | O | H | 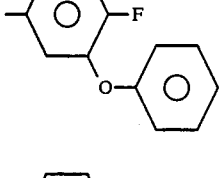 | |
| 944 | CH | F$_3$C—CH$_2$—O— | N | CH | CH | O | H | 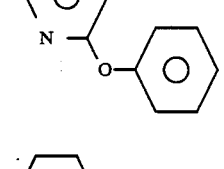 | |
| 945 | N | F$_3$C—CH$_2$—O— | CH | N | CH | CH$_2$ | H | 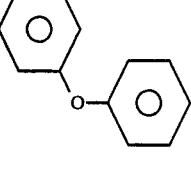 | |

TABLE 2-continued
Compounds of the formula I having $R^2$ and $R^3 = CH_2-CH_2$; $A = N$, CH or $CR^1$
| Compound No. | A | $R^1$ | B | C' | D | X | $R^4$ | $R^5$ | Physical data |
|---|---|---|---|---|---|---|---|---|---|
| 946 | N | $F_3C-CH_2-O-$ | CH | N | CH | $CH_2$ | H | 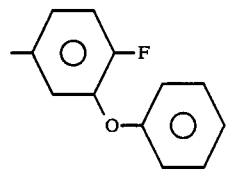 | |
| 947 | N | $F_3C-CH_2-O-$ | CH | N | CH | $CH_2$ | H | 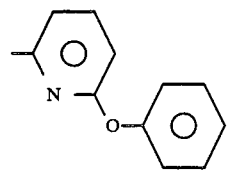 | |
| 948 | N | $F_3C-CH_2-O-$ | CH | N | CH | $CH_2$ | H | 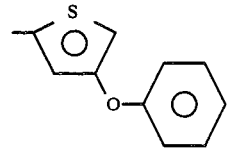 | |
| 949 | N | $F_3C-CH_2-O-$ | CH | N | CH | $CH_2$ | H | 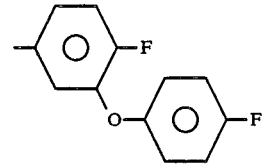 | |
| 950 | N | $F_3C-CH_2-O-$ | CH | N | CH | O | H | 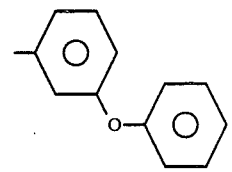 | |
| 951 | N | $F_3C-CH_2-O-$ | CH | N | CH | O | H | 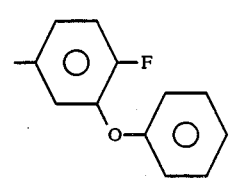 | |
| 952 | N | $F_3C-CH_2-O-$ | CH | N | CH | O | H | 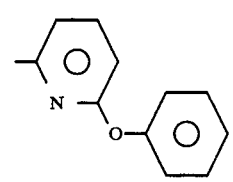 | |
| 953 | CH | $F_3C-CH_2-O-$ | N | CH | N | $CH_2$ | H | 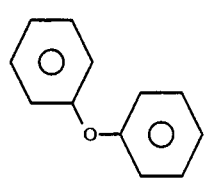 | |

TABLE 2-continued
Compounds of the formula I having $R^2$ and $R^3 = \underset{\diagdown\diagup}{CH_2-CH_2}$; A = N, CH or $CR^1$
| Compound No. | A | $R^1$ | B | C' | D | X | $R^4$ | $R^5$ | Physical data |
|---|---|---|---|---|---|---|---|---|---|
| 954 | CH | $F_3C-CH_2-O-$ | N | CH | N | $CH_2$ | H | 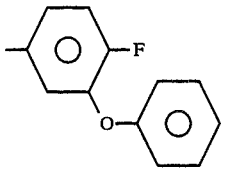 | |
| 955 | CH | $F_3C-CH_2-O-$ | N | CH | N | $CH_2$ | H | 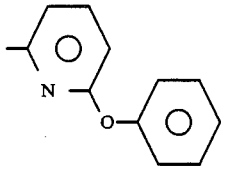 | |
| 956 | CH | $F_3C-CH_2-O-$ | N | CH | N | $CH_2$ | H | 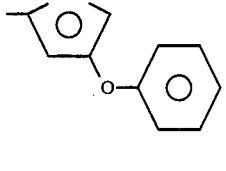 | |
| 957 | CH | $F_3C-CH_2-O-$ | N | CH | N | $CH_2$ | H | 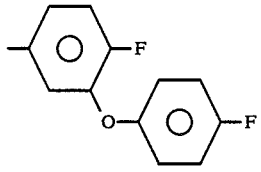 | |
| 958 | CH | $F_3C-CH_2-O-$ | N | CH | N | O | H | 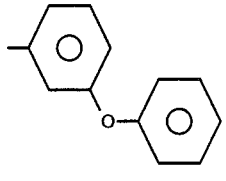 | |
| 959 | CH | $F_3C-CH_2-O-$ | N | CH | N | O | H | 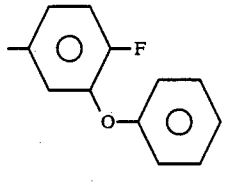 | |
| 960 | CH | $F_3C-CH_2-O-$ | N | CH | N | O | H | 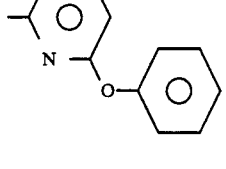 | |
| 961 | N | $F_3C-CH_2-O-$ | N | CH | CH | $CH_2$ | H | 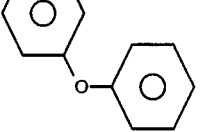 | |

TABLE 2-continued
Compounds of the formula I having $R^2$ and $R^3$ = $CH_2\!\!-\!\!CH_2$; A = N, CH or $CR^1$
| Compound No. | A | $R^1$ | B | C' | D | X | $R^4$ | $R^5$ | Physical data |
|---|---|---|---|---|---|---|---|---|---|
| 962 | N | $F_3C-CH_2-O-$ | N | CH | CH | $CH_2$ | H | 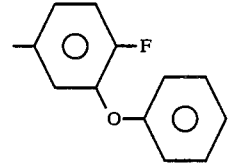 | |
| 963 | N | $F_3C-CH_2-O-$ | N | CH | CH | $CH_2$ | H | 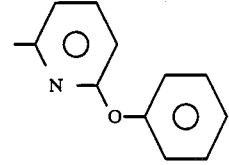 | |
| 964 | N | $F_3C-CH_2-O-$ | N | CH | CH | $CH_2$ | H | 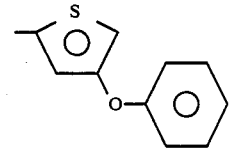 | |
| 965 | N | $F_3C-CH_2-O-$ | N | CH | CH | $CH_2$ | H | 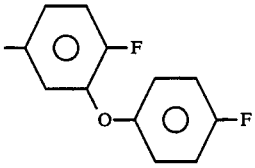 | |
| 966 | N | $F_3C-CH_2-O-$ | N | CH | CH | O | H | 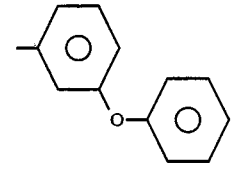 | |
| 967 | N | $F_3C-CH_2-O-$ | N | CH | CH | O | H | 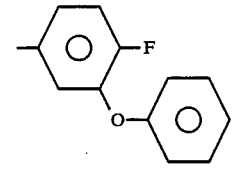 | |
| 968 | N | $F_3C-CH_2-O-$ | N | CH | CH | O | H | 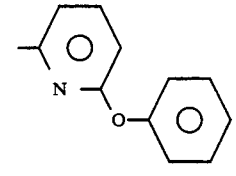 | |
| 969 | N | $F_3C-CH_2-O-$ | CH | CH | N | $CH_2$ | H | 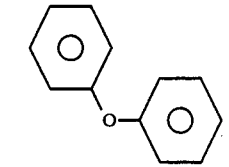 | |

TABLE 2-continued
Compounds of the formula I having $R^2$ and $R^3 = \underset{\diagdown \ \diagup}{CH_2-CH_2}$; A = N, CH or $CR^1$
| Compound No. | A | $R^1$ | B | C' | D | X | $R^4$ | $R^5$ | Physical data |
|---|---|---|---|---|---|---|---|---|---|
| 970 | N | $F_3C-CH_2-O-$ | CH | CH | N | $CH_2$ | H | 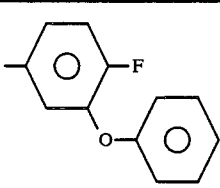 | |
| 971 | N | $F_3C-CH_2-O-$ | CH | CH | N | $CH_2$ | H | 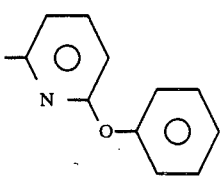 | |
| 972 | N | $F_3C-CH_2-O-$ | CH | CH | N | $CH_2$ | H | 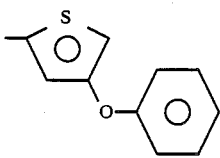 | |
| 973 | N | $F_3C-CH_2-O-$ | CH | CH | N | $CH_2$ | H | 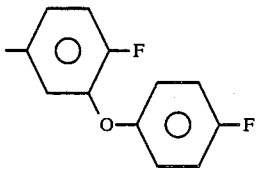 | |
| 974 | N | $F_3C-CH_2-O-$ | CH | CH | N | O | H | 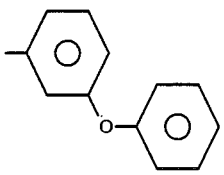 | |
| 975 | N | $F_3C-CH_2-O-$ | CH | CH | N | O | H | 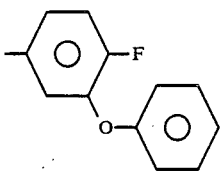 | |
| 976 | N | $F_3C-CH_2-O-$ | CH | CH | N | O | H | 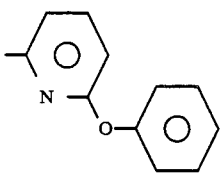 | |
| 977 | N | $F_3C-CH_2-O-$ | N | N | CH | $CH_2$ | | 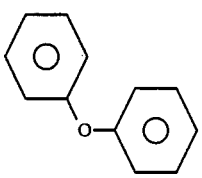 | |

TABLE 2-continued
Compounds of the formula I having $R^2$ and $R^3 = CH_2-CH_2$; A = N, CH or $CR^1$
| Compound No. | A | $R^1$ | B | C' | D | X | $R^4$ | $R^5$ | Physical data |
|---|---|---|---|---|---|---|---|---|---|
| 978 | N | $F_3C-CH_2-O-$ | N | N | CH | $CH_2$ | H | 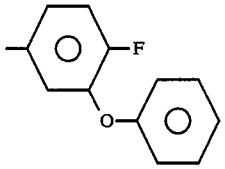 | |
| 979 | N | $F_3C-CH_2-O-$ | N | N | CH | $CH_2$ | H | 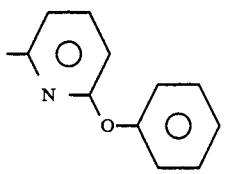 | |
| 980 | N | $F_3C-CH_2-O-$ | N | N | CH | $CH_2$ | H | 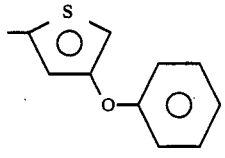 | |
| 981 | N | $F_3C-CH_2-O-$ | N | N | CH | $CH_2$ | H | 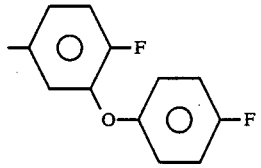 | |
| 982 | N | $F_3C-CH_2-O-$ | N | N | CH | O | H | 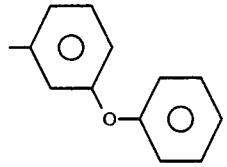 | |
| 983 | N | $F_3C-CH_2-O-$ | N | N | CH | O | H | 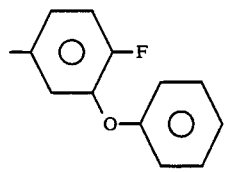 | |
| 984 | N | $F_3C-CH_2-O-$ | N | N | CH | O | H | 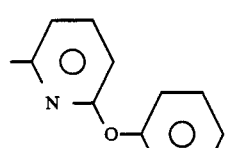 | |
| 985 | N | $F_3C-CH_2-O-$ | N | CH | N | $CH_2$ | | 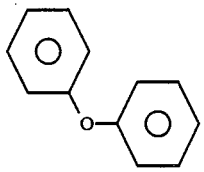 | |

TABLE 2-continued
Compounds of the formula I having $R^2$ and $R^3$ = CH$_2$—CH$_2$; A = N, CH or CR$^1$
| Compound No. | A | $R^1$ | B | C' | D | X | $R^4$ | $R^5$ | Physical data |
|---|---|---|---|---|---|---|---|---|---|
| 986 | N | F$_3$C—CH$_2$—O— | N | CH | N | CH$_2$ | H | 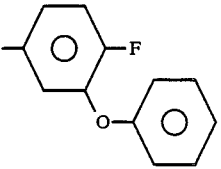 | |
| 987 | N | F$_3$C—CH$_2$—O— | N | CH | N | CH$_2$ | H | 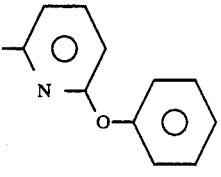 | |
| 988 | N | F$_3$C—CH$_2$—O— | N | CH | N | CH$_2$ | H | 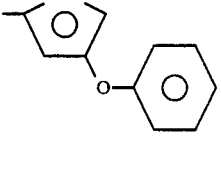 | |
| 989 | N | F$_3$C—CH$_2$—O— | N | CH | N | CH$_2$ | H | 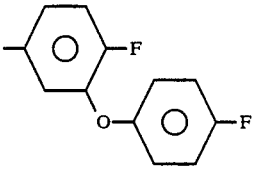 | |
| 990 | N | F$_3$C—CH$_2$—O— | N | CH | N | O | H | 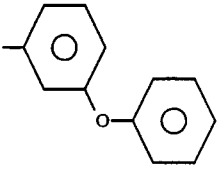 | |
| 991 | N | F$_3$C—CH$_2$—O— | N | CH | N | O | H | 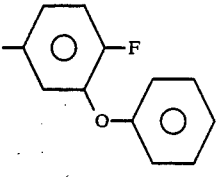 | |
| 992 | N | F$_3$C—CH$_2$—O— | N | CH | N | O | H | 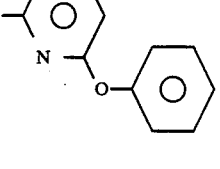 | |
| 993 | N | F$_3$C—CH$_2$—O— | N | N | N | CH$_2$ | H | 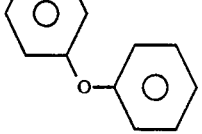 | |

TABLE 2-continued

Compounds of the formula I having $R^2$ and $R^3 = \underset{\diagdown \diagup}{CH_2-CH_2}$; A = N, CH or $CR^1$

| Compound No. | A | $R^1$ | B | C' | D | X | $R^4$ | $R^5$ | Physical data |
|---|---|---|---|---|---|---|---|---|---|
| 994 | N | $F_3C-CH_2-O-$ | N | N | N | $CH_2$ | H | 2-F-phenoxyphenyl | |
| 995 | N | $F_3C-CH_2-O-$ | N | N | N | $CH_2$ | H | pyridinyloxyphenyl | |
| 996 | N | $F_3C-CH_2-O-$ | N | N | N | $CH_2$ | H | thienyloxyphenyl | |
| 997 | N | $F_3C-CH_2-O-$ | N | N | N | $CH_2$ | H | 2-F-phenoxy-4-F-phenyl | |
| 998 | N | $F_3C-CH_2-O-$ | N | N | N | O | H | phenoxyphenyl | |
| 999 | N | $F_3C-CH_2-O-$ | N | N | N | O | H | 2-F-phenoxyphenyl | |
| 1000 | N | $F_3C-CH_2-O-$ | N | N | N | O | H | pyridinyloxyphenyl | |

C. BIOLOGICAL EXAMPLES

EXAMPLE 1

Broad beans (*Vicia faba*) strongly infested with cowpea aphid (*Aphis craccivora*) were sprayed with aqueous dilutions of emulsion concentrates having active compound contents of 1,000 ppm until the stage of the onset of dripping. After 3 days, the mortality was in each case 100% in the preparations containing the active compounds of Examples 1, 2, 5, 8, 9, 18, 19, 41, 199, 200, 205, 206, 232, 238, 239, 312, 342, 343, 357, 424, 425, 429, 430, 440, 441, 445, 446, 462, 497, 503, 504 and 513.

EXAMPLE 2

Bean plants (*Phaseolus vulgaris*) heavily infested with the glasshouse whitefly (*Trialeurodes Vaporarium*) were sprayed with aqueous dilutions of emulsion concentrates (1,000 ppm active compound content) until the onset of dripping. After placing the plants in a greenhouse, microscopic examination took place after 14 days, with the result in each case of 100% mortality in the preparations containing the active compounds of Examples 2, 8, 9, 18, 206, 239, 424, 425, 429, 430, 440, 441, 445, 446 and 503.

EXAMPLE 3

Test procedure: analogous to Example 2
Test animal: *Tetranychus urticae* (glasshouse red spider mite)
Test plants: *Phaseolus vulgaris* (dwarf bean)
Application rate: 1,000 ppm active compound in the spraying liquor
The activity determined after 8 days resulted in 100% mortality for the compounds 425, 429, 430, 445 and 446.

EXAMPLE 4

Bean plants (*Phaseolus vulgaris*) heavily infested by the citrus mealybug (*Pseudococcus citri*) were sprayed with aqeuous dilutions of emulsion concentrates (in each case 1,000 ppm active compound in the spraying liquor) up to the stage of the onset of dripping.
After a standing time of 7 days in a greenhouse, examination took place at 20°–25° C.
100% mortality was established for the compounds according to Examples 2, 5, 8, 9, 18, 19, 41, 200, 205, 206, 238, 342, 424, 429, 430, 446, 503 and 504.

EXAMPLE 5

Large milkweed bugs (*Oncopeltus fasciatus*) were treated with aqueous dilutions of emulsion concentrates (in each case 1,000 ppm of active compound in the spraying liquor) of active compounds from Examples 2, 9, 19, 206, 425, 430, 441, 446 and 504. The bugs were subsequently placed in containers provided with air-permeable lids at room temperature.
The mortality was determined 5 days after the treatment and amounted to 100% in each individual case.

EXAMPLE 6

The bottom insides of Petri dishes coated with synthetic nutrient were sprayed with 3 ml in each case of an aqueous emulsion containing 2,000 ppm of active compound after solidification of the feed paste. After drying of the spray coating and introduction of 10 larvae of the common cotton worm (*Prodenia litura*), the dishes were stored for 7 days at 21° C. and the degree of action of the respective compound was then determined (expressed in % mortality). The compounds 1, 2, 5, 8, 9, 18, 19, 41, 200, 205, 206, 239, 424, 425, 430, 445, 446, 503 and 504 produced an activity of 100% in each case in this test.

EXAMPLE 7

Bean leaves (*Phaseolus vulgaris*) were treated with an aqueous emulsion of the compound from Example 1 in a concentration of 1,000 ppm (with respect to active compound) and placed in observation cages with identically treated larvae of the Mexican bean beetle (*Epilachna varivestis*). An analysis after 48 hours showed 100% destruction of the test animals. The compounds according to Examples 2, 8, 9, 18, 19, 41, 200, 206, 239, 342, 424, 425, 429, 430, 441, 445, 446, 497, 503 and 504 proved to be equally active.

EXAMPLE 8

1 ml of the active compound from Example 1 in acetone having a concentration of 1,000 ppm was uniformly applied to the inner side of the lid and bottom of a Petri dish by means of a pipette and the dishes were left open until the solvent had completely evaporated. 10 house flies (*Musca domestica*) each were then placed in the Petri dishes, the dishes were closed with the lids and after 3 hours a 100% destruction of the test animals was determined. The compounds according to Examples 2, 8, 9, 18, 19, 41, 200, 206, 238, 312, 424, 425, 429, 430, 440, 441, 445, 446, 503, 504 and 513 proved to be equally active.

EXAMPLE 9

1 ml in each case of an active compound solution in acetone having a concentration of 2,000 ppm was uniformly applied to the inner side of the lid and the bottom of a Petri dish with the aid of a pipette. After complete evaporation of the solvent, 10 larvae (L4) of the German cockroach (*Blatella germanica*) were placed in each Petri dish and the dishes were closed with lids. After 72 hours, the action (expressed in % mortality) was determined. The compounds 1, 2, 8, 9, 18, 19, 41, 200, 206, 239, 312, 424, 425, 429, 430, 441, 446, 503, 504 and 513 showed activity of 100% in each case in this test.

We claim:
1. A compound of formula I, and stereoisomers thereof,

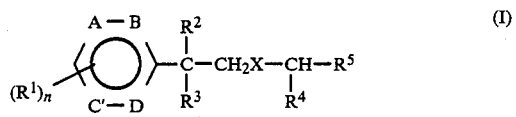

wherein:
One of A, B, C' or D is N and the remaining groups are CH
X is oxygen;
$R^1$ is a radical bonded to a carbon atom selected from the group consisting of H, $(C_1-C_4)$-alkyl, $(C_2-C_4)$alkenyl, $(C_2-C_6)$-alkynyl, $(C_3-C_7)$cycloalkyl, phenyl, phenoxy, $(C_1-C_5)$alkoxy, $(C_2-C_4)$alkenyloxy, $(C_2-C_4)$alkynyloxy, $(C_1-C_4)$alkylthio, $(C_3-C_7)$cycloalkyloxy, $(C_1-C_4)$halogenoalkyl, $(C_1-C_4)$alkoxy$(C_1-C_4)$alkyl, $(C_1-C_3)$halogenoalkoxy, $(C_1-C_3)$halogenoalkylthio, halogeno$(C_1-C_4)$alkoxy$(C_1-C_4)$alkyl, $(C_1-C_4)$alkylthio$(C_1-C_4)$alkyl, $(C_1-C_4)$alkoxy$(C_1-C_4)$alkoxy, halogeno$(C_1-C_4)$alkoxy$(C_1-C_4)$alkoxy, $(C_2-C_4)$alkenyloxy$(C_1-C_4)$alkoxy, halogeno$(C_2-C_4)$alkenyloxy, $(C_1-C_4)$alkoxy$(C_1-C_4)$alkylthio, $(C_1-C_4)$alkylthio$(C_1-C_4)$alkoxy and $(C_1-C_4)$alkylthio$(C_1-C_4)$alkylthio;
$R^2$ and $R^3$ are the same or different and each is $(C_1-C_3)$alkyl, $(C_2-C_8)$alkenyl or phenyl; or $R^2$ and $R^3$ are joined to form an alkylene chain which—together with the quaternary carbon atom to which $R^2$ and $R^3$ are attached—form an unsubstituted ring having three members;
$R^4$ is —H, F, —CCl$_3$, —C≡CH, $(C_1-C_4)$alkyl or —C(=S)NH$_2$;
$R^5$ is pyridyl or substituted phenyl; and n is 1 or 2.

2. A compound as recited in claim 1, wherein A is N, each of B, C, and D is CH, n is 1, $R^1$ is 6-$F_3C$—$CH_2$—O—, $R^2$ and $R^3$ are joined to form an ethylene chain which—together with the quaternary carbon atom to which $R^2$ and $R^3$ are attached—form an unsubstituted three-member ring, X is O, $R^4$ is hydrogen and $R^5$ is

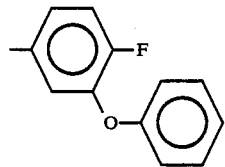

3. A compound as recited in claim 1, wherein $R^5$ is substituted phenyl.

4. A compound as recited in claim 1, wherein A is N, each of B, C, and D is CH, n is 1, $R^1$ is 6-$F_3C$—$CH_2$—O—, $R^2$ and $R^3$ are both $CH_3$, X is O, $R^4$ is hydrogen and $R^5$ is

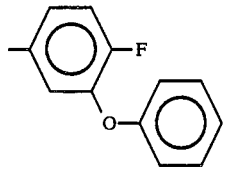

5. An insecticidal or acaricidal agent which contains an insecticidally or acaricidally effective amount of a compound of formula I as recited in claim 1 and a suitable carrier therefor.

6. A process for combinating insects or acarids which comprises treating an insect or acarid or an environment of said insect or acarid with an insecticidally or acaridally effective amount of a compound of formula I as recited in claim 1.

* * * * *